(12) United States Patent
Dai

(10) Patent No.: US 7,452,985 B2
(45) Date of Patent: Nov. 18, 2008

(54) HUMAN RON-RELATED GENE VARIANT ASSOCIATED WITH CANCERS

(75) Inventor: Ken-Shwo Dai, Taipei (TW)

(73) Assignee: Visgeneer, Inc., Hsuichu (TW)

( * ) Notice: Subject to any disclaimer, the term of this patent is extended or adjusted under 35 U.S.C. 154(b) by 0 days.

(21) Appl. No.: 11/465,308

(22) Filed: Aug. 17, 2006

(65) Prior Publication Data

US 2008/0085510 A1   Apr. 10, 2008

(51) Int. Cl.
- *C07H 21/02* (2006.01)
- *C07H 21/04* (2006.01)
- *C12N 15/00* (2006.01)
- *C12N 5/00* (2006.01)
- *C12N 5/02* (2006.01)
- *C12N 15/64* (2006.01)

(52) U.S. Cl. .................. 536/23.1; 536/23.5; 536/24.33; 435/320.1; 435/325; 435/91.4

(58) Field of Classification Search ........................ None
See application file for complete search history.

(56) References Cited

U.S. PATENT DOCUMENTS

2007/0083334 A1* 4/2007 Mintz et al. .................... 702/19

FOREIGN PATENT DOCUMENTS

| EP | 06017649.2 | 1/2007 |
|---|---|---|
| WO | WO 2004023973 A2 * | 3/2004 |

OTHER PUBLICATIONS

Wang, Kurtz, and Chen. Identification of a novel splicing product of the RON receptor tyrosine kinase in human colorectal carcinoma cells. Carcinogenesis, 2000. vol. 21, pp. 1507-1512.*

Willett et al., Differential screening of a human chromosome 3 library identifies hepatocyte growth factor-like/macrophage-stimulating protein and its receptor in injured lung. Possible implications for neuroendocrine cell survival. J Clin Invest. 99:2979-91, (1997).

Wang et al., Oncogenic and invasive potentials of human macrophage-stimulating protein receptor, the RON receptor tyrosine kinase. Carcinogenesis 24:1291-300, (2003).

Peace et al., Ron receptor signaling augments mammary tumor formation and metastasis in a murine model of breast cancer. Cancer Res. 65:1285-93, (2005).

Camp et al., RON, a tyrosine kinase receptor involved in tumor progression and metastasis.Ann Surg Oncol. 12:273-81, (2005).

Angeloni et al., The soluble sema domain of the RON receptor inhibits macrophage-stimulating protein-induced receptor activation. J. Biol. Chem. 279:3726-32, (2004).

Collesi, C., et al., A splicing variant of the RON transcript induces constitutive tyrosine kinase activity and an invasive phenotype. Molecular and Cellular Biology 16:5518-5526, (1996).

Maggiora, P., et al., Overexpression of the RON gene in human breast carcinoma. Oncogene 16:2927-2933, (1998).

Willet, C., et al., Human RON receptor protein. Database EMBL, Accession No. AAW82791, Apr. 12, 1999.

Xu, X., et al., RNA-mediated gene splicing of the RON receptor tyrosine kinase alters oncogenic phenotypes of human colorectal carcinoma cells. Oncogene 23:8464-8474, (2004).

Zhou, Y., et al., Altered expression of the RON receptor tyrosine kinase in primary human colorectal adenocarcinomas: generation of different splicing RON variants and their oncogenic potential. Oncogene 22:186-197, (2003).

* cited by examiner

*Primary Examiner*—David J. Blanchard
*Assistant Examiner*—Anne M. Gussow
(74) *Attorney, Agent, or Firm*—Baker & McKenzie LLP

(57) ABSTRACT

The invention relates to the nucleic acid and polypeptide sequences of three novel human Ron-related gene variants (Ron-V1, Ron-V2, and Ron-V3). The invention also provides a process for producing the polypeptides of the variants, as well as uses for the nucleic acid, polypeptide and antibodies to same in diagnosing human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

6 Claims, 53 Drawing Sheets

FIG. 1A-1           SEQ ID NO: 1

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| caccccctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | tgggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acgggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccggggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agttttttgcc | ccaacccgcc | 1260 |
| tggcctggaa | gccctcagcc | ccaacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctggctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | caccccacca | gtggacctct | aaggggcagt | acaaggctga | ccctgtgtgg | 1800 |
| ctccaacttc | taccttcacc | cttctggtct | ggtgcctgag | ggaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttggcacccc | aggcagtggg | 1980 |
| gcctaccaac | gtcagcctca | ccgtgactaa | catgccaccg | ggcaagcact | tccgggtaga | 2040 |
| cggcacctcc | gtgctgagag | gcttctcttt | catggagcca | gtgctgatag | cagtgcaacc | 2100 |
| cctctttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |

FIG. 1A-2    SEQ ID NO: 1 cont.

```
ggggcagctt ttatgtgcca cacccctgg ggccacggtg gccagtgtcc cccttagcct 2280
gcaggtgggg ggtgcccagg tacctggttc ctggaccttc cagtacagag aagaccctgt 2340
cgtgctaagc atcagcccca actgtggcta catcaactcc cacatcacca tctgtggcca 2400
gcatctaact tcagcatggc acttagtgct gtcattccat gacgggctta gggcagtgga 2460
aagcaggtgt gagaggcagc ttccagagca gcagctgtgc cgccttcctg aatatgtggt 2520
ccgagacccc cagggatggg tggcagggaa tctgagtgcc cgaggggatg gagctgctgg 2580
ctttacactg cctggctttc gcttcctacc cccacccat ccacccagtg ccaacctagt 2640
tccactgaag cctgaggagc atgccattaa gtttgagtat attgggctgg gcgctgtggc 2700
tgactgtgtg ggtatcaacg tgaccgtggg tggtgagagc tgccagcacg agttccgggg 2760
ggacatggtt gtctgcccc tgcccccatc cctgcagctt ggccaggatg gtgcccatt 2820
gcaggtctgc gtagatggtg aatgtcatat cctgggtaga gtggtgcggc cagggccaga 2880
tggggtccca cagagcacgc tccttggtat cctgctgcct ttgctgctgc ttgtggctgc 2940
actggcgact gcactggtct tcagctactg gtggcggagg aagcagctag ttcttcctcc 3000
caacctgaat gacctggcat ccctggacca gactgctgga gccacacccc tgcctattct 3060
gtactcgggc tctgactaca gaagtggcct tgcactccct gccattgatg gtctggattc 3120
caccacttgt gtccatggag catccttctc cgatagtgaa gatgaatcct gtgtgccact 3180
gctgcggaaa gagtccatcc agctaaggga cctggactct gcgctcttgg ctgaggtcaa 3240
ggatgtgctg attccccatg agcgggtggt cacccacagt gaccgagtca ttggcaaagg 3300
ccactttgga gttgtctacc acggagaata catagaccag gcccagaatc gaatccaatg 3360
tgccatcaag tcactaagtc gcatcacaga gatgcagcag gtggaggcct tcctgcgaga 3420
ggggctgctc atgcgtggcc tgaaccaccc gaatgtgctg gctctcattg gtatcatgtt 3480
gccacctgag ggcctgcccc atgtgctgct gccctatatg tgccacggtg acctgctcca 3540
gttcatccgc tcacctcagc ggaacccac cgtgaaggac ctcatcagct ttggcctgca 3600
ggtagcccgc ggcatggagt acctggcaga gcagaagttt gtgcacaggg acctggctgc 3660
gcggaactgc atgctggacg agtcattcac agtcaaggtg gctgactttg gtttggcccg 3720
cgacatcctg gacaggagt actatagtgt tcaacagcat cgccacgctc gcctacctgt 3780
gaagtggatg gcgctggaga gcctgcagac ctatagattt accaccaagt ctgatgtgtg 3840
gtcatttggt gtgctgctgt gggaactgct gacacgggt gccccaccat accgccacat 3900
tgaccctttt gaccttaccc acttcctggc ccagggtcgg cgcctgcccc agcctgagta 3960
ttgccctgat tctctgtacc aagtgatgca gcaatgctgg gaggcagacc cagcagtgcg 4020
acccaccttc agagtactag tgggggaggt ggagcagata gtgtctgcac tgcttgggga 4080
ccattatgtg cagctgccag caacctacat gaacttgggc cccagcacct cgcatgagat 4140
gaatgtgcgt ccagaacagc cgcagttctc acccatgcca gggaatgtac gccggccccg 4200
gccactctca gagcctcctc ggcccacttg acttagttct tgggctggac ctgcttagct 4260
gccttgagct aaccccaagg ctgcctctgg gccatgccag gccagagcag tggccctcca 4320
ccttgttcct gccctttaac tttcagaggc aataggtaaa tgggcccatt aggtccctca 4380
ctccacagag tgagccagtg agggcagtcc tgcaacatgt atttatggag tgcctgctgt 4440
ggaccctgtc ttctgggcac agtggactca gcagtgacca caccaacact gacccttgaa 4500
ccaataaagg aacaaatgac tattaaagca caaaaaaaa a             4541
```

FIG. 1B-1  SEQ ID NO: 2

```
Met Glu Leu Leu Pro Pro Leu Pro Gln Ser Phe Leu Leu Leu Leu
                  5                  10                  15
Leu Pro Ala Lys Pro Ala Ala Gly Glu Asp Trp Gln Cys Pro Arg Thr
            20                  25                  30
Pro Tyr Ala Ala Ser Arg Asp Phe Asp Val Lys Tyr Val Val Pro Ser
            35                  40                  45
Phe Ser Ala Gly Gly Leu Val Gln Ala Met Val Thr Tyr Glu Gly Asp
    50                  55                  60
Arg Asn Glu Ser Ala Val Phe Val Ala Ile Arg Asn Arg Leu His Val
65                      70                  75                  80
Leu Gly Pro Asp Leu Lys Ser Val Gln Ser Leu Ala Thr Gly Pro Ala
                85                  90                  95
Gly Asp Pro Gly Cys Gln Thr Cys Ala Ala Cys Gly Pro Gly Pro His
            100                 105                 110
Gly Pro Pro Gly Asp Thr Asp Thr Lys Val Leu Val Leu Asp Pro Ala
            115                 120                 125
Leu Pro Ala Leu Val Ser Cys Gly Ser Ser Leu Gln Gly Arg Cys Phe
    130                 135                 140
Leu His Asp Leu Glu Pro Gln Gly Thr Ala Val His Leu Ala Ala Pro
145                 150                 155                 160
Ala Cys Leu Phe Ser Ala His His Asn Arg Pro Asp Asp Cys Pro Asp
                165                 170                 175
Cys Val Ala Ser Pro Leu Gly Thr Arg Val Thr Val Val Glu Gln Gly
            180                 185                 190
Gln Ala Ser Tyr Phe Tyr Val Ala Ser Ser Leu Asp Ala Ala Val Ala
            195                 200                 205
Gly Ser Phe Ser Pro Arg Ser Val Ser Ile Arg Arg Leu Lys Ala Asp
    210                 215                 220
Ala Ser Gly Phe Ala Pro Gly Phe Val Ala Leu Ser Val Leu Pro Lys
225                 230                 235                 240
His Leu Val Ser Tyr Ser Ile Glu Tyr Val His Ser Phe His Thr Gly
                245                 250                 255
Ala Phe Val Tyr Phe Leu Thr Val Gln Pro Ala Ser Val Thr Asp Asp
            260                 265                 270
Pro Ser Ala Leu His Thr Arg Leu Ala Arg Leu Ser Ala Thr Glu Pro
            275                 280                 285
Glu Leu Gly Asp Tyr Arg Glu Leu Val Leu Asp Cys Arg Phe Ala Pro
    290                 295                 300
Lys Arg Arg Arg Arg Gly Ala Pro Glu Gly Gly Gln Pro Tyr Pro Val
305                 310                 315                 320
Leu Gln Val Ala His Ser Ala Pro Val Gly Ala Gln Leu Ala Thr Glu
                325                 330                 335
Leu Ser Ile Ala Glu Gly Gln Glu Val Leu Phe Gly Val Phe Val Thr
            340                 345                 350
Gly Lys Asp Gly Gly Pro Gly Val Gly Pro Asn Ser Val Val Cys Ala
            355                 360                 365
Phe Pro Ile Asp Leu Leu Asp Thr Leu Ile Asp Glu Gly Val Glu Arg
    370                 375                 380
Cys Cys Glu Ser Pro Val His Pro Gly Leu Arg Arg Gly Leu Asp Phe
385                 390                 395                 400
Phe Gln Ser Pro Ser Phe Cys Pro Asn Pro Pro Gly Leu Glu Ala Leu
                405                 410                 415
Ser Pro Asn Thr Ser Cys Arg His Phe Pro Leu Leu Val Ser Ser Ser
            420                 425                 430
Phe Ser Arg Val Asp Leu Phe Asn Gly Leu Leu Gly Pro Val Gln Val
            435                 440                 445
Thr Ala Leu Tyr Val Thr Arg Leu Asp Asn Val Thr Val Ala His Met
    450                 455                 460
Gly Thr Met Asp Gly Arg Ile Leu Gln Val Glu Leu Val Arg Ser Leu
465                 470                 475                 480
```

FIG. 1B-2  SEQ ID NO: 2 cont.

```
Asn Tyr Leu Leu Tyr Val Ser Asn Phe Ser Leu Gly Asp Ser Gly Gln
            485             490                 495
Pro Val Gln Arg Asp Val Ser Arg Leu Gly Asp His Leu Leu Phe Ala
            500             505                 510
Ser Gly Asp Gln Val Phe Gln Val Pro Ile Arg Gly Pro Gly Cys Arg
            515             520                 525
His Phe Leu Thr Cys Gly Arg Cys Leu Arg Ala Trp His Phe Met Gly
            530             535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
            595                 600                 605
Val Thr Val Gly Gln Ser Pro Cys Arg Pro Leu Pro Lys Asp Ser Ser
        610              615             620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
            660                 665                 670
Thr Ser Val Leu Arg Gly Phe Ser Phe Met Glu Pro Val Leu Ile Ala
            675                 680                 685
Val Gln Pro Leu Phe Gly Pro Arg Ala Gly Gly Thr Cys Leu Thr Leu
    690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
            740                 745                 750
Val Gly Gly Ala Gln Val Pro Gly Ser Trp Thr Phe Gln Tyr Arg Glu
            755                 760                 765
Asp Pro Val Val Leu Ser Ile Ser Pro Asn Cys Gly Tyr Ile Asn Ser
770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
Asp Pro Gln Gly Trp Val Ala Gly Asn Leu Ser Ala Arg Gly Asp Gly
        835                 840                 845
Ala Ala Gly Phe Thr Leu Pro Gly Phe Arg Phe Leu Pro Pro His
    850                 855                 860
Pro Pro Ser Ala Asn Leu Val Pro Leu Lys Pro Glu Glu His Ala Ile
865                 870                 875                 880
Lys Phe Glu Tyr Ile Gly Leu Gly Ala Val Ala Asp Cys Val Gly Ile
                885                 890                 895
Asn Val Thr Val Gly Gly Glu Ser Cys Gln His Glu Phe Arg Gly Asp
            900                 905                 910
Met Val Val Cys Pro Leu Pro Pro Ser Leu Gln Leu Gly Gln Asp Gly
        915                 920                 925
Ala Pro Leu Gln Val Cys Val Asp Gly Glu Cys His Ile Leu Gly Arg
    930                 935                 940
Val Val Arg Pro Gly Pro Asp Gly Val Pro Gln Ser Thr Leu Leu Gly
945                 950                 955                 960
```

FIG. 1B-3                      SEQ ID NO: 2 cont.

```
Ile Leu Leu Pro Leu Leu Leu Leu Val Ala Ala Leu Ala Thr Ala Leu
            965             970             975
Val Phe Ser Tyr Trp Trp Arg Arg Lys Gln Leu Val Leu Pro Pro Asn
            980             985             990
Leu Asn Asp Leu Ala Ser Leu Asp Gln Thr Ala Gly Ala Thr Pro Leu
            995             1000            1005
Pro Ile Leu Tyr Ser Gly Ser Asp Tyr Arg Ser Gly Leu Ala Leu Pro
            1010            1015            1020
Ala Ile Asp Gly Leu Asp Ser Thr Thr Cys Val His Gly Ala Ser Phe
1025            1030            1035            1040
Ser Asp Ser Glu Asp Glu Ser Cys Val Pro Leu Leu Arg Lys Glu Ser
            1045            1050            1055
Ile Gln Leu Arg Asp Leu Asp Ser Ala Leu Leu Ala Glu Val Lys Asp
            1060            1065            1070
Val Leu Ile Pro His Glu Arg Val Val Thr His Ser Asp Arg Val Ile
            1075            1080            1085
Gly Lys Gly His Phe Gly Val Val Tyr His Gly Glu Tyr Ile Asp Gln
            1090            1095            1100
Ala Gln Asn Arg Ile Gln Cys Ala Ile Lys Ser Leu Ser Arg Ile Thr
1105            1110            1115            1120
Glu Met Gln Gln Val Glu Ala Phe Leu Arg Glu Gly Leu Leu Met Arg
            1125            1130            1135
Gly Leu Asn His Pro Asn Val Leu Ala Leu Ile Gly Ile Met Leu Pro
            1140            1145            1150
Pro Glu Gly Leu Pro His Val Leu Leu Pro Tyr Met Cys His Gly Asp
            1155            1160            1165
Leu Leu Gln Phe Ile Arg Ser Pro Gln Arg Asn Pro Thr Val Lys Asp
            1170            1175            1180
Leu Ile Ser Phe Gly Leu Gln Val Ala Arg Gly Met Glu Tyr Leu Ala
1185            1190            1195            1200
Glu Gln Lys Phe Val His Arg Asp Leu Ala Ala Arg Asn Cys Met Leu
            1205            1210            1215
Asp Glu Ser Phe Thr Val Lys Val Ala Asp Phe Gly Leu Ala Arg Asp
            1220            1225            1230
Ile Leu Asp Arg Glu Tyr Tyr Ser Val Gln Gln His Arg His Ala Arg
            1235            1240            1245
Leu Pro Val Lys Trp Met Ala Leu Glu Ser Leu Gln Thr Tyr Arg Phe
            1250            1255            1260
Thr Thr Lys Ser Asp Val Trp Ser Phe Gly Val Leu Leu Trp Glu Leu
1265            1270            1275            1280
Leu Thr Arg Gly Ala Pro Pro Tyr Arg His Ile Asp Pro Phe Asp Leu
            1285            1290            1295
Thr His Phe Leu Ala Gln Gly Arg Arg Leu Pro Gln Pro Glu Tyr Cys
            1300            1305            1310
Pro Asp Ser Leu Tyr Gln Val Met Gln Gln Cys Trp Glu Ala Asp Pro
            1315            1320            1325
Ala Val Arg Pro Thr Phe Arg Val Leu Val Gly Glu Val Glu Gln Ile
            1330            1335            1340
Val Ser Ala Leu Leu Gly Asp His Tyr Val Gln Leu Pro Ala Thr Tyr
1345            1350            1355            1360
Met Asn Leu Gly Pro Ser Thr Ser His Glu Met Asn Val Arg Pro Glu
            1365            1370            1375
Gln Pro Gln Phe Ser Pro Met Pro Gly Asn Val Arg Arg Pro Arg Pro
            1380            1385            1390
Leu Ser Glu Pro Pro Arg Pro Thr
            1395            1400
```

FIG. 1C-1     Coding Sequence (SEQ ID NO: 1 & 2)

| | | | | | | | | | | | | | | | | |
|---|---|---|---|---|---|---|---|---|---|---|---|---|---|---|---|---|
| atg | gag | ctc | ctc | ccg | ccg | ctg | cct | cag | tcc | ttc | ctg | ttg | ctg | ctg | ctg | 48 |
| Met | Glu | Leu | Leu | Pro | Pro | Leu | Pro | Gln | Ser | Phe | Leu | Leu | Leu | Leu | Leu | |
| | | | | 5 | | | | | 10 | | | | | 15 | | |
| ttg | cct | gcc | aag | ccc | gcg | gcg | ggc | gag | gac | tgg | cag | tgc | ccg | cgc | acc | 96 |
| Leu | Pro | Ala | Lys | Pro | Ala | Ala | Gly | Glu | Asp | Trp | Gln | Cys | Pro | Arg | Thr | |
| | | | 20 | | | | | 25 | | | | | 30 | | | |
| ccc | tac | gcg | gcc | tct | cgc | gac | ttt | gac | gtg | aag | tac | gtg | gtg | ccc | agc | 144 |
| Pro | Tyr | Ala | Ala | Ser | Arg | Asp | Phe | Asp | Val | Lys | Tyr | Val | Val | Pro | Ser | |
| | | 35 | | | | | 40 | | | | | 45 | | | | |
| ttc | tcc | gcc | gga | ggc | ctg | gta | cag | gcc | atg | gtg | acc | tac | gag | ggc | gac | 192 |
| Phe | Ser | Ala | Gly | Gly | Leu | Val | Gln | Ala | Met | Val | Thr | Tyr | Glu | Gly | Asp | |
| | 50 | | | | | 55 | | | | | 60 | | | | | |
| aga | aat | gag | agt | gct | gtg | ttt | gta | gcc | ata | cgc | aat | cgc | ctg | cat | gtg | 240 |
| Arg | Asn | Glu | Ser | Ala | Val | Phe | Val | Ala | Ile | Arg | Asn | Arg | Leu | His | Val | |
| 65 | | | | | 70 | | | | | 75 | | | | | 80 | |
| ctt | ggg | cct | gac | ctg | aag | tct | gtc | cag | agc | ctg | gcc | acg | ggc | cct | gct | 288 |
| Leu | Gly | Pro | Asp | Leu | Lys | Ser | Val | Gln | Ser | Leu | Ala | Thr | Gly | Pro | Ala | |
| | | | | 85 | | | | | 90 | | | | | 95 | | |
| gga | gac | cct | ggc | tgc | cag | acg | tgt | gca | gcc | tgt | ggc | cca | gga | ccc | cac | 336 |
| Gly | Asp | Pro | Gly | Cys | Gln | Thr | Cys | Ala | Ala | Cys | Gly | Pro | Gly | Pro | His | |
| | | | 100 | | | | | 105 | | | | | 110 | | | |
| ggc | cct | ccc | ggt | gac | aca | gac | aca | aag | gtg | ctg | gtg | ctg | gat | ccc | gcg | 384 |
| Gly | Pro | Pro | Gly | Asp | Thr | Asp | Thr | Lys | Val | Leu | Val | Leu | Asp | Pro | Ala | |
| | | 115 | | | | | 120 | | | | | 125 | | | | |
| ctg | cct | gcg | ctg | gtc | agt | tgt | ggc | tcc | agc | ctg | cag | ggc | cgc | tgc | ttc | 432 |
| Leu | Pro | Ala | Leu | Val | Ser | Cys | Gly | Ser | Ser | Leu | Gln | Gly | Arg | Cys | Phe | |
| | 130 | | | | | 135 | | | | | 140 | | | | | |
| ctg | cat | gac | cta | gag | ccc | caa | ggg | aca | gcc | gtg | cat | ctg | gca | gcg | cca | 480 |
| Leu | His | Asp | Leu | Glu | Pro | Gln | Gly | Thr | Ala | Val | His | Leu | Ala | Ala | Pro | |
| 145 | | | | | 150 | | | | | 155 | | | | | 160 | |
| gcc | tgc | ctc | ttc | tca | gcc | cac | cat | aac | cgg | ccc | gat | gac | tgc | ccc | gac | 528 |
| Ala | Cys | Leu | Phe | Ser | Ala | His | His | Asn | Arg | Pro | Asp | Asp | Cys | Pro | Asp | |
| | | | | 165 | | | | | 170 | | | | | 175 | | |
| tgt | gtg | gcc | agc | cca | ttg | ggc | acc | cgt | gta | act | gtg | gtt | gag | caa | ggc | 576 |
| Cys | Val | Ala | Ser | Pro | Leu | Gly | Thr | Arg | Val | Thr | Val | Val | Glu | Gln | Gly | |
| | | | 180 | | | | | 185 | | | | | 190 | | | |
| cag | gcc | tcc | tat | ttc | tac | gtg | gca | tcc | tca | ctg | gac | gca | gcc | gtg | gct | 624 |
| Gln | Ala | Ser | Tyr | Phe | Tyr | Val | Ala | Ser | Ser | Leu | Asp | Ala | Ala | Val | Ala | |
| | | 195 | | | | | 200 | | | | | 205 | | | | |
| ggc | agc | ttc | agc | cca | cgc | tca | gtg | tct | atc | agg | cgt | ctc | aag | gct | gac | 672 |
| Gly | Ser | Phe | Ser | Pro | Arg | Ser | Val | Ser | Ile | Arg | Arg | Leu | Lys | Ala | Asp | |
| | 210 | | | | | 215 | | | | | 220 | | | | | |
| gcc | tcg | gga | ttc | gca | ccg | ggc | ttt | gtg | gcg | ttg | tca | gtg | ctg | ccc | aag | 720 |
| Ala | Ser | Gly | Phe | Ala | Pro | Gly | Phe | Val | Ala | Leu | Ser | Val | Leu | Pro | Lys | |
| 225 | | | | | 230 | | | | | 235 | | | | | 240 | |
| cat | ctt | gtc | tcc | tac | agt | att | gaa | tac | gtg | cac | agc | ttc | cac | acg | gga | 768 |
| His | Leu | Val | Ser | Tyr | Ser | Ile | Glu | Tyr | Val | His | Ser | Phe | His | Thr | Gly | |
| | | | | 245 | | | | | 250 | | | | | 255 | | |
| gcc | ttc | gta | tac | ttc | ctg | act | gta | cag | ccg | gcc | agc | gtg | aca | gat | gat | 816 |
| Ala | Phe | Val | Tyr | Phe | Leu | Thr | Val | Gln | Pro | Ala | Ser | Val | Thr | Asp | Asp | |
| | | | 260 | | | | | 265 | | | | | 270 | | | |
| cct | agt | gcc | ctg | cac | aca | cgc | ctg | gca | cgg | ctt | agc | gcc | act | gag | cca | 864 |
| Pro | Ser | Ala | Leu | His | Thr | Arg | Leu | Ala | Arg | Leu | Ser | Ala | Thr | Glu | Pro | |
| | | 275 | | | | | 280 | | | | | 285 | | | | |
| gag | ttg | ggt | gac | tat | cgg | gag | ctg | gtc | ctc | gac | tgc | aga | ttt | gct | cca | 912 |
| Glu | Leu | Gly | Asp | Tyr | Arg | Glu | Leu | Val | Leu | Asp | Cys | Arg | Phe | Ala | Pro | |
| | 290 | | | | | 295 | | | | | 300 | | | | | |
| aaa | cgc | agg | cgc | cgg | ggg | gcc | cca | gaa | ggc | gga | cag | ccc | tac | cct | gtg | 960 |
| Lys | Arg | Arg | Arg | Arg | Gly | Ala | Pro | Glu | Gly | Gly | Gln | Pro | Tyr | Pro | Val | |
| 305 | | | | | 310 | | | | | 315 | | | | | 320 | |

FIG. 1C-2  Coding Sequence (SEQ ID NO: 1 & 2) cont.

```
ctg cag gtg gcc cac tcc gct cca gtg ggt gcc caa ctt gcc act gag 1008
Leu Gln Val Ala His Ser Ala Pro Val Gly Ala Gln Leu Ala Thr Glu
            325                     330                 335
ctg agc atc gcc gag ggc cag gaa gta cta ttt ggg gtc ttt gtg act 1056
Leu Ser Ile Ala Glu Gly Gln Glu Val Leu Phe Gly Val Phe Val Thr
            340                     345                 350
ggc aag gat ggt ggt cct ggc gtg ggc ccc aac tct gtc gtc tgt gcc 1104
Gly Lys Asp Gly Gly Pro Gly Val Gly Pro Asn Ser Val Val Cys Ala
            355                     360                 365
ttc ccc att gac ctg ctg gac aca cta att gat gag ggt gtg gag cgc 1152
Phe Pro Ile Asp Leu Leu Asp Thr Leu Ile Asp Glu Gly Val Glu Arg
    370                     375                 380
tgt tgt gaa tcc cca gtc cat cca ggc ctc cgg cga ggc ctc gac ttc 1200
Cys Cys Glu Ser Pro Val His Pro Gly Leu Arg Arg Gly Leu Asp Phe
385                     390                 395                 400
ttc cag tcg ccc agt ttt tgc ccc aac ccg cct ggc ctg gaa gcc ctc 1248
Phe Gln Ser Pro Ser Phe Cys Pro Asn Pro Pro Gly Leu Glu Ala Leu
                405                     410                 415
agc ccc aac acc agc tgc cgc cac ttc cct ctg ctg gtc agt agc agc 1296
Ser Pro Asn Thr Ser Cys Arg His Phe Pro Leu Leu Val Ser Ser Ser
            420                     425                 430
ttc tca cgt gtg gac cta ttc aat ggg ctg ttg gga cca gta cag gtc 1344
Phe Ser Arg Val Asp Leu Phe Asn Gly Leu Leu Gly Pro Val Gln Val
            435                     440                 445
act gca ttg tat gtg aca cgc ctt gac aac gtc aca gtg gca cac atg 1392
Thr Ala Leu Tyr Val Thr Arg Leu Asp Asn Val Thr Val Ala His Met
    450                     455                 460
ggc aca atg gat ggg cgt atc ctg cag gtg gag ctg gtc agg tca cta 1440
Gly Thr Met Asp Gly Arg Ile Leu Gln Val Glu Leu Val Arg Ser Leu
465                     470                 475                 480
aac tac ttg ctg tat gtg tcc aac ttc tca ctg ggt gac agt ggg cag 1488
Asn Tyr Leu Leu Tyr Val Ser Asn Phe Ser Leu Gly Asp Ser Gly Gln
                485                     490                 495
ccc gtg cag cgg gat gtc agt cgt ctt ggg gac cac cta ctc ttt gcc 1536
Pro Val Gln Arg Asp Val Ser Arg Leu Gly Asp His Leu Leu Phe Ala
            500                     505                 510
tct ggg gac cag gtt ttc cag gta cct atc cga ggc cct ggc tgc cgc 1584
Ser Gly Asp Gln Val Phe Gln Val Pro Ile Arg Gly Pro Gly Cys Arg
            515                     520                 525
cac ttc ctg acc tgt ggg cgt tgc cta agg gca tgg cat ttc atg ggc 1632
His Phe Leu Thr Cys Gly Arg Cys Leu Arg Ala Trp His Phe Met Gly
    530                     535                 540
tgt ggc tgg tgt ggg aac atg tgc ggc cag cag aag gag tgt cct ggc 1680
Cys Gly Trp Cys Gly Asn Met Cys Gly Gln Gln Lys Glu Cys Pro Gly
545                     550                 555                 560
tcc tgg caa cag gac cac tgc cca cct aag ctt act gag ttc cac ccc 1728
Ser Trp Gln Gln Asp His Cys Pro Pro Lys Leu Thr Glu Phe His Pro
                565                     570                 575
cac agt gga cct cta agg ggc agt aca agg ctg acc ctg tgt ggc tcc 1776
His Ser Gly Pro Leu Arg Gly Ser Thr Arg Leu Thr Leu Cys Gly Ser
            580                     585                 590
aac ttc tac ctt cac cct tct ggt ctg gtg cct gag gga acc cat cag 1824
Asn Phe Tyr Leu His Pro Ser Gly Leu Val Pro Glu Gly Thr His Gln
    595                     600                 605
gtc act gtg ggc caa agt ccc tgc cgg cca ctg ccc aag gac agc tca 1872
Val Thr Val Gly Gln Ser Pro Cys Arg Pro Leu Pro Lys Asp Ser Ser
    610                     615                 620
aaa ctc aga cca gtg ccc cgg aaa gac ttt gta gag ttt gag tgt 1920
Lys Leu Arg Pro Val Pro Arg Lys Asp Phe Val Glu Glu Phe Glu Cys
625                     630                 635                 640
```

FIG. 1C-3          Coding Sequence (SEQ ID NO: 1 & 2) cont.

```
gaa ctg gag ccc ttg ggc acc cag gca gtg ggg cct acc aac gtc agc 1968
Glu Leu Glu Pro Leu Gly Thr Gln Ala Val Gly Pro Thr Asn Val Ser
            645                 650                 655
ctc acc gtg act aac atg cca ccg ggc aag cac ttc cgg gta gac ggc 2016
Leu Thr Val Thr Asn Met Pro Pro Gly Lys His Phe Arg Val Asp Gly
        660                 665                 670
acc tcc gtg ctg aga ggc ttc tct ttc atg gag cca gtg ctg ata gca 2064
Thr Ser Val Leu Arg Gly Phe Ser Phe Met Glu Pro Val Leu Ile Ala
            675                 680                 685
gtg caa ccc ctc ttt ggc cca cgg gca gga ggc acc tgt ctc act ctt 2112
Val Gln Pro Leu Phe Gly Pro Arg Ala Gly Gly Thr Cys Leu Thr Leu
        690                 695                 700
gaa ggc cag agt ctg tct gta ggc acc agc cgg gct gtg ctg gtc aat 2160
Glu Gly Gln Ser Leu Ser Val Gly Thr Ser Arg Ala Val Leu Val Asn
705                 710                 715                 720
ggg act gag tgt ctg cta gca cgg gtc agt gag ggg cag ctt tta tgt 2208
Gly Thr Glu Cys Leu Leu Ala Arg Val Ser Glu Gly Gln Leu Leu Cys
            725                 730                 735
gcc aca ccc cct ggg gcc acg gtg gcc agt gtc ccc ctt agc ctg cag 2256
Ala Thr Pro Pro Gly Ala Thr Val Ala Ser Val Pro Leu Ser Leu Gln
        740                 745                 750
gtg ggg ggt gcc cag gta cct ggt tcc tgg acc ttc cag tac aga gaa 2304
Val Gly Gly Ala Gln Val Pro Gly Ser Trp Thr Phe Gln Tyr Arg Glu
            755                 760                 765
gac cct gtc gtg cta agc atc agc ccc aac tgt ggc tac atc aac tcc 2352
Asp Pro Val Val Leu Ser Ile Ser Pro Asn Cys Gly Tyr Ile Asn Ser
770                 775                 780
cac atc acc atc tgt ggc cag cat cta act tca gca tgg cac tta gtg 2400
His Ile Thr Ile Cys Gly Gln His Leu Thr Ser Ala Trp His Leu Val
785                 790                 795                 800
ctg tca ttc cat gac ggg ctt agg gca gtg gaa agc agg tgt gag agg 2448
Leu Ser Phe His Asp Gly Leu Arg Ala Val Glu Ser Arg Cys Glu Arg
                805                 810                 815
cag ctt cca gag cag ctg tgc cgc ctt cct gaa tat gtc gtc cga 2496
Gln Leu Pro Glu Gln Leu Cys Arg Leu Pro Glu Tyr Val Val Arg
            820                 825                 830
gac ccc cag gga tgg gtg gca ggg aat ctg agt gcc cga ggg gat gga 2544
Asp Pro Gln Gly Trp Val Ala Gly Asn Leu Ser Ala Arg Gly Asp Gly
        835                 840                 845
gct gct ggc ttt aca ctg cct ggc ttt cgc ttc cta cca ccc cat 2592
Ala Ala Gly Phe Thr Leu Pro Gly Phe Arg Phe Leu Pro Pro Pro His
850                 855                 860
cca ccc agt gcc aac cta gtt cca ctg aag cct gag gag cat gcc att 2640
Pro Pro Ser Ala Asn Leu Val Pro Leu Lys Pro Glu Glu His Ala Ile
865                 870                 875                 880
aag ttt gag tat att ggg ctg ggc gct gtg gct gac tgt gtg ggt atc 2688
Lys Phe Glu Tyr Ile Gly Leu Gly Ala Val Ala Asp Cys Val Gly Ile
                885                 890                 895
aac gtg acc gtg ggt ggt gag agc tgc cag cac gag ttc cgg ggg gac 2736
Asn Val Thr Val Gly Gly Glu Ser Cys Gln His Glu Phe Arg Gly Asp
            900                 905                 910
atg gtt gtc tgc ccc ctg ccc cca tcc ctg cag ctt ggc cag gat ggt 2784
Met Val Val Cys Pro Leu Pro Pro Ser Leu Gln Leu Gly Gln Asp Gly
        915                 920                 925
gcc cca ttg cag gtc tgc gta gat ggt gaa tgt cat atc ctg ggt aga 2832
Ala Pro Leu Gln Val Cys Val Asp Gly Glu Cys His Ile Leu Gly Arg
930                 935                 940
gtg gtg cgg cca ggg cca gat ggg gtc cca cag agc acg ctc ctt ggt 2880
Val Val Arg Pro Gly Pro Asp Gly Val Pro Gln Ser Thr Leu Leu Gly
945                 950                 955                 960
```

FIG. 1C-4          Coding Sequence (SEQ ID NO: 1 & 2) cont.

```
atc ctg ctg cct ttg ctg ctg ctt gtg gct gca ctg gcg act gca ctg 2928
Ile Leu Leu Pro Leu Leu Leu Leu Val Ala Ala Leu Ala Thr Ala Leu
            965                     970                 975
gtc ttc agc tac tgg tgg cgg agg aag cag cta gtt ctt cct ccc aac 2976
Val Phe Ser Tyr Trp Trp Arg Arg Lys Gln Leu Val Leu Pro Pro Asn
        980                     985                 990
ctg aat gac ctg gca tcc ctg gac cag act gct gga gcc aca ccc ctg 3024
Leu Asn Asp Leu Ala Ser Leu Asp Gln Thr Ala Gly Ala Thr Pro Leu
        995                    1000                1005
cct att ctg tac tcg ggc tct gac tac aga agt ggc ctt gca ctc cct 3072
Pro Ile Leu Tyr Ser Gly Ser Asp Tyr Arg Ser Gly Leu Ala Leu Pro
       1010                    1015                1020
gcc att gat ggt ctg gat tcc acc act tgt gtc cat gga gca tcc ttc 3120
Ala Ile Asp Gly Leu Asp Ser Thr Thr Cys Val His Gly Ala Ser Phe
1025                    1030                1035                1040
tcc gat agt gaa gat gaa tcc tgt gtg cca ctg ctg cgg aaa gag tcc 3168
Ser Asp Ser Glu Asp Glu Ser Cys Val Pro Leu Leu Arg Lys Glu Ser
                    1045                1050                1055
atc cag cta agg gac ctg gac tct gcg ctc ttg gct gag gtc aag gat 3216
Ile Gln Leu Arg Asp Leu Asp Ser Ala Leu Leu Ala Glu Val Lys Asp
               1060                    1065                1070
gtg ctg att ccc cat gag cgg gtg gtc acc cac agt gac cga gtc att 3264
Val Leu Ile Pro His Glu Arg Val Val Thr His Ser Asp Arg Val Ile
           1075                    1080                1085
ggc aaa ggc cac ttt gga gtt gtc tac cac gga gaa tac ata gac cag 3312
Gly Lys Gly His Phe Gly Val Val Tyr His Gly Glu Tyr Ile Asp Gln
       1090                    1095                1100
gcc cag aat cga atc caa tgt gcc atc aag tca cta agt cgc atc aca 3360
Ala Gln Asn Arg Ile Gln Cys Ala Ile Lys Ser Leu Ser Arg Ile Thr
1105                    1110                1115                1120
gag atg cag cag gtg gag gcc ttc ctg cga gag ggg ctg ctc atg cgt 3408
Glu Met Gln Gln Val Glu Ala Phe Leu Arg Glu Gly Leu Leu Met Arg
                    1125                1130                1135
ggc ctg aac cac ccg aat gtg ctg gct ctc att ggt atc atg ttg cca 3456
Gly Leu Asn His Pro Asn Val Leu Ala Leu Ile Gly Ile Met Leu Pro
               1140                    1145                1150
cct gag ggc ctg ccc cat gtg ctg ctg ccc tat atg tgc cac ggt gac 3504
Pro Glu Gly Leu Pro His Val Leu Leu Pro Tyr Met Cys His Gly Asp
           1155                    1160                1165
ctg ctc cag ttc atc cgc tca cct cag cgg aac ccc acc gtg aag gac 3552
Leu Leu Gln Phe Ile Arg Ser Pro Gln Arg Asn Pro Thr Val Lys Asp
       1170                    1175                1180
ctc atc agc ttt ggc ctg cag gta gcc cgc ggc atg gag tac ctg gca 3600
Leu Ile Ser Phe Gly Leu Gln Val Ala Arg Gly Met Glu Tyr Leu Ala
1185                    1190                1195                1200
gag cag aag ttt gtg cac agg gac ctg gct gcg cgg aac tgc atg ctg 3648
Glu Gln Lys Phe Val His Arg Asp Leu Ala Ala Arg Asn Cys Met Leu
                    1205                1210                1215
gac gag tca ttc aca gtc aag gtg gct gac ttt ggt ttg gcc cgc gac 3696
Asp Glu Ser Phe Thr Val Lys Val Ala Asp Phe Gly Leu Ala Arg Asp
               1220                    1225                1230
atc ctg gac agg gag tac tat agt gtt caa cag cat cgc cac gct cgc 3744
Ile Leu Asp Arg Glu Tyr Tyr Ser Val Gln Gln His Arg His Ala Arg
       1235                    1240                1245
cta cct gtg aag tgg atg gcg ctg gag agc ctg cag acc tat aga ttt 3792
Leu Pro Val Lys Trp Met Ala Leu Glu Ser Leu Gln Thr Tyr Arg Phe
1250                    1255                1260
acc acc aag tct gat gtg tgg tca ttt ggt gtg ctg ctg tgg gaa ctg 3840
Thr Thr Lys Ser Asp Val Trp Ser Phe Gly Val Leu Leu Trp Glu Leu
1265                    1270                1275                1280
```

FIG. 1C-5        Coding Sequence (SEQ ID NO: 1 & 2) cont.

| ctg | aca | cgg | ggt | gcc | cca | cca | tac | cgc | cac | att | gac | cct | ttt | gac | ctt | 3888 |
|-----|-----|-----|-----|-----|-----|-----|-----|-----|-----|-----|-----|-----|-----|-----|-----|------|
| Leu | Thr | Arg | Gly | Ala | Pro | Pro | Tyr | Arg | His | Ile | Asp | Pro | Phe | Asp | Leu | |
| | | | | 1285 | | | | | 1290 | | | | | 1295 | | |
| acc | cac | ttc | ctg | gcc | cag | ggt | cgg | cgc | ctg | ccc | cag | cct | gag | tat | tgc | 3936 |
| Thr | His | Phe | Leu | Ala | Gln | Gly | Arg | Arg | Leu | Pro | Gln | Pro | Glu | Tyr | Cys | |
| | | | 1300 | | | | | 1305 | | | | | 1310 | | | |
| cct | gat | tct | ctg | tac | caa | gtg | atg | cag | caa | tgc | tgg | gag | gca | gac | cca | 3984 |
| Pro | Asp | Ser | Leu | Tyr | Gln | Val | Met | Gln | Gln | Cys | Trp | Glu | Ala | Asp | Pro | |
| | | 1315 | | | | | 1320 | | | | | 1325 | | | | |
| gca | gtg | cga | ccc | acc | ttc | aga | gta | cta | gtg | ggg | gag | gtg | gag | cag | ata | 4032 |
| Ala | Val | Arg | Pro | Thr | Phe | Arg | Val | Leu | Val | Gly | Glu | Val | Glu | Gln | Ile | |
| | 1330 | | | | | 1335 | | | | | 1340 | | | | | |
| gtg | tct | gca | ctg | ctt | ggg | gac | cat | tat | gtg | cag | ctg | cca | gca | acc | tac | 4080 |
| Val | Ser | Ala | Leu | Leu | Gly | Asp | His | Tyr | Val | Gln | Leu | Pro | Ala | Thr | Tyr | |
| 1345 | | | | | 1350 | | | | | 1355 | | | | | 1360 | |
| atg | aac | ttg | ggc | ccc | agc | acc | tcg | cat | gag | atg | aat | gtg | cgt | cca | gaa | 4128 |
| Met | Asn | Leu | Gly | Pro | Ser | Thr | Ser | His | Glu | Met | Asn | Val | Arg | Pro | Glu | |
| | | | | 1365 | | | | | 1370 | | | | | 1375 | | |
| cag | ccg | cag | ttc | tca | ccc | atg | cca | ggg | aat | gta | cgc | cgg | ccc | cgg | cca | 4176 |
| Gln | Pro | Gln | Phe | Ser | Pro | Met | Pro | Gly | Asn | Val | Arg | Arg | Pro | Arg | Pro | |
| | | | 1380 | | | | | 1385 | | | | | 1390 | | | |
| ctc | tca | gag | cct | cct | cgg | ccc | act | | | | | | | | | 4200 |
| Leu | Ser | Glu | Pro | Pro | Arg | Pro | Thr | | | | | | | | | |
| | | 1395 | | | | | 1400 | | | | | | | | | |

FIG. 2A-1    SEQ ID NO: 3

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| caccccctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | tgggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccgggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agttttgcc | ccaacccgcc | 1260 |
| tggcctggaa | gccctcagcc | ccaacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctggctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | caccccaca | gtggacctct | aaggggcagt | acaaggctga | ccctgtgtgg | 1800 |
| ctccaacttc | taccttcacc | cttctggtct | ggtgcctgag | gaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttgggcaccc | aggcagtggg | 1980 |
| gcctaccaac | gtcagcctca | ccgtgactaa | catgccaccg | ggcaagcact | tccgggtaga | 2040 |
| cggcacctcc | gtgctgagag | gcttctcttt | catggagcca | tgctgatag | cagtgcaacc | 2100 |
| cctctttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |
| ggggcagctt | ttatgtgcca | cacccctgg | ggccacggtg | gccagtgtcc | ccttagcct | 2280 |

FIG. 2A-2         SEQ ID NO: 3 cont.

```
gcaggtgggg ggtgcccagg tacctggttc ctggaccttc cagtacagag aagaccctgt 2340
cgtgctaagc atcagcccca actgtggcta catcaactcc cacatcacca tctgtggcca 2400
gcatctaact tcagcatggc acttagtgct gtcattccat gacgggctta gggcagtgga 2460
aagcaggtgt gagaggcagc ttccagagca gcagctgtgc cgccttcctg aatatgtggt 2520
ccgagacccc cagggatggg tggcagggaa tctgagtgcc cgaggggatg gagctgctgg 2580
ctttacactg cctggctttc gcttcctacc cccacccat ccacccagtg ccaacctagt 2640
tccactgaag cctgaggagc atgccattaa gtttgagtat attgggctgg gcgctgtggc 2700
tgactgtgtg ggtatcaacg tgaccgtggg tggtgagagc tgccagcacg agttccgggg 2760
ggacatggtt gtctgccccc tgcccccatc cctgcagctt ggccaggatg gtgcccatt 2820
gcaggtctgc gtagatgcac tccctgccat tgatggtctg gattccacca cttgtgtcca 2880
tggagcatcc ttctccgata gtgaagatga atcctgtgtg ccactgctgc ggaaagagtc 2940
catccagcta agggacctgg actctgcgct cttggctgag gtcaaggatg tgctgattcc 3000
ccatgagcgg gtggtcaccc acagtgaccg agtcattggc aaaggccact ttggagttgt 3060
ctaccacgga gaatacatag accaggccca gaatcgaatc caatgtgcca tcaagtcact 3120
aagtcgcatc acagagatgc agcaggtgga ggccttcctg cgagaggggc tgctcatgcg 3180
tggcctgaac cacccgaatg tgctggctct cattggtatc atgttgccac ctgagggcct 3240
gccccatgtg ctgctgccct atatgtgcca cggtgacctg ctccagttca tccgctcacc 3300
tcagcggaac cccaccgtga aggacctcat cagctttggc ctgcaggtag cccgcggcat 3360
ggagtacctg gcagagcaga agtttgtgca cagggacctg gctgcgcgga actgcatgct 3420
ggacgagtca ttcacagtca aggtggctga ctttggtttg gcccgcgaca tcctggacag 3480
ggagtactat agtgttcaac agcatcgcca cgctcgccta cctgtgaagt ggatggcgct 3540
ggagagcctg cagacctata gatttaccac caagtctgat gtggtaccaa gtgatgcagc 3600
aatgctggga ggcagaccca gcagtgcgac ccaccttcag agtactagtg ggggaggtgg 3660
agcagatagt gtctgcactg cttggggacc attatgtgca gctgccagca acctacatga 3720
acttgagcta accccaaggc tgcctctggg ccatgccagg ccagagcagt ggccctccac 3780
cttgttcctg ccctttaact ttcagaggca ataggtaaat gggcccatta ggtccctcac 3840
tccacagagt gagccagtga gggcagtcct gcaacatgta tttatggagt gcctgctgtg 3900
gaccctgtct tctgggcaca gtggactcag cagtgaccac accaacactg acccttgaac 3960
caataaagga acaaatgact attaaagcac aaaaaaaaa                        4000
```

FIG. 2B-1                           SEQ ID NO: 4

| | | | | | | | | | | | | | | |
|---|---|---|---|---|---|---|---|---|---|---|---|---|---|---|
| Met | Glu | Leu | Leu | Pro 5 | Pro | Leu | Pro | Gln | Ser 10 | Phe | Leu | Leu | Leu 15 | Leu |
| Leu | Pro | Ala | Lys 20 | Pro | Ala | Ala | Gly | Glu | Asp 25 | Trp | Gln | Cys | Pro 30 | Arg | Thr |
| Pro | Tyr | Ala 35 | Ala | Ser | Arg | Asp | Phe 40 | Asp | Val | Lys | Tyr | Val 45 | Val | Pro | Ser |
| Phe | Ser 50 | Ala | Gly | Gly | Leu | Val 55 | Gln | Ala | Met | Val | Thr 60 | Tyr | Glu | Gly | Asp |
| Arg 65 | Asn | Glu | Ser | Ala | Val 70 | Phe | Val | Ala | Ile | Arg 75 | Asn | Arg | Leu | His | Val 80 |
| Leu | Gly | Pro | Asp | Leu 85 | Lys | Ser | Val | Gln | Ser 90 | Leu | Ala | Thr | Gly | Pro 95 | Ala |
| Gly | Asp | Pro | Gly 100 | Cys | Gln | Thr | Cys | Ala 105 | Ala | Cys | Gly | Pro | Gly 110 | Pro | His |
| Gly | Pro | Pro 115 | Gly | Asp | Thr | Asp | Thr 120 | Lys | Val | Leu | Val | Leu 125 | Asp | Pro | Ala |
| Leu | Pro 130 | Ala | Leu | Val | Ser | Cys 135 | Gly | Ser | Ser | Leu | Gln 140 | Gly | Arg | Cys | Phe |
| Leu 145 | His | Asp | Leu | Glu | Pro 150 | Gln | Gly | Thr | Ala | Val 155 | His | Leu | Ala | Ala | Pro 160 |
| Ala | Cys | Leu | Phe | Ser 165 | Ala | His | His | Asn | Arg 170 | Pro | Asp | Asp | Cys | Pro 175 | Asp |
| Cys | Val | Ala | Ser 180 | Pro | Leu | Gly | Thr | Arg 185 | Val | Thr | Val | Val | Glu 190 | Gln | Gly |
| Gln | Ala | Ser 195 | Tyr | Phe | Tyr | Val | Ala 200 | Ser | Ser | Leu | Asp | Ala 205 | Ala | Val | Ala |
| Gly | Ser 210 | Phe | Ser | Pro | Arg | Ser 215 | Val | Ser | Ile | Arg | Arg 220 | Leu | Lys | Ala | Asp |
| Ala 225 | Ser | Gly | Phe | Ala | Pro 230 | Gly | Phe | Val | Ala | Leu 235 | Ser | Val | Leu | Pro | Lys 240 |
| His | Leu | Val | Ser | Tyr 245 | Ser | Ile | Glu | Tyr | Val 250 | His | Ser | Phe | His | Thr 255 | Gly |
| Ala | Phe | Val | Tyr 260 | Phe | Leu | Thr | Val | Gln 265 | Pro | Ala | Ser | Val | Thr 270 | Asp | Asp |
| Pro | Ser | Ala 275 | Leu | His | Thr | Arg | Leu 280 | Ala | Arg | Leu | Ser | Ala 285 | Thr | Glu | Pro |
| Glu | Leu 290 | Gly | Asp | Tyr | Arg | Glu 295 | Leu | Val | Leu | Asp | Cys 300 | Arg | Phe | Ala | Pro |
| Lys 305 | Arg | Arg | Arg | Arg | Gly 310 | Ala | Pro | Glu | Gly | Gly 315 | Gln | Pro | Tyr | Pro | Val 320 |
| Leu | Gln | Val | Ala | His 325 | Ser | Ala | Pro | Val | Gly 330 | Ala | Gln | Leu | Ala | Thr 335 | Glu |
| Leu | Ser | Ile | Ala 340 | Glu | Gly | Gln | Glu | Val 345 | Leu | Phe | Gly | Val | Phe 350 | Val | Thr |
| Gly | Lys | Asp 355 | Gly | Gly | Pro | Gly | Val 360 | Gly | Pro | Asn | Ser | Val 365 | Val | Cys | Ala |
| Phe | Pro 370 | Ile | Asp | Leu | Leu | Asp 375 | Thr | Leu | Ile | Asp | Glu 380 | Gly | Val | Glu | Arg |
| Cys 385 | Cys | Glu | Ser | Pro | Val 390 | His | Pro | Gly | Leu | Arg 395 | Arg | Gly | Leu | Asp | Phe 400 |
| Phe | Gln | Ser | Pro | Ser 405 | Phe | Cys | Pro | Asn | Pro 410 | Pro | Gly | Leu | Glu | Ala 415 | Leu |
| Ser | Pro | Asn | Thr 420 | Ser | Cys | Arg | His | Phe 425 | Pro | Leu | Leu | Val | Ser 430 | Ser | Ser |
| Phe | Ser | Arg 435 | Val | Asp | Leu | Phe | Asn 440 | Gly | Leu | Leu | Gly | Pro 445 | Val | Gln | Val |
| Thr | Ala 450 | Leu | Tyr | Val | Thr | Arg 455 | Leu | Asp | Asn | Val | Thr 460 | Val | Ala | His | Met |
| Gly 465 | Thr | Met | Asp | Gly | Arg 470 | Ile | Leu | Gln | Val | Glu 475 | Leu | Val | Arg | Ser | Leu 480 |

FIG. 2B-2  SEQ ID NO: 4 cont.

```
Asn Tyr Leu Leu Tyr Val Ser Asn Phe Ser Leu Gly Asp Ser Gly Gln
            485                 490                 495
Pro Val Gln Arg Asp Val Ser Arg Leu Gly Asp His Leu Leu Phe Ala
        500                 505                 510
Ser Gly Asp Gln Val Phe Gln Val Pro Ile Arg Gly Pro Gly Cys Arg
            515                 520                 525
His Phe Leu Thr Cys Gly Arg Cys Leu Arg Ala Trp His Phe Met Gly
    530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
        595                 600                 605
Val Thr Val Gly Gln Ser Pro Cys Arg Pro Leu Pro Lys Asp Ser Ser
    610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
            660                 665                 670
Thr Ser Val Leu Arg Gly Phe Ser Phe Met Glu Pro Val Leu Ile Ala
        675                 680                 685
Val Gln Pro Leu Phe Gly Pro Arg Ala Gly Gly Thr Cys Leu Thr Leu
    690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
            740                 745                 750
Val Gly Gly Ala Gln Val Pro Gly Ser Trp Thr Phe Gln Tyr Arg Glu
        755                 760                 765
Asp Pro Val Val Leu Ser Ile Ser Pro Asn Cys Gly Tyr Ile Asn Ser
    770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
Asp Pro Gln Gly Trp Val Ala Gly Asn Leu Ser Ala Arg Gly Asp Gly
        835                 840                 845
Ala Ala Gly Phe Thr Leu Pro Gly Phe Arg Phe Leu Pro Pro His
    850                 855                 860
Pro Pro Ser Ala Asn Leu Val Pro Leu Lys Pro Glu Glu His Ala Ile
865                 870                 875                 880
Lys Phe Glu Tyr Ile Gly Leu Gly Ala Val Ala Asp Cys Val Gly Ile
                885                 890                 895
Asn Val Thr Val Gly Gly Glu Ser Cys Gln His Glu Phe Arg Gly Asp
            900                 905                 910
Met Val Val Cys Pro Leu Pro Pro Ser Leu Gln Leu Gly Gln Asp Gly
        915                 920                 925
Ala Pro Leu Gln Val Cys Val Asp Ala Leu Pro Ala Ile Asp Gly Leu
    930                 935                 940
Asp Ser Thr Thr Cys Val His Gly Ala Ser Phe Ser Asp Ser Glu Asp
945                 950                 955                 960
```

FIG. 2B-3  SEQ ID NO: 4 cont.

```
Glu Ser Cys Val Pro Leu Leu Arg Lys Glu Ser Ile Gln Leu Arg Asp
            965                 970                 975
Leu Asp Ser Ala Leu Leu Ala Glu Val Lys Asp Val Leu Ile Pro His
            980                 985                 990
Glu Arg Val Val Thr His Ser Asp Arg Val Ile Gly Lys Gly His Phe
            995                 1000                1005
Gly Val Val Tyr His Gly Glu Tyr Ile Asp Gln Ala Gln Asn Arg Ile
    1010                1015                1020
Gln Cys Ala Ile Lys Ser Leu Ser Arg Ile Thr Glu Met Gln Gln Val
1025                1030                1035                1040
Glu Ala Phe Leu Arg Glu Gly Leu Leu Met Arg Gly Leu Asn His Pro
            1045                1050                1055
Asn Val Leu Ala Leu Ile Gly Ile Met Leu Pro Pro Glu Gly Leu Pro
            1060                1065                1070
His Val Leu Leu Pro Tyr Met Cys His Gly Asp Leu Leu Gln Phe Ile
            1075                1080                1085
Arg Ser Pro Gln Arg Asn Pro Thr Val Lys Asp Leu Ile Ser Phe Gly
    1090                1095                1100
Leu Gln Val Ala Arg Gly Met Glu Tyr Leu Ala Glu Gln Lys Phe Val
1105                1110                1115                1120
His Arg Asp Leu Ala Ala Arg Asn Cys Met Leu Asp Glu Ser Phe Thr
            1125                1130                1135
Val Lys Val Ala Asp Phe Gly Leu Ala Arg Asp Ile Leu Asp Arg Glu
            1140                1145                1150
Tyr Tyr Ser Val Gln Gln His Arg His Ala Arg Leu Pro Val Lys Trp
            1155                1160                1165
Met Ala Leu Glu Ser Leu Gln Thr Tyr Arg Phe Thr Thr Lys Ser Asp
    1170                1175                1180
Val Val Pro Ser Asp Ala Ala Met Leu Gly Gly Arg Pro Ser Ser Ala
1185                1190                1195                1200
Thr His Leu Gln Ser Thr Ser Gly Gly Gly Ala Asp Ser Val Cys
            1205                1210                1215
Thr Ala Trp Gly Pro Leu Cys Ala Ala Ala Ser Asn Leu His Glu Leu
            1220                1225                1230
Glu Leu Thr Pro Arg Leu Pro Leu Gly His Ala Arg Pro Glu Gln Trp
            1235                1240                1245
Pro Ser Thr Leu Phe Leu Pro Phe Asn Phe Gln Arg Gln
    1250                1255                1260
```

FIG. 2C-1  Coding Sequence (SEQ ID NO: 3 & 4)

```
atg gag ctc ctc ccg ccg ctg cct cag tcc ttc ctg ttg ctg ctg     48
Met Glu Leu Leu Pro Pro Leu Pro Gln Ser Phe Leu Leu Leu Leu
                  5               10              15
ttg cct gcc aag ccc gcg gcg ggc gag gac tgg cag tgc ccg cgc acc 96
Leu Pro Ala Lys Pro Ala Ala Gly Glu Asp Trp Gln Cys Pro Arg Thr
                20              25              30
ccc tac gcg gcc tct cgc gac ttt gac gtg aag tac gtg gtg ccc agc 144
Pro Tyr Ala Ala Ser Arg Asp Phe Asp Val Lys Tyr Val Val Pro Ser
            35              40              45
ttc tcc gcc gga ggc ctg gta cag gcc atg gtg acc tac gag ggc gac 192
Phe Ser Ala Gly Gly Leu Val Gln Ala Met Val Thr Tyr Glu Gly Asp
        50              55              60
aga aat gag agt gct gtg ttt gta gcc ata cgc aat cgc ctg cat gtg 240
Arg Asn Glu Ser Ala Val Phe Val Ala Ile Arg Asn Arg Leu His Val
65              70              75              80
ctt ggg cct gac ctg aag tct gtc cag agc ctg gcc acg ggc cct gct 288
Leu Gly Pro Asp Leu Lys Ser Val Gln Ser Leu Ala Thr Gly Pro Ala
                85              90              95
gga gac cct ggc tgc cag acg tgt gca gcc tgt ggc cca gga ccc cac 336
Gly Asp Pro Gly Cys Gln Thr Cys Ala Ala Cys Gly Pro Gly Pro His
                100             105             110
ggc cct ccc ggt gac aca gac aca aag gtg ctg gtg ctg gat ccc gcg 384
Gly Pro Pro Gly Asp Thr Asp Thr Lys Val Leu Val Leu Asp Pro Ala
        115             120             125
ctg cct gcg ctg gtc agt tgt ggc tcc agc ctg cag ggc cgc tgc ttc 432
Leu Pro Ala Leu Val Ser Cys Gly Ser Ser Leu Gln Gly Arg Cys Phe
    130             135             140
ctg cat gac cta gag ccc caa ggg aca gcc gtg cat ctg gca gcg cca 480
Leu His Asp Leu Glu Pro Gln Gly Thr Ala Val His Leu Ala Ala Pro
145             150             155             160
gcc tgc ctc ttc tca gcc cac cat aac cgg ccc gat gac tgc ccc gac 528
Ala Cys Leu Phe Ser Ala His His Asn Arg Pro Asp Asp Cys Pro Asp
                165             170             175
tgt gtg gcc agc cca ttg ggc acc cgt gta act gtg gtt gag caa ggc 576
Cys Val Ala Ser Pro Leu Gly Thr Arg Val Thr Val Val Glu Gln Gly
                180             185             190
cag gcc tcc tat ttc tac gtg gca tcc tca ctg gac gca gcc gtg gct 624
Gln Ala Ser Tyr Phe Tyr Val Ala Ser Ser Leu Asp Ala Ala Val Ala
        195             200             205
ggc agc ttc agc cca cgc tca gtg tct atc agg cgt ctc aag gct gac 672
Gly Ser Phe Ser Pro Arg Ser Val Ser Ile Arg Arg Leu Lys Ala Asp
        210             215             220
gcc tcg gga ttc gca ccg ggc ttt gtg gcg ttg tca gtg ctg ccc aag 720
Ala Ser Gly Phe Ala Pro Gly Phe Val Ala Leu Ser Val Leu Pro Lys
225             230             235             240
cat ctt gtc tcc tac agt att gaa tac gtg cac agc ttc cac acg gga 768
His Leu Val Ser Tyr Ser Ile Glu Tyr Val His Ser Phe His Thr Gly
                245             250             255
gcc ttc gta tac ttc ctg act gta cag ccg gcc agc gtg aca gat gat 816
Ala Phe Val Tyr Phe Leu Thr Val Gln Pro Ala Ser Val Thr Asp Asp
                260             265             270
cct agt gcc ctg cac aca cgc ctg gca cgg ctt agc gcc act gag cca 864
Pro Ser Ala Leu His Thr Arg Leu Ala Arg Leu Ser Ala Thr Glu Pro
        275             280             285
gag ttg ggt gac tat cgg gag ctg gtc ctc gac tgc aga ttt gct cca 912
Glu Leu Gly Asp Tyr Arg Glu Leu Val Leu Asp Cys Arg Phe Ala Pro
        290             295             300
aaa cgc agg cgc cgg ggg gcc cca gaa ggc gga cag ccc tac cct gtg 960
Lys Arg Arg Arg Arg Gly Ala Pro Glu Gly Gly Gln Pro Tyr Pro Val
305             310             315             320
```

FIG. 2C-2               Coding Sequence (SEQ ID NO: 3 & 4) cont.

```
ctg cag gtg gcc cac tcc gct cca gtg ggt gcc caa ctt gcc act gag 1008
Leu Gln Val Ala His Ser Ala Pro Val Gly Ala Gln Leu Ala Thr Glu
            325                 330                 335
ctg agc atc gcc gag ggc cag gaa gta cta ttt ggg gtc ttt gtg act 1056
Leu Ser Ile Ala Glu Gly Gln Glu Val Leu Phe Gly Val Phe Val Thr
            340                 345                 350
ggc aag gat ggt ggt cct ggc gtg ggc ccc aac tct gtc gtc tgt gcc 1104
Gly Lys Asp Gly Gly Pro Gly Val Gly Pro Asn Ser Val Val Cys Ala
            355                 360                 365
ttc ccc att gac ctg ctg gac aca cta att gat gag ggt gtg gag cgc 1152
Phe Pro Ile Asp Leu Leu Asp Thr Leu Ile Asp Glu Gly Val Glu Arg
            370                 375                 380
tgt tgt gaa tcc cca gtc cat cca ggc ctc cgg cga ggc ctc gac ttc 1200
Cys Cys Glu Ser Pro Val His Pro Gly Leu Arg Arg Gly Leu Asp Phe
385                 390                 395                 400
ttc cag tcg ccc agt ttt tgc ccc aac ccg cct ggc ctg gaa gcc ctc 1248
Phe Gln Ser Pro Ser Phe Cys Pro Asn Pro Pro Gly Leu Glu Ala Leu
            405                 410                 415
agc ccc aac acc agc tgc cgc cac ttc cct ctg ctg gtc agt agc agc 1296
Ser Pro Asn Thr Ser Cys Arg His Phe Pro Leu Leu Val Ser Ser Ser
            420                 425                 430
ttc tca cgt gtg gac cta ttc aat ggg ctg ttg gga cca gta cag gtc 1344
Phe Ser Arg Val Asp Leu Phe Asn Gly Leu Leu Gly Pro Val Gln Val
            435                 440                 445
act gca ttg tat gtg aca cgc ctt gac aac gtc aca gtg gca cac atg 1392
Thr Ala Leu Tyr Val Thr Arg Leu Asp Asn Val Thr Val Ala His Met
            450                 455                 460
ggc aca atg gat ggg cgt atc ctg cag gtg gag ctg gtc agg tca cta 1440
Gly Thr Met Asp Gly Arg Ile Leu Gln Val Glu Leu Val Arg Ser Leu
465                 470                 475                 480
aac tac ttg ctg tat gtg tcc aac ttc tca ctg ggt gac agt ggg cag 1488
Asn Tyr Leu Leu Tyr Val Ser Asn Phe Ser Leu Gly Asp Ser Gly Gln
            485                 490                 495
ccc gtg cag cgg gat gtc agt cgt ctt ggg gac cac cta ctc ttt gcc 1536
Pro Val Gln Arg Asp Val Ser Arg Leu Gly Asp His Leu Leu Phe Ala
            500                 505                 510
tct ggg gac cag gtt ttc cag gta cct atc cga ggc cct ggc tgc cgc 1584
Ser Gly Asp Gln Val Phe Gln Val Pro Ile Arg Gly Pro Gly Cys Arg
            515                 520                 525
cac ttc ctg acc tgt ggg cgt tgc cta agg gca tgg cat ttc atg ggc 1632
His Phe Leu Thr Cys Gly Arg Cys Leu Arg Ala Trp His Phe Met Gly
            530                 535                 540
tgt ggc tgg tgt ggg aac atg tgc ggc cag cag aag gag tgt cct ggc 1680
Cys Gly Trp Cys Gly Asn Met Cys Gly Gln Gln Lys Glu Cys Pro Gly
545                 550                 555                 560
tcc tgg caa cag gac cac tgc cca cct aag ctt act gag ttc cac ccc 1728
Ser Trp Gln Gln Asp His Cys Pro Pro Lys Leu Thr Glu Phe His Pro
            565                 570                 575
cac agt gga cct cta agg ggc agt aca agg ctg acc ctg tgt ggc tcc 1776
His Ser Gly Pro Leu Arg Gly Ser Thr Arg Leu Thr Leu Cys Gly Ser
            580                 585                 590
aac ttc tac ctt cac cct tct ggt ctg gtg cct gag gga acc cat cag 1824
Asn Phe Tyr Leu His Pro Ser Gly Leu Val Pro Glu Gly Thr His Gln
            595                 600                 605
gtc act gtg ggc caa agt ccc tgc cgg cca ctg ccc aag gac agc tca 1872
Val Thr Val Gly Gln Ser Pro Cys Arg Pro Leu Pro Lys Asp Ser Ser
            610                 615                 620
aaa ctc aga cca gtg ccc cgg aaa gac ttt gta gag gag ttt gag tgt 1920
Lys Leu Arg Pro Val Pro Arg Lys Asp Phe Val Glu Glu Phe Glu Cys
625                 630                 635                 640
```

FIG. 2C-3                      Coding Sequence (SEQ ID NO: 3 & 4) cont.

```
gaa ctg gag ccc ttg ggc acc cag gca gtg ggg cct acc aac gtc agc  1968
Glu Leu Glu Pro Leu Gly Thr Gln Ala Val Gly Pro Thr Asn Val Ser
            645                     650                     655
ctc acc gtg act aac atg cca ccg ggc aag cac ttc cgg gta gac ggc  2016
Leu Thr Val Thr Asn Met Pro Pro Gly Lys His Phe Arg Val Asp Gly
    660                     665                     670
acc tcc gtg ctg aga ggc ttc tct ttc atg gag cca gtg ctg ata gca  2064
Thr Ser Val Leu Arg Gly Phe Ser Phe Met Glu Pro Val Leu Ile Ala
        675                     680                     685
gtg caa ccc ctc ttt ggc cca cgg gca gga ggc acc tgt ctc act ctt  2112
Val Gln Pro Leu Phe Gly Pro Arg Ala Gly Gly Thr Cys Leu Thr Leu
            690                     695                     700
gaa ggc cag agt ctg tct gta ggc acc agc cgg gct gtg ctg gtc aat  2160
Glu Gly Gln Ser Leu Ser Val Gly Thr Ser Arg Ala Val Leu Val Asn
705                     710                     715                 720
ggg act gag tgt ctg cta gca cgg gtc agt gag ggg cag ctt tta tgt  2208
Gly Thr Glu Cys Leu Leu Ala Arg Val Ser Glu Gly Gln Leu Leu Cys
            725                     730                     735
gcc aca ccc cct ggg gcc acg gtg gcc agt gtc ccc ctt agc ctg cag  2256
Ala Thr Pro Pro Gly Ala Thr Val Ala Ser Val Pro Leu Ser Leu Gln
        740                     745                     750
gtg ggg ggt gcc cag gta cct ggt tcc tgg acc ttc cag tac aga gaa  2304
Val Gly Gly Ala Gln Val Pro Gly Ser Trp Thr Phe Gln Tyr Arg Glu
            755                     760                     765
gac cct gtc gtg cta agc atc agc ccc aac tgt ggc tac atc aac tcc  2352
Asp Pro Val Val Leu Ser Ile Ser Pro Asn Cys Gly Tyr Ile Asn Ser
        770                     775                     780
cac atc acc atc tgt ggc cag cat cta act tca gca tgg cac tta gtg  2400
His Ile Thr Ile Cys Gly Gln His Leu Thr Ser Ala Trp His Leu Val
785                     790                     795                 800
ctg tca ttc cat gac ggg ctt agg gca gtg gaa agc agg tgt gag agg  2448
Leu Ser Phe His Asp Gly Leu Arg Ala Val Glu Ser Arg Cys Glu Arg
            805                     810                     815
cag ctt cca gag cag cag ctg tgc cgc ctt cct gaa tat gtg gtc cga  2496
Gln Leu Pro Glu Gln Gln Leu Cys Arg Leu Pro Glu Tyr Val Val Arg
        820                     825                     830
gac ccc cag gga tgg gtg gca ggg aat ctg agt gcc cga ggg gat gga  2544
Asp Pro Gln Gly Trp Val Ala Gly Asn Leu Ser Ala Arg Gly Asp Gly
            835                     840                     845
gct gct ggc ttt aca ctg cct ggc ttt cgc ttc cta ccc cca ccc cat  2592
Ala Ala Gly Phe Thr Leu Pro Gly Phe Arg Phe Leu Pro Pro Pro His
    850                     855                     860
cca ccc agt gcc aac cta gtt cca ctg aag cct gag gag cat gcc att  2640
Pro Pro Ser Ala Asn Leu Val Pro Leu Lys Pro Glu Glu His Ala Ile
865                     870                     875                 880
aag ttt gag tat att ggg ctg ggc gct gtg gct gac tgt gtg ggt atc  2688
Lys Phe Glu Tyr Ile Gly Leu Gly Ala Val Ala Asp Cys Val Gly Ile
                885                     890                     895
aac gtg acc gtg ggt ggt gag agc tgc cag cac gag ttc cgg ggg gac  2736
Asn Val Thr Val Gly Gly Glu Ser Cys Gln His Glu Phe Arg Gly Asp
            900                     905                     910
atg gtt gtc tgc ccc ctg ccc cca tcc ctg cag ctt ggc cag gat ggt  2784
Met Val Val Cys Pro Leu Pro Pro Ser Leu Gln Leu Gly Gln Asp Gly
        915                     920                     925
gcc cca ttg cag gtc tgc gta gat gca ctc cct gcc att gat ggt ctg  2832
Ala Pro Leu Gln Val Cys Val Asp Ala Leu Pro Ala Ile Asp Gly Leu
930                     935                     940
gat tcc acc act tgt gtc cat gga gca tcc ttc tcc gat agt gaa gat  2880
Asp Ser Thr Thr Cys Val His Gly Ala Ser Phe Ser Asp Ser Glu Asp
945                     950                     955                 960
```

FIG. 2C-4  Coding Sequence (SEQ ID NO: 3 & 4) cont.

```
gaa tcc tgt gtg cca ctg ctg cgg aaa gag tcc atc cag cta agg gac 2928
Glu Ser Cys Val Pro Leu Leu Arg Lys Glu Ser Ile Gln Leu Arg Asp
            965                 970                 975
ctg gac tct gcg ctc ttg gct gag gtc aag gat gtg ctg att ccc cat 2976
Leu Asp Ser Ala Leu Leu Ala Glu Val Lys Asp Val Leu Ile Pro His
            980                 985                 990
gag cgg gtg gtc acc cac agt gac cga gtc att ggc aaa ggc cac ttt 3024
Glu Arg Val Val Thr His Ser Asp Arg Val Ile Gly Lys Gly His Phe
            995                 1000                1005
gga gtt gtc tac cac gga gaa tac ata gac cag gcc cag aat cga atc 3072
Gly Val Val Tyr His Gly Glu Tyr Ile Asp Gln Ala Gln Asn Arg Ile
        1010                1015                1020
caa tgt gcc atc aag tca cta agt cgc atc aca gag atg cag cag gtg 3120
Gln Cys Ala Ile Lys Ser Leu Ser Arg Ile Thr Glu Met Gln Gln Val
1025                1030                1035                1040
gag gcc ttc ctg cga gag ggg ctc ctc atg cgt ggc ctg aac cac ccg 3168
Glu Ala Phe Leu Arg Glu Gly Leu Leu Met Arg Gly Leu Asn His Pro
                1045                1050                1055
aat gtg ctg gct ctc att ggt atc atg ttg cca cct gag ggc ctg ccc 3216
Asn Val Leu Ala Leu Ile Gly Ile Met Leu Pro Pro Glu Gly Leu Pro
                1060                1065                1070
cat gtg ctg ctg ccc tat atg tgc cac ggt gac ctg ctc cag ttc atc 3264
His Val Leu Leu Pro Tyr Met Cys His Gly Asp Leu Leu Gln Phe Ile
            1075                1080                1085
cgc tca cct cag cgg aac ccc acc gtg aag gac ctc atc agc ttt ggc 3312
Arg Ser Pro Gln Arg Asn Pro Thr Val Lys Asp Leu Ile Ser Phe Gly
        1090                1095                1100
ctg cag gta gcc cgc ggc atg gag tac ctg gca gag cag aag ttt gtg 3360
Leu Gln Val Ala Arg Gly Met Glu Tyr Leu Ala Glu Gln Lys Phe Val
1105                1110                1115                1120
cac agg gac ctg gct gcg cgg aac tgc atg ctg gac gag tca ttc aca 3408
His Arg Asp Leu Ala Ala Arg Asn Cys Met Leu Asp Glu Ser Phe Thr
                1125                1130                1135
gtc aag gtg gct gac ttt ggt ttg gcc cgc gac atc ctg gac agg gag 3456
Val Lys Val Ala Asp Phe Gly Leu Ala Arg Asp Ile Leu Asp Arg Glu
                1140                1145                1150
tac tat agt gtt caa cag cat cgc cac gct cgc cta cct gtg aag tgg 3504
Tyr Tyr Ser Val Gln Gln His Arg His Ala Arg Leu Pro Val Lys Trp
            1155                1160                1165
atg gcg ctg gag agc ctg cag acc tat aga ttt acc acc aag tct gat 3552
Met Ala Leu Glu Ser Leu Gln Thr Tyr Arg Phe Thr Thr Lys Ser Asp
        1170                1175                1180
gtg gta cca agt gat gca gca atg ctg gga ggc aga ccc agc agt gcg 3600
Val Val Pro Ser Asp Ala Ala Met Leu Gly Gly Arg Pro Ser Ser Ala
1185                1190                1195                1200
acc cac ctt cag agt act agt ggg gga ggt gga gca gat agt gtc tgc 3648
Thr His Leu Gln Ser Thr Ser Gly Gly Gly Gly Ala Asp Ser Val Cys
                1205                1210                1215
act gct tgg gga cca tta tgt gca gct gcc agc aac cta cat gaa ctt 3696
Thr Ala Trp Gly Pro Leu Cys Ala Ala Ala Ser Asn Leu His Glu Leu
                1220                1225                1230
gag cta acc cca agg ctg cct ctg ggc cat gcc agg cca gag cag tgg 3744
Glu Leu Thr Pro Arg Leu Pro Leu Gly His Ala Arg Pro Glu Gln Trp
            1235                1240                1245
ccc tcc acc ttg ttc ctg ccc ttt aac ttt cag agg caa                 3783
Pro Ser Thr Leu Phe Leu Pro Phe Asn Phe Gln Arg Gln
        1250                1255                1260
```

FIG. 3A-1          SEQ ID NO: 5

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| cacccctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | tgggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acgggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccgggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agtttttgcc | ccaacccgcc | 1260 |
| tggcctggaa | gccctcagcc | ccaacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctgctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | cacccccaca | gtggacctct | aagggggcagt | acaaggctga | ccctgtgtgg | 1800 |
| ctccaacttc | taccttcacc | cttctggtct | ggtgcctgag | ggaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttgggcaccc | aggcagtggg | 1980 |
| gcctaccaac | gtcagcctca | ccgtgactaa | catgccaccg | ggcaagcact | tccgggtaga | 2040 |
| cggcacctcc | gtgctgagag | gcttctcttt | catggagcca | gtgctgatag | cagtgcaacc | 2100 |
| cctctttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |
| ggggcagctt | ttatgtgcca | caccccctgg | ggccacggtg | gccagtgtcc | cccttagcct | 2280 |

FIG. 3A-2          SEQ ID NO: 5 cont.

```
gcaggtgggg ggtgcccagg tacctggttc ctggaccttc cagtacagag aagaccctgt 2340
cgtgctaagc atcagcccca actgtggcta catcaactcc cacatcacca tctgtggcca 2400
gcatctaact tcagcatggc acttagtgct gtcattccat gacgggctta gggcagtgga 2460
aagcaggtgt gagaggcagc ttccagagca gcagctgtgc cgccttcctg aatatgtggt 2520
ccgagacccc cagggatggg tggcagggaa tctgagtgcc cgaggggatg gagctgctgg 2580
ctttacactg cctggctttc gcttcctacc cccacccat ccacccagtg ccaacctagt 2640
tccactgaag cctgaggagc atgccattaa gtttgagctt ggccaggatg gtgcccatt 2700
gcaggtctgc gtagatgcac tccctgccat tgatggtctg gattccacca cttgtgtcca 2760
tggagcatcc ttctccgata gtgaagatga atcctgtgtg ccactgctgc ggaaagagtc 2820
catccagcta agggacctgg actctgcgct cttggctgag gtcaaggatg tgctgattcc 2880
ccatgagcgg gtggtcaccc acagtgaccg agtcattggc aaaggccact ttggagttgt 2940
ctaccacgga gaatacatag accaggccca gaatcgaatc caatgtgcca tcaagtcact 3000
aagtcgcatc acagagatgc agcaggtgga ggccttcctg cgagaggggc tgctcatgcg 3060
tggcctgaac cacccgaatg tgctggctct cattggtatc atgttgccac ctgagggcct 3120
gccccatgtg ctgctgccct atatgtgcca cggtgacctg ctccagttca tccgctcacc 3180
tcagcggaac cccaccgtga aggacctcat cagctttggc ctgcaggtag cccgcggcat 3240
ggagtacctg gcagagcaga agtttgtgca cagggacctg gctgcgcgga actgcatgct 3300
ggacgagtca ttcacagtca aggtggctga ctttggtttg gcccgcgaca tcctggacag 3360
ggagtactat agtgttcaac agcatcgcca cgctcgccta cctgtgaagt ggatggcgct 3420
ggagagcctg cagacctata gatttaccac caagtctgat gtggtaccaa gtgatgcagc 3480
aatgctggga ggcagaccca gcagtgcgac ccaccttcag agtactagtg ggggaggtgg 3540
agcagatagt gtctgcactg cttggggacc attatgtgca gctgccagca acctacatga 3600
acttgagcta accccaaggc tgcctctggg ccatgccagg ccagagcagt ggccctccac 3660
cttgttcctg ccctttaact ttcagaggca ataggtaaat gggcccatta ggtccctcac 3720
tccacagagt gagccagtga gggcagtcct gcaacatgta tttatggagt gcctgctgtg 3780
gaccctgtct tctgggcaca gtggactcag cagtgaccac accaacactg acccttgaac 3840
caataaagga acaaatgact attaaagcac aaaaaaaaaa                        3880
```

FIG. 3B-1    SEQ ID NO: 6

```
Met Glu Leu Leu Pro Pro Leu Pro Gln Ser Phe Leu Leu Leu Leu
                  5               10                  15
Leu Pro Ala Lys Pro Ala Ala Gly Glu Asp Trp Gln Cys Pro Arg Thr
            20                  25                  30
Pro Tyr Ala Ala Ser Arg Asp Phe Asp Val Lys Tyr Val Val Pro Ser
        35                  40                  45
Phe Ser Ala Gly Gly Leu Val Gln Ala Met Val Thr Tyr Glu Gly Asp
    50                  55                  60
Arg Asn Glu Ser Ala Val Phe Val Ala Ile Arg Asn Arg Leu His Val
65              70                  75                  80
Leu Gly Pro Asp Leu Lys Ser Val Gln Ser Leu Ala Thr Gly Pro Ala
            85                  90                  95
Gly Asp Pro Gly Cys Gln Thr Cys Ala Ala Cys Gly Pro Gly Pro His
            100             105             110
Gly Pro Pro Gly Asp Thr Asp Thr Lys Val Leu Val Leu Asp Pro Ala
        115             120             125
Leu Pro Ala Leu Val Ser Cys Gly Ser Ser Leu Gln Gly Arg Cys Phe
    130             135             140
Leu His Asp Leu Glu Pro Gln Gly Thr Ala Val His Leu Ala Ala Pro
145             150             155             160
Ala Cys Leu Phe Ser Ala His His Asn Arg Pro Asp Asp Cys Pro Asp
            165             170             175
Cys Val Ala Ser Pro Leu Gly Thr Arg Val Thr Val Val Glu Gln Gly
        180             185             190
Gln Ala Ser Tyr Phe Tyr Val Ala Ser Ser Leu Asp Ala Ala Val Ala
        195             200             205
Gly Ser Phe Ser Pro Arg Ser Val Ser Ile Arg Arg Leu Lys Ala Asp
    210             215             220
Ala Ser Gly Phe Ala Pro Gly Phe Val Ala Leu Ser Val Leu Pro Lys
225             230             235             240
His Leu Val Ser Tyr Ser Ile Glu Tyr Val His Ser Phe His Thr Gly
            245             250             255
Ala Phe Val Tyr Phe Leu Thr Val Gln Pro Ala Ser Val Thr Asp Asp
            260             265             270
Pro Ser Ala Leu His Thr Arg Leu Ala Arg Leu Ser Ala Thr Glu Pro
        275             280             285
Glu Leu Gly Asp Tyr Arg Glu Leu Val Leu Asp Cys Arg Phe Ala Pro
    290             295             300
Lys Arg Arg Arg Arg Gly Ala Pro Glu Gly Gly Gln Pro Tyr Pro Val
305             310             315             320
Leu Gln Val Ala His Ser Ala Pro Val Gly Ala Gln Leu Ala Thr Glu
            325             330             335
Leu Ser Ile Ala Glu Gly Gln Glu Val Leu Phe Gly Val Phe Val Thr
            340             345             350
Gly Lys Asp Gly Gly Pro Gly Val Gly Pro Asn Ser Val Val Cys Ala
        355             360             365
Phe Pro Ile Asp Leu Leu Asp Thr Leu Ile Asp Glu Gly Val Glu Arg
    370             375             380
Cys Cys Glu Ser Pro Val His Pro Gly Leu Arg Arg Gly Leu Asp Phe
385             390             395             400
Phe Gln Ser Pro Ser Phe Cys Pro Asn Pro Pro Gly Leu Glu Ala Leu
            405             410             415
Ser Pro Asn Thr Ser Cys Arg His Phe Pro Leu Leu Val Ser Ser Ser
            420             425             430
Phe Ser Arg Val Asp Leu Phe Asn Gly Leu Leu Gly Pro Val Gln Val
        435             440             445
Thr Ala Leu Tyr Val Thr Arg Leu Asp Asn Val Thr Val Ala His Met
    450             455             460
Gly Thr Met Asp Gly Arg Ile Leu Gln Val Glu Leu Val Arg Ser Leu
465             470             475             480
```

FIG. 3B-2  SEQ ID NO: 6 cont.

| | | | | | | | | | | | | | |
|---|---|---|---|---|---|---|---|---|---|---|---|---|---|
| Asn | Tyr | Leu | Leu | Tyr 485 | Val | Ser | Asn | Phe 490 | Ser | Leu | Gly | Asp | Ser 495 | Gly | Gln |
| Pro | Val | Gln | Arg 500 | Asp | Val | Ser | Arg 505 | Leu | Gly | Asp | His | Leu 510 | Leu | Phe | Ala |
| Ser | Gly | Asp 515 | Gln | Val | Phe | Gln | Val 520 | Pro | Ile | Arg | Gly | Pro 525 | Gly | Cys | Arg |
| His | Phe 530 | Leu | Thr | Cys | Gly | Arg 535 | Cys | Leu | Arg | Ala | Trp 540 | His | Phe | Met | Gly |
| Cys 545 | Gly | Trp | Cys | Gly | Asn 550 | Met | Cys | Gly | Gln | Gln 555 | Lys | Glu | Cys | Pro | Gly 560 |
| Ser | Trp | Gln | Gln | Asp 565 | His | Cys | Pro | Pro | Lys 570 | Leu | Thr | Glu | Phe | His 575 | Pro |
| His | Ser | Gly | Pro 580 | Leu | Arg | Gly | Ser | Thr 585 | Arg | Leu | Thr | Leu | Cys 590 | Gly | Ser |
| Asn | Phe | Tyr 595 | Leu | His | Pro | Ser | Gly 600 | Leu | Val | Pro | Glu | Gly 605 | Thr | His | Gln |
| Val | Thr 610 | Val | Gly | Gln | Ser | Pro 615 | Cys | Arg | Pro | Leu | Pro 620 | Lys | Asp | Ser | Ser |
| Lys 625 | Leu | Arg | Pro | Val | Pro 630 | Arg | Lys | Asp | Phe | Val 635 | Glu | Glu | Phe | Glu | Cys 640 |
| Glu | Leu | Glu | Pro | Leu 645 | Gly | Thr | Gln | Ala | Val 650 | Gly | Pro | Thr | Asn | Val 655 | Ser |
| Leu | Thr | Val | Thr 660 | Asn | Met | Pro | Pro | Gly 665 | Lys | His | Phe | Arg | Val 670 | Asp | Gly |
| Thr | Ser | Val 675 | Leu | Arg | Gly | Phe | Ser 680 | Phe | Met | Glu | Pro | Val 685 | Leu | Ile | Ala |
| Val | Gln 690 | Pro | Leu | Phe | Gly | Pro 695 | Arg | Ala | Gly | Gly | Thr 700 | Cys | Leu | Thr | Leu |
| Glu 705 | Gly | Gln | Ser | Leu | Ser 710 | Val | Gly | Thr | Ser | Arg 715 | Ala | Val | Leu | Val | Asn 720 |
| Gly | Thr | Glu | Cys | Leu 725 | Leu | Ala | Arg | Val | Ser 730 | Glu | Gly | Gln | Leu | Leu 735 | Cys |
| Ala | Thr | Pro | Pro 740 | Gly | Ala | Thr | Val | Ala 745 | Ser | Val | Pro | Leu | Ser 750 | Leu | Gln |
| Val | Gly | Gly 755 | Ala | Gln | Val | Pro | Gly 760 | Ser | Trp | Thr | Phe | Gln 765 | Tyr | Arg | Glu |
| Asp | Pro 770 | Val | Val | Leu | Ser | Ile 775 | Ser | Pro | Asn | Cys | Gly 780 | Tyr | Ile | Asn | Ser |
| His 785 | Ile | Thr | Ile | Cys | Gly 790 | Gln | His | Leu | Thr | Ser 795 | Ala | Trp | His | Leu | Val 800 |
| Leu | Ser | Phe | His | Asp 805 | Gly | Leu | Arg | Ala | Val 810 | Glu | Ser | Arg | Cys | Glu 815 | Arg |
| Gln | Leu | Pro | Glu 820 | Gln | Gln | Leu | Cys | Arg 825 | Leu | Pro | Glu | Tyr | Val 830 | Val | Arg |
| Asp | Pro | Gln 835 | Gly | Trp | Val | Ala | Gly 840 | Asn | Leu | Ser | Ala | Arg 845 | Gly | Asp | Gly |
| Ala | Ala 850 | Gly | Phe | Thr | Leu | Pro 855 | Gly | Phe | Arg | Phe | Leu 860 | Pro | Pro | Pro | His |
| Pro 865 | Pro | Ser | Ala | Asn | Leu 870 | Val | Pro | Leu | Lys | Pro 875 | Glu | Glu | His | Ala | Ile 880 |
| Lys | Phe | Glu | Leu | Gly 885 | Gln | Asp | Gly | Ala | Pro 890 | Leu | Gln | Val | Cys | Val 895 | Asp |
| Ala | Leu | Pro | Ala 900 | Ile | Asp | Gly | Leu | Asp 905 | Ser | Thr | Thr | Cys | Val 910 | His | Gly |
| Ala | Ser | Phe 915 | Ser | Asp | Ser | Glu | Asp 920 | Glu | Ser | Cys | Val | Pro 925 | Leu | Leu | Arg |
| Lys | Glu 930 | Ser | Ile | Gln | Leu | Arg 935 | Asp | Leu | Asp | Ser | Ala 940 | Leu | Leu | Ala | Glu |
| Val 945 | Lys | Asp | Val | Leu | Ile 950 | Pro | His | Glu | Arg | Val 955 | Val | Thr | His | Ser | Asp 960 |

FIG. 3B-3  SEQ ID NO: 6 cont.

```
Arg Val Ile Gly Lys Gly His Phe Gly Val Val Tyr His Gly Glu Tyr
            965                 970                 975
Ile Asp Gln Ala Gln Asn Arg Ile Gln Cys Ala Ile Lys Ser Leu Ser
            980                 985                 990
Arg Ile Thr Glu Met Gln Gln Val Glu Ala Phe Leu Arg Glu Gly Leu
            995            1000                1005
Leu Met Arg Gly Leu Asn His Pro Asn Val Leu Ala Leu Ile Gly Ile
        1010            1015                1020
Met Leu Pro Pro Glu Gly Leu Pro His Val Leu Leu Pro Tyr Met Cys
1025            1030                1035                    1040
His Gly Asp Leu Leu Gln Phe Ile Arg Ser Pro Gln Arg Asn Pro Thr
                1045                1050                1055
Val Lys Asp Leu Ile Ser Phe Gly Leu Gln Val Ala Arg Gly Met Glu
            1060                1065                1070
Tyr Leu Ala Glu Gln Lys Phe Val His Arg Asp Leu Ala Ala Arg Asn
            1075                1080                1085
Cys Met Leu Asp Glu Ser Phe Thr Val Lys Val Ala Asp Phe Gly Leu
        1090                1095                1100
Ala Arg Asp Ile Leu Asp Arg Glu Tyr Tyr Ser Val Gln Gln His Arg
1105                1110                1115                1120
His Ala Arg Leu Pro Val Lys Trp Met Ala Leu Glu Ser Leu Gln Thr
                1125                1130                1135
Tyr Arg Phe Thr Thr Lys Ser Asp Val Val Pro Ser Asp Ala Ala Met
            1140                1145                1150
Leu Gly Gly Arg Pro Ser Ser Ala Thr His Leu Gln Ser Thr Ser Gly
        1155                1160                1165
Gly Gly Gly Ala Asp Ser Val Cys Thr Ala Trp Gly Pro Leu Cys Ala
        1170                1175                1180
Ala Ala Ser Asn Leu His Glu Leu Glu Leu Thr Pro Arg Leu Pro Leu
1185                1190                1195                1200
Gly His Ala Arg Pro Glu Gln Trp Pro Ser Thr Leu Phe Leu Pro Phe
                1205                1210                1215
Asn Phe Gln Arg Gln
            1220
```

FIG. 3C-1  Coding Sequence (SEQ ID NO: 5 & 6)

```
atg gag ctc ctc ccg ccg ctg cct cag tcc ttc ctg ttg ctg ctg ctg   48
Met Glu Leu Leu Pro Pro Leu Pro Gln Ser Phe Leu Leu Leu Leu Leu
                 5               10                  15
ttg cct gcc aag ccc gcg gcg ggc gag gac tgg cag tgc ccg cgc acc   96
Leu Pro Ala Lys Pro Ala Ala Gly Glu Asp Trp Gln Cys Pro Arg Thr
             20              25                  30
ccc tac gcg gcc tct cgc gac ttt gac gtg aag tac gtg gtg ccc agc  144
Pro Tyr Ala Ala Ser Arg Asp Phe Asp Val Lys Tyr Val Val Pro Ser
         35              40                  45
ttc tcc gcc gga ggc ctg gta cag gcc atg gtg acc tac gag ggc gac  192
Phe Ser Ala Gly Gly Leu Val Gln Ala Met Val Thr Tyr Glu Gly Asp
     50              55                  60
aga aat gag agt gct gtg ttt gta gcc ata cgc aat cgc ctg cat gtg  240
Arg Asn Glu Ser Ala Val Phe Val Ala Ile Arg Asn Arg Leu His Val
 65              70                  75              80
ctt ggg cct gac ctg aag tct gtc cag agc ctg gcc acg ggc cct gct  288
Leu Gly Pro Asp Leu Lys Ser Val Gln Ser Leu Ala Thr Gly Pro Ala
                 85              90                  95
gga gac cct ggc tgc cag acg tgt gca gcc tgt ggc cca gga ccc cac  336
Gly Asp Pro Gly Cys Gln Thr Cys Ala Ala Cys Gly Pro Gly Pro His
             100             105                 110
ggc cct ccc ggt gac aca gac aca aag gtg ctg gtg ctg gat ccc gcg  384
Gly Pro Pro Gly Asp Thr Asp Thr Lys Val Leu Val Leu Asp Pro Ala
         115             120                 125
ctg cct gcg ctg gtc agt tgt ggc tcc agc ctg cag ggc cgc tgc ttc  432
Leu Pro Ala Leu Val Ser Cys Gly Ser Ser Leu Gln Gly Arg Cys Phe
     130             135                 140
ctg cat gac cta gag ccc caa ggg aca gcc gtg cat ctg gca gcg cca  480
Leu His Asp Leu Glu Pro Gln Gly Thr Ala Val His Leu Ala Ala Pro
145             150                 155             160
gcc tgc ctc ttc tca gcc cac cat aac cgg ccc gat gac tgc ccc gac  528
Ala Cys Leu Phe Ser Ala His His Asn Arg Pro Asp Asp Cys Pro Asp
                 165             170                 175
tgt gtg gcc agc cca ttg ggc acc cgt gta act gtg gtt gag caa ggc  576
Cys Val Ala Ser Pro Leu Gly Thr Arg Val Thr Val Val Glu Gln Gly
             180             185                 190
cag gcc tcc tat ttc tac gtg gca tcc tca ctg gac gca gcc gtg gct  624
Gln Ala Ser Tyr Phe Tyr Val Ala Ser Ser Leu Asp Ala Ala Val Ala
         195             200                 205
ggc agc ttc agc cca cgc tca gtg tct atc agg cgt ctc aag gct gac  672
Gly Ser Phe Ser Pro Arg Ser Val Ser Ile Arg Arg Leu Lys Ala Asp
     210             215                 220
gcc tcg gga ttc gca ccg ggc ttt gtg gcg ttg tca gtg ctg ccc aag  720
Ala Ser Gly Phe Ala Pro Gly Phe Val Ala Leu Ser Val Leu Pro Lys
225             230                 235             240
cat ctt gtc tcc tac agt att gaa tac gtg cac agc ttc cac acg gga  768
His Leu Val Ser Tyr Ser Ile Glu Tyr Val His Ser Phe His Thr Gly
                 245             250                 255
gcc ttc gta tac ttc ctg act gta cag ccg gcc agc gtg aca gat gat  816
Ala Phe Val Tyr Phe Leu Thr Val Gln Pro Ala Ser Val Thr Asp Asp
             260             265                 270
cct agt gcc ctg cac aca cgc ctg gca cgg ctt agc gcc act gag cca  864
Pro Ser Ala Leu His Thr Arg Leu Ala Arg Leu Ser Ala Thr Glu Pro
         275             280                 285
gag ttg ggt gac tat cgg gag ctg gtc ctc gac tgc aga ttt gct cca  912
Glu Leu Gly Asp Tyr Arg Glu Leu Val Leu Asp Cys Arg Phe Ala Pro
     290             295                 300
aaa cgc agg cgc cgg ggg gcc cca gaa ggc gga cag ccc tac cct gtg  960
Lys Arg Arg Arg Arg Gly Ala Pro Glu Gly Gly Gln Pro Tyr Pro Val
305             310                 315             320
```

FIG. 3C-2                  Coding Sequence (SEQ ID NO: 5 & 6) cont.

```
ctg cag gtg gcc cac tcc gct cca gtg ggt gcc caa ctt gcc act gag 1008
Leu Gln Val Ala His Ser Ala Pro Val Gly Ala Gln Leu Ala Thr Glu
            325                 330                 335
ctg agc atc gcc gag ggc cag gaa gta cta ttt ggg gtc ttt gtg act 1056
Leu Ser Ile Ala Glu Gly Gln Glu Val Leu Phe Gly Val Phe Val Thr
                340                 345                 350
ggc aag gat ggt ggt cct ggc gtg ggc ccc aac tct gtc gtc tgt gcc 1104
Gly Lys Asp Gly Gly Pro Gly Val Gly Pro Asn Ser Val Val Cys Ala
            355                 360                 365
ttc ccc att gac ctg ctg gac aca cta att gat gag ggt gtg gag cgc 1152
Phe Pro Ile Asp Leu Leu Asp Thr Leu Ile Asp Glu Gly Val Glu Arg
        370                 375                 380
tgt tgt gaa tcc cca gtc cat cca ggc ctc cgg cga ggc ctc gac ttc 1200
Cys Cys Glu Ser Pro Val His Pro Gly Leu Arg Arg Gly Leu Asp Phe
385                 390                 395                 400
ttc cag tcg ccc agt ttt tgc ccc aac ccg cct ggc ctg gaa gcc ctc 1248
Phe Gln Ser Pro Ser Phe Cys Pro Asn Pro Pro Gly Leu Glu Ala Leu
                405                 410                 415
agc ccc aac acc agc tgc cgc cac ttc cct ctg ctg gtc agt agc agc 1296
Ser Pro Asn Thr Ser Cys Arg His Phe Pro Leu Leu Val Ser Ser Ser
            420                 425                 430
ttc tca cgt gtg gac cta ttc aat ggg ctg ttg gga cca gta cag gtc 1344
Phe Ser Arg Val Asp Leu Phe Asn Gly Leu Leu Gly Pro Val Gln Val
        435                 440                 445
act gca ttg tat gtg aca cgc ctt gac aac gtc aca gtg gca cac atg 1392
Thr Ala Leu Tyr Val Thr Arg Leu Asp Asn Val Thr Val Ala His Met
    450                 455                 460
ggc aca atg gat ggg cgt atc ctg cag gtg gag ctg gtc agg tca cta 1440
Gly Thr Met Asp Gly Arg Ile Leu Gln Val Glu Leu Val Arg Ser Leu
465                 470                 475                 480
aac tac ttg ctg tat gtg tcc aac ttc tca ctg ggt gac agt ggg cag 1488
Asn Tyr Leu Leu Tyr Val Ser Asn Phe Ser Leu Gly Asp Ser Gly Gln
                485                 490                 495
ccc gtg cag cgg gat gtc agt cgt ctt ggg gac cac cta ctc ttt gcc 1536
Pro Val Gln Arg Asp Val Ser Arg Leu Gly Asp His Leu Leu Phe Ala
            500                 505                 510
tct ggg gac cag gtt ttc cag gta cct atc cga ggc cct ggc tgc cgc 1584
Ser Gly Asp Gln Val Phe Gln Val Pro Ile Arg Gly Pro Gly Cys Arg
        515                 520                 525
cac ttc ctg acc tgt ggg cgt tgc cta agg gca tgg cat ttc atg ggc 1632
His Phe Leu Thr Cys Gly Arg Cys Leu Arg Ala Trp His Phe Met Gly
530                 535                 540
tgt ggc tgg tgt ggg aac atg tgc ggc cag cag aag gag tgt cct ggc 1680
Cys Gly Trp Cys Gly Asn Met Cys Gly Gln Gln Lys Glu Cys Pro Gly
545                 550                 555                 560
tcc tgg caa cag gac cac tgc cca cct aag ctt act gag ttc cac ccc 1728
Ser Trp Gln Gln Asp His Cys Pro Pro Lys Leu Thr Glu Phe His Pro
                565                 570                 575
cac agt gga cct cta agg ggc agt aca agg ctg acc ctg tgt ggc tcc 1776
His Ser Gly Pro Leu Arg Gly Ser Thr Arg Leu Thr Leu Cys Gly Ser
            580                 585                 590
aac ttc tac ctt cac cct tct ggt ctg gtg cct gag gga acc cat cag 1824
Asn Phe Tyr Leu His Pro Ser Gly Leu Val Pro Glu Gly Thr His Gln
        595                 600                 605
gtc act gtg ggc caa agt ccc tgc cgg cca ctg ccc aag gac agc tca 1872
Val Thr Val Gly Gln Ser Pro Cys Arg Pro Leu Pro Lys Asp Ser Ser
    610                 615                 620
aaa ctc aga cca gtg ccc cgg aaa gac ttt gta gag gag ttt gag tgt 1920
Lys Leu Arg Pro Val Pro Arg Lys Asp Phe Val Glu Glu Phe Glu Cys
625                 630                 635                 640
```

FIG. 3C-3  Coding Sequence (SEQ ID NO: 5 & 6) cont.

```
gaa  ctg  gag  ccc  ttg  ggc  acc  cag  gca  gtg  ggg  cct  acc  aac  gtc  agc  1968
Glu  Leu  Glu  Pro  Leu  Gly  Thr  Gln  Ala  Val  Gly  Pro  Thr  Asn  Val  Ser
               645                      650                     655
ctc  acc  gtg  act  aac  atg  cca  ccg  ggc  aag  cac  ttc  cgg  gta  gac  ggc  2016
Leu  Thr  Val  Thr  Asn  Met  Pro  Pro  Gly  Lys  His  Phe  Arg  Val  Asp  Gly
              660                      665                      670
acc  tcc  gtg  ctg  aga  ggc  ttc  tct  ttc  atg  gag  cca  gtg  ctg  ata  gca  2064
Thr  Ser  Val  Leu  Arg  Gly  Phe  Ser  Phe  Met  Glu  Pro  Val  Leu  Ile  Ala
         675                      680                     685
gtg  caa  ccc  ctc  ttt  ggc  cca  cgg  gca  gga  ggc  acc  tgt  ctc  act  ctt  2112
Val  Gln  Pro  Leu  Phe  Gly  Pro  Arg  Ala  Gly  Gly  Thr  Cys  Leu  Thr  Leu
     690                      695                     700
gaa  ggc  cag  agt  ctg  tct  gta  ggc  acc  agc  cgg  gct  gtg  ctg  gtc  aat  2160
Glu  Gly  Gln  Ser  Leu  Ser  Val  Gly  Thr  Ser  Arg  Ala  Val  Leu  Val  Asn
705                      710                     715                     720
ggg  act  gag  tgt  ctg  cta  gca  cgg  gtc  agt  gag  ggg  cag  ctt  tta  tgt  2208
Gly  Thr  Glu  Cys  Leu  Leu  Ala  Arg  Val  Ser  Glu  Gly  Gln  Leu  Leu  Cys
                    725                      730                     735
gcc  aca  ccc  cct  ggg  gcc  acg  gtg  gcc  agt  gtc  ccc  ctt  agc  ctg  cag  2256
Ala  Thr  Pro  Pro  Gly  Ala  Thr  Val  Ala  Ser  Val  Pro  Leu  Ser  Leu  Gln
               740                      745                     750
gtg  ggg  ggt  gcc  cag  gta  cct  ggt  tcc  tgg  acc  ttc  cag  tac  aga  gaa  2304
Val  Gly  Gly  Ala  Gln  Val  Pro  Gly  Ser  Trp  Thr  Phe  Gln  Tyr  Arg  Glu
          755                      760                     765
gac  cct  gtc  gtg  cta  agc  atc  agc  ccc  aac  tgt  ggc  tac  atc  aac  tcc  2352
Asp  Pro  Val  Val  Leu  Ser  Ile  Ser  Pro  Asn  Cys  Gly  Tyr  Ile  Asn  Ser
     770                      775                     780
cac  atc  acc  atc  tgt  ggc  cag  cat  cta  act  tca  gca  tgg  cac  tta  gtg  2400
His  Ile  Thr  Ile  Cys  Gly  Gln  His  Leu  Thr  Ser  Ala  Trp  His  Leu  Val
785                      790                     795                     800
ctg  tca  ttc  cat  gac  ggg  ctt  agg  gca  gtg  gaa  agc  agg  tgt  gag  agg  2448
Leu  Ser  Phe  His  Asp  Gly  Leu  Arg  Ala  Val  Glu  Ser  Arg  Cys  Glu  Arg
                    805                      810                     815
cag  ctt  cca  gag  cag  cag  ctg  tgc  cgc  ctt  cct  gaa  tat  gtg  gtc  cga  2496
Gln  Leu  Pro  Glu  Gln  Gln  Leu  Cys  Arg  Leu  Pro  Glu  Tyr  Val  Val  Arg
               820                      825                     830
gac  ccc  cag  gga  tgg  gtg  gca  ggg  aat  ctg  agt  gcc  cga  ggg  gat  gga  2544
Asp  Pro  Gln  Gly  Trp  Val  Ala  Gly  Asn  Leu  Ser  Ala  Arg  Gly  Asp  Gly
          835                      840                     845
gct  gct  ggc  ttt  aca  ctg  cct  ggc  ttt  cgc  ttc  cta  ccc  cca  ccc  cat  2592
Ala  Ala  Gly  Phe  Thr  Leu  Pro  Gly  Phe  Arg  Phe  Leu  Pro  Pro  Pro  His
     850                      855                     860
cca  ccc  agt  gcc  aac  cta  gtt  cca  ctg  aag  cct  gag  gag  cat  gcc  att  2640
Pro  Pro  Ser  Ala  Asn  Leu  Val  Pro  Leu  Lys  Pro  Glu  Glu  His  Ala  Ile
865                      870                     875                     880
aag  ttt  gag  ctt  ggc  cag  gat  ggt  gcc  cca  ttg  cag  gtc  tgc  gta  gat  2688
Lys  Phe  Glu  Leu  Gly  Gln  Asp  Gly  Ala  Pro  Leu  Gln  Val  Cys  Val  Asp
                    885                      890                     895
gca  ctc  cct  gcc  att  gat  ggt  ctg  gat  tcc  act  tgt  gtc  cat  gga  2736
Ala  Leu  Pro  Ala  Ile  Asp  Gly  Leu  Asp  Ser  Thr  Thr  Cys  Val  His  Gly
               900                      905                     910
gca  tcc  ttc  tcc  gat  agt  gaa  gat  gaa  tcc  tgt  gtg  cca  ctg  ctg  cgg  2784
Ala  Ser  Phe  Ser  Asp  Ser  Glu  Asp  Glu  Ser  Cys  Val  Pro  Leu  Leu  Arg
          915                      920                     925
aaa  gag  tcc  atc  cag  cta  agg  gac  ctg  gac  tct  gcg  ctc  ttg  gct  gag  2832
Lys  Glu  Ser  Ile  Gln  Leu  Arg  Asp  Leu  Asp  Ser  Ala  Leu  Leu  Ala  Glu
     930                      935                     940
gtc  aag  gat  gtg  ctg  att  ccc  cat  gag  cgg  gtg  gtc  acc  cac  agt  gac  2880
Val  Lys  Asp  Val  Leu  Ile  Pro  His  Glu  Arg  Val  Val  Thr  His  Ser  Asp
945                      950                     955                     960
```

FIG. 3C-4  Coding Sequence (SEQ ID NO: 5 & 6) cont.

```
cga gtc att ggc aaa ggc cac ttt gga gtt gtc tac cac gga gaa tac 2928
Arg Val Ile Gly Lys Gly His Phe Gly Val Val Tyr His Gly Glu Tyr
            965                     970                 975
ata gac cag gcc cag aat cga atc caa tgt gcc atc aag tca cta agt 2976
Ile Asp Gln Ala Gln Asn Arg Ile Gln Cys Ala Ile Lys Ser Leu Ser
                980                 985                 990
cgc atc aca gag atg cag cag gtg gag gcc ttc ctg cga gag ggg ctg 3024
Arg Ile Thr Glu Met Gln Gln Val Glu Ala Phe Leu Arg Glu Gly Leu
            995                     1000                1005
ctc atg cgt ggc ctg aac cac ccg aat gtg ctg gct ctc att ggt atc 3072
Leu Met Arg Gly Leu Asn His Pro Asn Val Leu Ala Leu Ile Gly Ile
        1010                    1015                1020
atg ttg cca cct gag ggc ctg ccc cat gtg ctg ctg ccc tat atg tgc 3120
Met Leu Pro Pro Glu Gly Leu Pro His Val Leu Leu Pro Tyr Met Cys
1025                    1030                    1035            1040
cac ggt gac ctg ctc cag ttc atc cgc tca cct cag cgg aac ccc acc 3168
His Gly Asp Leu Leu Gln Phe Ile Arg Ser Pro Gln Arg Asn Pro Thr
                    1045                    1050                1055
gtg aag gac ctc atc agc ttt ggc ctg cag gta gcc cgc ggc atg gag 3216
Val Lys Asp Leu Ile Ser Phe Gly Leu Gln Val Ala Arg Gly Met Glu
                1060                    1065                1070
tac ctg gca gag cag aag ttt gtg cac agg gac ctg gct gcg cgg aac 3264
Tyr Leu Ala Glu Gln Lys Phe Val His Arg Asp Leu Ala Ala Arg Asn
            1075                    1080                1085
tgc atg ctg gac gag tca ttc aca gtc aag gtg gct gac ttt ggt ttg 3312
Cys Met Leu Asp Glu Ser Phe Thr Val Lys Val Ala Asp Phe Gly Leu
        1090                    1095                1100
gcc cgc gac atc ctg gac agg gag tac tat agt gtt caa cag cat cgc 3360
Ala Arg Asp Ile Leu Asp Arg Glu Tyr Tyr Ser Val Gln Gln His Arg
1105                    1110                    1115            1120
cac gct cgc cta cct gtg aag tgg atg gcg ctg gag agc ctg cag acc 3408
His Ala Arg Leu Pro Val Lys Trp Met Ala Leu Glu Ser Leu Gln Thr
                    1125                    1130                1135
tat aga ttt acc acc aag tct gat gtg gta cca agt gat gca gca atg 3456
Tyr Arg Phe Thr Thr Lys Ser Asp Val Val Pro Ser Asp Ala Ala Met
                1140                    1145                1150
ctg gga ggc aga ccc agc agt gcg acc cac ctt cag agt act agt ggg 3504
Leu Gly Gly Arg Pro Ser Ser Ala Thr His Leu Gln Ser Thr Ser Gly
            1155                    1160                    1165
gga ggt gga gca gat agt gtc tgc act gct tgg gga cca tta tgt gca 3552
Gly Gly Gly Ala Asp Ser Val Cys Thr Ala Trp Gly Pro Leu Cys Ala
        1170                    1175                    1180
gct gcc agc aac cta cat gaa ctt gag cta acc cca agg ctg cct ctg 3600
Ala Ala Ser Asn Leu His Glu Leu Glu Leu Thr Pro Arg Leu Pro Leu
1185                    1190                    1195            1200
ggc cat gcc agg cca gag cag tgg ccc tcc acc ttg ctg ccc ttt 3648
Gly His Ala Arg Pro Glu Gln Trp Pro Ser Thr Leu Phe Leu Pro Phe
                    1205                    1210                1215
aac ttt cag agg caa                                             3663
Asn Phe Gln Arg Gln
            1220
```

FIG. 4A-1      SEQ ID NO: 7

| | | | | | | |
|---|---|---|---|---|---|---|
| GGATCCTCTA | GGGTCCCAGC | TCGCCTCGAT | GGAGCTCCTC | CCGCCGCTGC | CTCAGTCCTT | 60 |
| CCTGTTGCTG | CTGCTGTTGC | CTGCCAAGCC | CGCGGCGGGC | GAGGACTGGC | AGTGCCCGCG | 120 |
| CACCCCCTAC | GCGGCCTCTC | GCGACTTTGA | CGTGAAGTAC | GTGGTGCCCA | GCTTCTCCGC | 180 |
| CGGAGGCCTG | GTACAGGCCA | TGGTGACCTA | CGAGGGCGAC | AGAAATGAGA | GTGCTGTGTT | 240 |
| TGTAGCCATA | CGCAATCGCC | TGCATGTGCT | TGGGCCTGAC | CTGAAGTCTG | TCCAGAGCCT | 300 |
| GGCCACGGGC | CCTGCTGGAG | ACCCTGGCTG | CCAGACGTGT | GCAGCCTGTG | GCCCAGGACC | 360 |
| CCACGGCCCT | CCCGGTGACA | CAGACACAAA | GGTGCTGGTG | CTGGATCCCG | CGCTGCCTGC | 420 |
| GCTGGTCAGT | TGTGGCTCCA | GCCTGCAGGG | CCGCTGCTTC | CTGCATGACC | TAGAGCCCCA | 480 |
| AGGGACAGCC | GTGCATCTGG | CAGCGCCAGC | CTGCCTCTTC | TCAGCCCACC | ATAACCGGCC | 540 |
| CGATGACTGC | CCCGACTGTG | TGGCCAGCCC | ATTGGGCACC | CGTGTAACTG | TGGTTGAGCA | 600 |
| AGGCCAGGCC | TCCTATTTCT | ACGTGGCATC | CTCACTGGAC | GCAGCCGTGG | CTGGCAGCTT | 660 |
| CAGCCCACGC | TCAGTGTCTA | TCAGGCGTCT | CAAGGCTGAC | GCCTCGGGAT | TCGCACCGGG | 720 |
| CTTTGTGGCG | TTGTCAGTGC | TGCCCAAGCA | TCTTGTCTCC | TACAGTATTG | AATACGTGCA | 780 |
| CAGCTTCCAC | ACGGGAGCCT | TCGTATACTT | CCTGACTGTA | CAGCCGGCCA | GCGTGACAGA | 840 |
| TGATCCTAGT | GCCCTGCACA | CACGCCTGGC | ACGGCTTAGC | GCCACTGAGC | CAGAGTTGGG | 900 |
| TGACTATCGG | GAGCTGGTCC | TCGACTGCAG | ATTTGCTCCA | AAACGCAGGC | GCCGGGGGGC | 960 |
| CCCAGAAGGC | GGACAGCCCT | ACCCTGTGCT | GCAGGTGGCC | CACTCCGCTC | CAGTGGGTGC | 1020 |
| CCAACTTGCC | ACTGAGCTGA | GCATCGCCGA | GGGCCAGGAA | GTACTATTTG | GGGTCTTTGT | 1080 |
| GACTGGCAAG | GATGGTGGTC | CTGGCGTGGG | CCCCAACTCT | GTCGTCTGTG | CCTTCCCCAT | 1140 |
| TGACCTGCTG | GACACACTAA | TTGATGAGGG | TGTGGAGCGC | TGTTGTGAAT | CCCCAGTCCA | 1200 |
| TCCAGGCCTC | CGGCGAGGCC | TCGACTTCTT | CCAGTCGCCC | AGTTTTGCC | CCAACCCGCC | 1260 |
| TGGCCTGGAA | GCCCTCAGCC | CCAACACCAG | CTGCCGCCAC | TTCCCTCTGC | TGGTCAGTAG | 1320 |
| CAGCTTCTCA | CGTGTGGACC | TATTCAATGG | GCTGTTGGGA | CCAGTACAGG | TCACTGCATT | 1380 |
| GTATGTGACA | CGCCTTGACA | ACGTCACAGT | GGCACACATG | GGCACAATGG | ATGGGCGTAT | 1440 |
| CCTGCAGGTG | GAGCTGGTCA | GGTCACTAAA | CTACTTGCTG | TATGTGTCCA | ACTTCTCACT | 1500 |
| GGGTGACAGT | GGGCAGCCCG | TGCAGCGGGA | TGTCAGTCGT | CTTGGGGACC | ACCTACTCTT | 1560 |
| TGCCTCTGGG | GACCAGGTTT | TCCAGGTACC | TATCCGAGGC | CCTGGCTGCC | GCCACTTCCT | 1620 |
| GACCTGTGGG | CGTTGCCTAA | GGGCATGGCA | TTTCATGGGC | TGTGGCTGGT | GTGGGAACAT | 1680 |
| GTGCGGCCAG | CAGAAGGAGT | GTCCTGGCTC | CTGGCAACAG | GACCACTGCC | CACCTAAGCT | 1740 |
| TACTGAGTTC | CACCCCCACA | GTGGACCTCT | AAGGGGCAGT | ACAAGGCTGA | CCCTGTGTGG | 1800 |
| CTCCAACTTC | TACCTTCACC | CTTCTGGTCT | GGTGCCTGAG | GGAACCCATC | AGGTCACTGT | 1860 |
| GGGCCAAAGT | CCCTGCCGGC | CACTGCCCAA | GGACAGCTCA | AAACTCAGAC | CAGTGCCCCG | 1920 |
| GAAAGACTTT | GTAGAGGAGT | TGAGTGTGA | ACTGGAGCCC | TTGGGCACCC | AGGCAGTGGG | 1980 |
| GCCTACCAAC | GTCAGCCTCA | CCGTGACTAA | CATGCCACCG | GGCAAGCACT | TCCGGGTAGA | 2040 |
| CGGCACCTCC | GTGCTGAGAG | GCTTCTCTTT | CATGGAGCCA | GTGCTGATAG | CAGTGCAACC | 2100 |
| CCTCTTTGGC | CCACGGGCAG | GAGGCACCTG | TCTCACTCTT | GAAGGCCAGA | GTCTGTCTGT | 2160 |
| AGGCACCAGC | CGGGCTGTGC | TGGTCAATGG | GACTGAGTGT | CTGCTAGCAC | GGGTCAGTGA | 2220 |
| GGGGCAGCTT | TTATGTGCCA | CACCCCTGG | GGCCACGGTG | GCCAGTGTCC | CCCTTAGCCT | 2280 |

FIG. 4A-2  SEQ ID NO: 7 cont.

```
GCAGGTGGGG  GGTGCCCAGG  TACCTGGTTC  CTGGACCTTC  CAGTACAGAG  AAGACCCTGT   2340
CGTGCTAAGC  ATCAGCCCCA  ACTGTGGCTA  CATCAACTCC  CACATCACCA  TCTGTGGCCA   2400
GCATCTAACT  TCAGCATGGC  ACTTAGTGCT  GTCATTCCAT  GACGGGCTTA  GGGCAGTGGA   2460
AAGCAGGTGT  GAGAGGCAGC  TTCCAGAGCA  GCAGCTGTGC  CGCCTTCCTG  AATATGTGGT   2520
CCGAGACCCC  CAGGGATGGG  TGGCAGGGAA  TCTGAGTGCC  CGAGGGGATG  GAGCTGCTGG   2580
CTTTACACTG  CCTGGCTTTC  GCTTCCTACC  CCCACCCCAT  CCACCCAGTG  CCAACCTAGT   2640
TCCACTGAAG  CCTGAGGAGC  ATGCCATTAA  GTTTGAGGTC  TGCGTAGATG  CACTCCCTGC   2700
CATTGATGGT  CTGGATTCCA  CCACTTGTGT  CCATGGAGCA  TCCTTCTCCG  ATAGTGAAGA   2760
TGAATCCTGT  GTGCCACTGC  TGCGGAAAGA  GTCCATCCAG  CTAAGGGACC  TGGACTCTGC   2820
GCTCTTGGCT  GAGGTCAAGG  ATGTGCTGAT  TCCCCATGAG  CGGGTGGTCA  CCCACAGTGA   2880
CCGAGTCATT  GGCAAAGGCC  ACTTTGGAGT  TGTCTACCAC  GGAGAATACA  TAGACCAGGC   2940
CCAGAATCGA  ATCCAATGTG  CCATCAAGTC  ACTAAGTCGC  ATCACAGAGA  TGCAGCAGGT   3000
GGAGGCCTTC  CTGCGAGAGG  GGCTGCTCAT  GCGTGGCCTG  AACCACCCGA  ATGTGCTGGC   3060
TCTCATTGGT  ATCATGTTGC  CACCTGAGGG  CCTGCCCCAT  GTGCTGCTGC  CCTATATGTG   3120
CCACGGTGAC  CTGCTCCAGT  TCATCCGCTC  ACCTCAGCGG  AACCCCACCG  TGAAGGACCT   3180
CATCAGCTTT  GGCCTGCAGG  TAGCCCGCGG  CATGGAGTAC  CTGGCAGAGC  AGAAGTTTGT   3240
GCACAGGGAC  CTGGCTGCGC  GGAACTGCAT  GCTGGACGAG  TCATTCACAG  TCAAGGTGGC   3300
TGACTTTGGT  TTGGCCCGCG  ACATCCTGGA  CAGGGAGTAC  TATAGTGTTC  AACAGCATCG   3360
CCACGCTCGC  CTACCTGTGA  AGTGGATGGC  GCTGGAGAGC  CTGCAGACCT  ATAGATTTAC   3420
CACCAAGTCT  GATGTGGTAC  CAAGTGATGC  AGCAATGCTG  GGAGGCAGAC  CCAGCAGTGC   3480
GACCCACCTT  CAGAGTACTA  GTGGGGGAGG  TGGAGCAGAT  AGTGTCTGCA  CTGCTTGGGG   3540
ACCATTATGT  GCAGCTGCCA  GCAACCTACA  TGAACTTGAG  CTAACCCCAA  GGCTGCCTCT   3600
GGGCCATGCC  AGGCCAGAGC  AGTGGCCCTC  CACCTTGTTC  CTGCCCTTTA  ACTTTCAGAG   3660
GCAATAGGTA  AATGGGCCCA  TTAGGTCCCT  CACTCCACAG  AGTGAGCCAG  TGAGGGCAGT   3720
CCTGCAACAT  GTATTTATGG  AGTGCCTGCT  GTGGACCCTG  TCTTCTGGGC  ACAGTGGACT   3780
CAGCAGTGAC  CACACCAACA  CTGACCCTTG  AACCAATAAA  GGAACAAATG  ACTATTAAAG   3840
CACAAAAAAA  AAA                                                         3853
```

FIG. 4B-1 SEQ ID NO: 8

| | | | | | | | | | | | | | | |
|---|---|---|---|---|---|---|---|---|---|---|---|---|---|---|
| Met | Glu | Leu | Leu | Pro 5 | Pro | Leu | Pro | Gln | Ser 10 | Phe | Leu | Leu | Leu 15 | Leu |
| Leu | Pro | Ala | Lys 20 | Pro | Ala | Ala | Gly | Glu 25 | Asp | Trp | Gln | Cys | Pro 30 | Arg | Thr |
| Pro | Tyr | Ala 35 | Ala | Ser | Arg | Asp | Phe 40 | Asp | Val | Lys | Tyr | Val 45 | Val | Pro | Ser |
| Phe | Ser 50 | Ala | Gly | Gly | Leu | Val 55 | Gln | Ala | Met | Val | Thr 60 | Tyr | Glu | Gly | Asp |
| Arg 65 | Asn | Glu | Ser | Ala | Val 70 | Phe | Val | Ala | Ile | Arg 75 | Asn | Arg | Leu | His | Val 80 |
| Leu | Gly | Pro | Asp | Leu 85 | Lys | Ser | Val | Gln | Ser 90 | Leu | Ala | Thr | Gly | Pro 95 | Ala |
| Gly | Asp | Pro | Gly 100 | Cys | Gln | Thr | Cys | Ala 105 | Ala | Cys | Gly | Pro | Gly 110 | Pro | His |
| Gly | Pro | Pro 115 | Gly | Asp | Thr | Asp | Thr 120 | Lys | Val | Leu | Val | Leu 125 | Asp | Pro | Ala |
| Leu | Pro 130 | Ala | Leu | Val | Ser | Cys 135 | Gly | Ser | Ser | Leu | Gln 140 | Gly | Arg | Cys | Phe |
| Leu 145 | His | Asp | Leu | Glu | Pro 150 | Gln | Gly | Thr | Ala | Val 155 | His | Leu | Ala | Ala | Pro 160 |
| Ala | Cys | Leu | Phe | Ser 165 | Ala | His | His | Asn | Arg 170 | Pro | Asp | Asp | Cys | Pro 175 | Asp |
| Cys | Val | Ala | Ser 180 | Pro | Leu | Gly | Thr | Arg 185 | Val | Thr | Val | Val | Glu 190 | Gln | Gly |
| Gln | Ala | Ser 195 | Tyr | Phe | Tyr | Val | Ala 200 | Ser | Ser | Leu | Asp | Ala 205 | Ala | Val | Ala |
| Gly | Ser 210 | Phe | Ser | Pro | Arg | Ser 215 | Val | Ser | Ile | Arg | Arg 220 | Leu | Lys | Ala | Asp |
| Ala 225 | Ser | Gly | Phe | Ala | Pro 230 | Gly | Phe | Val | Ala | Leu 235 | Ser | Val | Leu | Pro | Lys 240 |
| His | Leu | Val | Ser | Tyr 245 | Ser | Ile | Glu | Tyr | Val 250 | His | Ser | Phe | His | Thr 255 | Gly |
| Ala | Phe | Val | Tyr | Phe 260 | Leu | Thr | Val | Gln | Pro 265 | Ala | Ser | Val | Thr 270 | Asp | Asp |
| Pro | Ser | Ala 275 | Leu | His | Thr | Arg | Leu 280 | Ala | Arg | Leu | Ser | Ala 285 | Thr | Glu | Pro |
| Glu | Leu 290 | Gly | Asp | Tyr | Arg | Glu 295 | Leu | Val | Leu | Asp | Cys 300 | Arg | Phe | Ala | Pro |
| Lys 305 | Arg | Arg | Arg | Arg | Gly 310 | Ala | Pro | Glu | Gly | Gly 315 | Gln | Pro | Tyr | Pro | Val 320 |
| Leu | Gln | Val | Ala | His 325 | Ser | Ala | Pro | Val | Gly 330 | Ala | Gln | Leu | Ala | Thr 335 | Glu |
| Leu | Ser | Ile | Ala 340 | Glu | Gly | Gln | Glu | Val 345 | Leu | Phe | Gly | Val | Phe 350 | Val | Thr |
| Gly | Lys | Asp 355 | Gly | Gly | Pro | Gly | Val 360 | Gly | Pro | Asn | Ser | Val 365 | Val | Cys | Ala |
| Phe | Pro 370 | Ile | Asp | Leu | Leu | Asp 375 | Thr | Leu | Ile | Asp | Glu 380 | Gly | Val | Glu | Arg |
| Cys 385 | Cys | Glu | Ser | Pro | Val 390 | His | Pro | Gly | Leu | Arg 395 | Arg | Gly | Leu | Asp | Phe 400 |
| Phe | Gln | Ser | Pro | Ser 405 | Phe | Cys | Pro | Asn | Pro 410 | Pro | Gly | Leu | Glu | Ala 415 | Leu |
| Ser | Pro | Asn | Thr 420 | Ser | Cys | Arg | His | Phe 425 | Pro | Leu | Leu | Val | Ser 430 | Ser | Ser |
| Phe | Ser | Arg 435 | Val | Asp | Leu | Phe | Asn 440 | Gly | Leu | Leu | Gly | Pro 445 | Val | Gln | Val |
| Thr | Ala 450 | Leu | Tyr | Val | Thr | Arg 455 | Leu | Asp | Asn | Val | Thr 460 | Val | Ala | His | Met |
| Gly 465 | Thr | Met | Asp | Gly | Arg 470 | Ile | Leu | Gln | Val | Glu 475 | Leu | Val | Arg | Ser | Leu 480 |

FIG. 4B-2                 SEQ ID NO: 8 cont.

```
Asn Tyr Leu Leu Tyr Val Ser Asn Phe Ser Leu Gly Asp Ser Gly Gln
                485                 490                 495
Pro Val Gln Arg Asp Val Ser Arg Leu Gly Asp His Leu Leu Phe Ala
            500                 505                 510
Ser Gly Asp Gln Val Phe Gln Val Pro Ile Arg Gly Pro Gly Cys Arg
            515                 520                 525
His Phe Leu Thr Cys Gly Arg Cys Leu Arg Ala Trp His Phe Met Gly
        530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
        595                 600                 605
Val Thr Val Gly Gln Ser Pro Cys Arg Pro Leu Pro Lys Asp Ser Ser
    610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
            660                 665                 670
Thr Ser Val Leu Arg Gly Phe Ser Phe Met Glu Pro Val Leu Ile Ala
        675                 680                 685
Val Gln Pro Leu Phe Gly Pro Arg Ala Gly Gly Thr Cys Leu Thr Leu
    690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
            740                 745                 750
Val Gly Gly Ala Gln Val Pro Gly Ser Trp Thr Phe Gln Tyr Arg Glu
        755                 760                 765
Asp Pro Val Val Leu Ser Ile Ser Pro Asn Cys Gly Tyr Ile Asn Ser
    770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
Asp Pro Gln Gly Trp Val Ala Gly Asn Leu Ser Ala Arg Gly Asp Gly
        835                 840                 845
Ala Ala Gly Phe Thr Leu Pro Gly Phe Arg Phe Leu Pro Pro Pro His
    850                 855                 860
Pro Pro Ser Ala Asn Leu Val Pro Leu Lys Pro Glu Glu His Ala Ile
865                 870                 875                 880
Lys Phe Glu Val Cys Val Asp Ala Leu Pro Ala Ile Asp Gly Leu Asp
                885                 890                 895
Ser Thr Thr Cys Val His Gly Ala Ser Phe Ser Asp Ser Glu Asp Glu
            900                 905                 910
Ser Cys Val Pro Leu Leu Arg Lys Glu Ser Ile Gln Leu Arg Asp Leu
        915                 920                 925
Asp Ser Ala Leu Leu Ala Glu Val Lys Asp Val Leu Ile Pro His Glu
    930                 935                 940
Arg Val Val Thr His Ser Asp Arg Val Ile Gly Lys Gly His Phe Gly
945                 950                 955                 960
```

FIG. 4B-3                                     SEQ ID NO: 8 cont.

```
Val  Val  Tyr  His  Gly  Glu  Tyr  Ile  Asp  Gln  Ala  Gln  Asn  Arg  Ile  Gln
               965                      970                           975
Cys  Ala  Ile  Lys  Ser  Leu  Ser  Arg  Ile  Thr  Glu  Met  Gln  Gln  Val  Glu
               980                      985                           990
Ala  Phe  Leu  Arg  Glu  Gly  Leu  Leu  Met  Arg  Gly  Leu  Asn  His  Pro  Asn
          995                      1000                     1005
Val  Leu  Ala  Leu  Ile  Gly  Ile  Met  Leu  Pro  Pro  Glu  Gly  Leu  Pro  His
     1010                     1015                     1020
Val  Leu  Leu  Pro  Tyr  Met  Cys  His  Gly  Asp  Leu  Leu  Gln  Phe  Ile  Arg
1025                     1030                     1035                     1040
Ser  Pro  Gln  Arg  Asn  Pro  Thr  Val  Lys  Asp  Leu  Ile  Ser  Phe  Gly  Leu
               1045                     1050                          1055
Gln  Val  Ala  Arg  Gly  Met  Glu  Tyr  Leu  Ala  Glu  Gln  Lys  Phe  Val  His
               1060                     1065                          1070
Arg  Asp  Leu  Ala  Ala  Arg  Asn  Cys  Met  Leu  Asp  Glu  Ser  Phe  Thr  Val
          1075                     1080                     1085
Lys  Val  Ala  Asp  Phe  Gly  Leu  Ala  Arg  Asp  Ile  Leu  Asp  Arg  Glu  Tyr
     1090                     1095                     1100
Tyr  Ser  Val  Gln  Gln  His  Arg  His  Ala  Arg  Leu  Pro  Val  Lys  Trp  Met
1105                     1110                     1115                     1120
Ala  Leu  Glu  Ser  Leu  Gln  Thr  Tyr  Arg  Phe  Thr  Thr  Lys  Ser  Asp  Val
               1125                     1130                          1135
Val  Pro  Ser  Asp  Ala  Ala  Met  Leu  Gly  Gly  Arg  Pro  Ser  Ser  Ala  Thr
               1140                     1145                          1150
His  Leu  Gln  Ser  Thr  Ser  Gly  Gly  Gly  Ala  Asp  Ser  Val  Cys  Thr
               1155                     1160                     1165
Ala  Trp  Gly  Pro  Leu  Cys  Ala  Ala  Ser  Asn  Leu  His  Glu  Leu  Glu
     1170                     1175                     1180
Leu  Thr  Pro  Arg  Leu  Pro  Leu  Gly  His  Ala  Arg  Pro  Glu  Gln  Trp  Pro
1185                     1190                     1195                     1200
Ser  Thr  Leu  Phe  Leu  Pro  Phe  Asn  Phe  Gln  Arg  Gln
               1205                     1210
```

FIG. 4C-1         Coding Sequence (SEQ ID NO: 7 & 8)

```
ATG GAG CTC CTC CCG CCG CTG CCT CAG TCC TTC CTG TTG CTG CTG CTG    48
Met Glu Leu Leu Pro Pro Leu Pro Gln Ser Phe Leu Leu Leu Leu Leu
                 5                  10                 15
TTG CCT GCC AAG CCC GCG GCG GGC GAG GAC TGG CAG TGC CCG CGC ACC    96
Leu Pro Ala Lys Pro Ala Ala Gly Glu Asp Trp Gln Cys Pro Arg Thr
             20                  25                 30
CCC TAC GCG GCC TCT CGC GAC TTT GAC GTG AAG TAC GTG GTG CCC AGC   144
Pro Tyr Ala Ala Ser Arg Asp Phe Asp Val Lys Tyr Val Val Pro Ser
             35                  40                 45
TTC TCC GCC GGA GGC CTG GTA CAG GCC ATG GTG ACC TAC GAG GGC GAC   192
Phe Ser Ala Gly Gly Leu Val Gln Ala Met Val Thr Tyr Glu Gly Asp
         50                  55                 60
AGA AAT GAG AGT GCT GTG TTT GTA GCC ATA CGC AAT CGC CTG CAT GTG   240
Arg Asn Glu Ser Ala Val Phe Val Ala Ile Arg Asn Arg Leu His Val
 65                  70                  75                 80
CTT GGG CCT GAC CTG AAG TCT GTC CAG AGC CTG GCC ACG GGC CCT GCT   288
Leu Gly Pro Asp Leu Lys Ser Val Gln Ser Leu Ala Thr Gly Pro Ala
                 85                  90                 95
GGA GAC CCT GGC TGC CAG ACG TGT GCA GCC TGT GGC CCA GGA CCC CAC   336
Gly Asp Pro Gly Cys Gln Thr Cys Ala Ala Cys Gly Pro Gly Pro His
             100                 105                110
GGC CCT CCC GGT GAC ACA GAC ACA AAG GTG CTG GTG CTG GAT CCC GCG   384
Gly Pro Pro Gly Asp Thr Asp Thr Lys Val Leu Val Leu Asp Pro Ala
             115                 120                125
CTG CCT GCG CTG GTC AGT TGT GGC TCC AGC CTG CAG GGC CGC TGC TTC   432
Leu Pro Ala Leu Val Ser Cys Gly Ser Ser Leu Gln Gly Arg Cys Phe
         130                 135                140
CTG CAT GAC CTA GAG CCC CAA GGG ACA GCC GTG CAT CTG GCA GCG CCA   480
Leu His Asp Leu Glu Pro Gln Gly Thr Ala Val His Leu Ala Ala Pro
145                 150                 155                160
GCC TGC CTC TTC TCA GCC CAC CAT AAC CGG CCC GAT GAC TGC CCC GAC   528
Ala Cys Leu Phe Ser Ala His His Asn Arg Pro Asp Asp Cys Pro Asp
                 165                 170                175
TGT GTG GCC AGC CCA TTG GGC ACC CGT GTA ACT GTG GTT GAG CAA GGC   576
Cys Val Ala Ser Pro Leu Gly Thr Arg Val Thr Val Val Glu Gln Gly
             180                 185                190
CAG GCC TCC TAT TTC TAC GTG GCA TCC TCA CTG GAC GCA GCC GTG GCT   624
Gln Ala Ser Tyr Phe Tyr Val Ala Ser Ser Leu Asp Ala Ala Val Ala
             195                 200                205
GGC AGC TTC AGC CCA CGC TCA GTG TCT ATC AGG CGT CTC AAG GCT GAC   672
Gly Ser Phe Ser Pro Arg Ser Val Ser Ile Arg Arg Leu Lys Ala Asp
         210                 215                220
GCC TCG GGA TTC GCA CCG GGC TTT GTG GCG TTG TCA GTG CTG CCC AAG   720
Ala Ser Gly Phe Ala Pro Gly Phe Val Ala Leu Ser Val Leu Pro Lys
225                 230                 235                240
CAT CTT GTC TCC TAC AGT ATT GAA TAC GTG CAC AGC TTC CAC ACG GGA   768
His Leu Val Ser Tyr Ser Ile Glu Tyr Val His Ser Phe His Thr Gly
                 245                 250                255
GCC TTC GTA TAC TTC CTG ACT GTA CAG CCG GCC AGC GTG ACA GAT GAT   816
Ala Phe Val Tyr Phe Leu Thr Val Gln Pro Ala Ser Val Thr Asp Asp
             260                 265                270
CCT AGT GCC CTG CAC ACA CGC CTG GCA CGG CTT AGC GCC ACT GAG CCA   864
Pro Ser Ala Leu His Thr Arg Leu Ala Arg Leu Ser Ala Thr Glu Pro
             275                 280                285
GAG TTG GGT GAC TAT CGG GAG CTG GTC CTC GAC TGC AGA TTT GCT CCA   912
Glu Leu Gly Asp Tyr Arg Glu Leu Val Leu Asp Cys Arg Phe Ala Pro
         290                 295                300
AAA CGC AGG AGG CGG GGG GCC CCA GAA GGC GGA CAG CCC TAC CCT GTG   960
Lys Arg Arg Arg Arg Gly Ala Pro Glu Gly Gly Gln Pro Tyr Pro Val
305                 310                 315                320
```

FIG. 4C-2     Coding Sequence (SEQ ID NO: 7 & 8) cont.

| | | | | | | | | | | | | | | | | |
|---|---|---|---|---|---|---|---|---|---|---|---|---|---|---|---|---|
| CTG | CAG | GTG | GCC | CAC | TCC | GCT | CCA | GTG | GGT | GCC | CAA | CTT | GCC | ACT | GAG | 1008 |
| Leu | Gln | Val | Ala | His | Ser | Ala | Pro | Val | Gly | Ala | Gln | Leu | Ala | Thr | Glu | |
| | | | | 325 | | | | 330 | | | | | | 335 | | |
| CTG | AGC | ATC | GCC | GAG | GGC | CAG | GAA | GTA | CTA | TTT | GGG | GTC | TTT | GTG | ACT | 1056 |
| Leu | Ser | Ile | Ala | Glu | Gly | Gln | Glu | Val | Leu | Phe | Gly | Val | Phe | Val | Thr | |
| | | | 340 | | | | | 345 | | | | | 350 | | | |
| GGC | AAG | GAT | GGT | GGT | CCT | GGC | GTG | GGC | CCC | AAC | TCT | GTC | GTC | TGT | GCC | 1104 |
| Gly | Lys | Asp | Gly | Gly | Pro | Gly | Val | Gly | Pro | Asn | Ser | Val | Val | Cys | Ala | |
| | | 355 | | | | | 360 | | | | | 365 | | | | |
| TTC | CCC | ATT | GAC | CTG | CTG | GAC | ACA | CTA | ATT | GAT | GAG | GGT | GTG | GAG | CGC | 1152 |
| Phe | Pro | Ile | Asp | Leu | Leu | Asp | Thr | Leu | Ile | Asp | Glu | Gly | Val | Glu | Arg | |
| | 370 | | | | | 375 | | | | | 380 | | | | | |
| TGT | TGT | GAA | TCC | CCA | GTC | CAT | CCA | GGC | CTC | CGG | CGA | GGC | CTC | GAC | TTC | 1200 |
| Cys | Cys | Glu | Ser | Pro | Val | His | Pro | Gly | Leu | Arg | Arg | Gly | Leu | Asp | Phe | |
| 385 | | | | | 390 | | | | | 395 | | | | | 400 | |
| TTC | CAG | TCG | CCC | AGT | TTT | TGC | CCC | AAC | CCG | CCT | GGC | CTG | GAA | GCC | CTC | 1248 |
| Phe | Gln | Ser | Pro | Ser | Phe | Cys | Pro | Asn | Pro | Pro | Gly | Leu | Glu | Ala | Leu | |
| | | | | 405 | | | | | 410 | | | | | 415 | | |
| AGC | CCC | AAC | ACC | AGC | TGC | CGC | CAC | TTC | CCT | CTG | CTG | GTC | AGT | AGC | AGC | 1296 |
| Ser | Pro | Asn | Thr | Ser | Cys | Arg | His | Phe | Pro | Leu | Leu | Val | Ser | Ser | Ser | |
| | | | 420 | | | | | 425 | | | | | 430 | | | |
| TTC | TCA | CGT | GTG | GAC | CTA | TTC | AAT | GGG | CTG | TTG | GGA | CCA | GTA | CAG | GTC | 1344 |
| Phe | Ser | Arg | Val | Asp | Leu | Phe | Asn | Gly | Leu | Leu | Gly | Pro | Val | Gln | Val | |
| | | 435 | | | | | 440 | | | | | 445 | | | | |
| ACT | GCA | TTG | TAT | GTG | ACA | CGC | CTT | GAC | AAC | GTC | ACA | GTG | GCA | CAC | ATG | 1392 |
| Thr | Ala | Leu | Tyr | Val | Thr | Arg | Leu | Asp | Asn | Val | Thr | Val | Ala | His | Met | |
| | 450 | | | | | 455 | | | | | 460 | | | | | |
| GGC | ACA | ATG | GAT | GGG | CGT | ATC | CTG | CAG | GTG | GAG | CTG | GTC | AGG | TCA | CTA | 1440 |
| Gly | Thr | Met | Asp | Gly | Arg | Ile | Leu | Gln | Val | Glu | Leu | Val | Arg | Ser | Leu | |
| 465 | | | | | 470 | | | | | 475 | | | | | 480 | |
| AAC | TAC | TTG | CTG | TAT | GTG | TCC | AAC | TTC | TCA | CTG | GGT | GAC | AGT | GGG | CAG | 1488 |
| Asn | Tyr | Leu | Leu | Tyr | Val | Ser | Asn | Phe | Ser | Leu | Gly | Asp | Ser | Gly | Gln | |
| | | | | 485 | | | | | 490 | | | | | 495 | | |
| CCC | GTG | CAG | CGG | GAT | GTC | AGT | CGT | CTT | GGG | GAC | CAC | CTA | CTC | TTT | GCC | 1536 |
| Pro | Val | Gln | Arg | Asp | Val | Ser | Arg | Leu | Gly | Asp | His | Leu | Leu | Phe | Ala | |
| | | | 500 | | | | | 505 | | | | | 510 | | | |
| TCT | GGG | GAC | CAG | GTT | TTC | CAG | GTA | CCT | ATC | CGA | GGC | CCT | GGC | TGC | CGC | 1584 |
| Ser | Gly | Asp | Gln | Val | Phe | Gln | Val | Pro | Ile | Arg | Gly | Pro | Gly | Cys | Arg | |
| | | 515 | | | | | 520 | | | | | 525 | | | | |
| CAC | TTC | CTG | ACC | TGT | GGG | CGT | TGC | CTA | AGG | GCA | TGG | CAT | TTC | ATG | GGC | 1632 |
| His | Phe | Leu | Thr | Cys | Gly | Arg | Cys | Leu | Arg | Ala | Trp | His | Phe | Met | Gly | |
| | 530 | | | | | 535 | | | | | 540 | | | | | |
| TGT | GGC | TGG | TGT | GGG | AAC | ATG | TGC | GGC | CAG | CAG | AAG | GAG | TGT | CCT | GGC | 1680 |
| Cys | Gly | Trp | Cys | Gly | Asn | Met | Cys | Gly | Gln | Gln | Lys | Glu | Cys | Pro | Gly | |
| 545 | | | | | 550 | | | | | 555 | | | | | 560 | |
| TCC | TGG | CAA | CAG | GAC | CAC | TGC | CCA | CCT | AAG | CTT | ACT | GAG | TTC | CAC | CCC | 1728 |
| Ser | Trp | Gln | Gln | Asp | His | Cys | Pro | Pro | Lys | Leu | Thr | Glu | Phe | His | Pro | |
| | | | | 565 | | | | | 570 | | | | | 575 | | |
| CAC | AGT | GGA | CCT | CTA | AGG | GGC | AGT | ACA | AGG | CTG | ACC | CTG | TGT | GGC | TCC | 1776 |
| His | Ser | Gly | Pro | Leu | Arg | Gly | Ser | Thr | Arg | Leu | Thr | Leu | Cys | Gly | Ser | |
| | | | 580 | | | | | 585 | | | | | 590 | | | |
| AAC | TTC | TAC | CTT | CAC | CCT | TCT | GGT | CTG | GTG | CCT | GAG | GGA | ACC | CAT | CAG | 1824 |
| Asn | Phe | Tyr | Leu | His | Pro | Ser | Gly | Leu | Val | Pro | Glu | Gly | Thr | His | Gln | |
| | | 595 | | | | | 600 | | | | | 605 | | | | |
| GTC | ACT | GTG | GGC | CAA | AGT | CCC | TGC | CGG | CCA | CTG | CCC | AAG | GAC | AGC | TCA | 1872 |
| Val | Thr | Val | Gly | Gln | Ser | Pro | Cys | Arg | Pro | Leu | Pro | Lys | Asp | Ser | Ser | |
| | 610 | | | | | 615 | | | | | 620 | | | | | |
| AAA | CTC | AGA | CCA | GTG | CCC | CGG | AAA | GAC | TTT | GTA | GAG | GAG | TTT | GAG | TGT | 1920 |
| Lys | Leu | Arg | Pro | Val | Pro | Arg | Lys | Asp | Phe | Val | Glu | Glu | Phe | Glu | Cys | |
| 625 | | | | | 630 | | | | | 635 | | | | | 640 | |

FIG. 4C-3  Coding Sequence (SEQ ID NO: 7 & 8) cont.

| | | | | | | | | | | | | | | | | |
|---|---|---|---|---|---|---|---|---|---|---|---|---|---|---|---|---|
| GAA | CTG | GAG | CCC | TTG | GGC | ACC | CAG | GCA | GTG | GGG | CCT | ACC | AAC | GTC | AGC | 1968 |
| Glu | Leu | Glu | Pro | Leu | Gly | Thr | Gln | Ala | Val | Gly | Pro | Thr | Asn | Val | Ser | |
| | | | | 645 | | | | | 650 | | | | | 655 | | |
| CTC | ACC | GTG | ACT | AAC | ATG | CCA | CCG | GGC | AAG | CAC | TTC | CGG | GTA | GAC | GGC | 2016 |
| Leu | Thr | Val | Thr | Asn | Met | Pro | Pro | Gly | Lys | His | Phe | Arg | Val | Asp | Gly | |
| | | | 660 | | | | | 665 | | | | | 670 | | | |
| ACC | TCC | GTG | CTG | AGA | GGC | TTC | TCT | TTC | ATG | GAG | CCA | GTG | CTG | ATA | GCA | 2064 |
| Thr | Ser | Val | Leu | Arg | Gly | Phe | Ser | Phe | Met | Glu | Pro | Val | Leu | Ile | Ala | |
| | | 675 | | | | | 680 | | | | | 685 | | | | |
| GTG | CAA | CCC | CTC | TTT | GGC | CCA | CGG | GCA | GGA | GGC | ACC | TGT | CTC | ACT | CTT | 2112 |
| Val | Gln | Pro | Leu | Phe | Gly | Pro | Arg | Ala | Gly | Gly | Thr | Cys | Leu | Thr | Leu | |
| | 690 | | | | | 695 | | | | | 700 | | | | | |
| GAA | GGC | CAG | AGT | CTG | TCT | GTA | GGC | ACC | AGC | CGG | GCT | GTG | CTG | GTC | AAT | 2160 |
| Glu | Gly | Gln | Ser | Leu | Ser | Val | Gly | Thr | Ser | Arg | Ala | Val | Leu | Val | Asn | |
| 705 | | | | | 710 | | | | | 715 | | | | | 720 | |
| GGG | ACT | GAG | TGT | CTG | CTA | GCA | CGG | GTC | AGT | GAG | GGG | CAG | CTT | TTA | TGT | 2208 |
| Gly | Thr | Glu | Cys | Leu | Leu | Ala | Arg | Val | Ser | Glu | Gly | Gln | Leu | Leu | Cys | |
| | | | | 725 | | | | | 730 | | | | | 735 | | |
| GCC | ACA | CCC | CCT | GGG | GCC | ACG | GTG | GCC | AGT | GTC | CCC | CTT | AGC | CTG | CAG | 2256 |
| Ala | Thr | Pro | Pro | Gly | Ala | Thr | Val | Ala | Ser | Val | Pro | Leu | Ser | Leu | Gln | |
| | | | 740 | | | | | 745 | | | | | 750 | | | |
| GTG | GGG | GGT | GCC | CAG | GTA | CCT | GGT | TCC | TGG | ACC | TTC | CAG | TAC | AGA | GAA | 2304 |
| Val | Gly | Gly | Ala | Gln | Val | Pro | Gly | Ser | Trp | Thr | Phe | Gln | Tyr | Arg | Glu | |
| | | 755 | | | | | 760 | | | | | 765 | | | | |
| GAC | CCT | GTC | GTG | CTA | AGC | ATC | AGC | CCC | AAC | TGT | GGC | TAC | ATC | AAC | TCC | 2352 |
| Asp | Pro | Val | Val | Leu | Ser | Ile | Ser | Pro | Asn | Cys | Gly | Tyr | Ile | Asn | Ser | |
| | 770 | | | | | 775 | | | | | 780 | | | | | |
| CAC | ATC | ACC | ATC | TGT | GGC | CAG | CAT | CTA | ACT | TCA | GCA | TGG | CAC | TTA | GTG | 2400 |
| His | Ile | Thr | Ile | Cys | Gly | Gln | His | Leu | Thr | Ser | Ala | Trp | His | Leu | Val | |
| 785 | | | | | 790 | | | | | 795 | | | | | 800 | |
| CTG | TCA | TTC | CAT | GAC | GGG | CTT | AGG | GCA | GTG | GAA | AGC | AGG | TGT | GAG | AGG | 2448 |
| Leu | Ser | Phe | His | Asp | Gly | Leu | Arg | Ala | Val | Glu | Ser | Arg | Cys | Glu | Arg | |
| | | | | 805 | | | | | 810 | | | | | 815 | | |
| CAG | CTT | CCA | GAG | CAG | CAG | CTG | TGC | CGC | CTT | CCT | GAA | TAT | GTG | GTC | CGA | 2496 |
| Gln | Leu | Pro | Glu | Gln | Gln | Leu | Cys | Arg | Leu | Pro | Glu | Tyr | Val | Val | Arg | |
| | | | 820 | | | | | 825 | | | | | 830 | | | |
| GAC | CCC | CAG | GGA | TGG | GTG | GCA | GGG | AAT | CTG | AGT | GCC | CGA | GGG | GAT | GGA | 2544 |
| Asp | Pro | Gln | Gly | Trp | Val | Ala | Gly | Asn | Leu | Ser | Ala | Arg | Gly | Asp | Gly | |
| | | 835 | | | | | 840 | | | | | 845 | | | | |
| GCT | GCT | GGC | TTT | ACA | CTG | CCT | GGC | TTT | CGC | TTC | CTA | CCC | CCA | CCC | CAT | 2592 |
| Ala | Ala | Gly | Phe | Thr | Leu | Pro | Gly | Phe | Arg | Phe | Leu | Pro | Pro | Pro | His | |
| | 850 | | | | | 855 | | | | | 860 | | | | | |
| CCA | CCC | AGT | GCC | AAC | CTA | GTT | CCA | CTG | AAG | CCT | GAG | GAG | CAT | GCC | ATT | 2640 |
| Pro | Pro | Ser | Ala | Asn | Leu | Val | Pro | Leu | Lys | Pro | Glu | Glu | His | Ala | Ile | |
| 865 | | | | | 870 | | | | | 875 | | | | | 880 | |
| AAG | TTT | GAG | GTC | TGC | GTA | GAT | GCA | CTC | CCT | GCC | ATT | GAT | GGT | CTG | GAT | 2688 |
| Lys | Phe | Glu | Val | Cys | Val | Asp | Ala | Leu | Pro | Ala | Ile | Asp | Gly | Leu | Asp | |
| | | | | 885 | | | | | 890 | | | | | 895 | | |
| TCC | ACC | ACT | TGT | GTC | CAT | GGA | GCA | TCC | TTC | TCC | GAT | AGT | GAA | GAT | GAA | 2736 |
| Ser | Thr | Thr | Cys | Val | His | Gly | Ala | Ser | Phe | Ser | Asp | Ser | Glu | Asp | Glu | |
| | | | 900 | | | | | 905 | | | | | 910 | | | |
| TCC | TGT | GTG | CCA | CTG | CTG | CGG | AAA | GAG | TCC | ATC | CAG | CTA | AGG | GAC | CTG | 2784 |
| Ser | Cys | Val | Pro | Leu | Leu | Arg | Lys | Glu | Ser | Ile | Gln | Leu | Arg | Asp | Leu | |
| | | 915 | | | | | 920 | | | | | 925 | | | | |
| GAC | TCT | GCG | CTC | TTG | GCT | GAG | GTC | AAG | GAT | GTG | CTG | ATT | CCC | CAT | GAG | 2832 |
| Asp | Ser | Ala | Leu | Leu | Ala | Glu | Val | Lys | Asp | Val | Leu | Ile | Pro | His | Glu | |
| | 930 | | | | | 935 | | | | | 940 | | | | | |
| CGG | GTG | GTC | ACC | CAC | AGT | GAC | CGA | GTC | ATT | GGC | AAA | GGC | CAC | TTT | GGA | 2880 |
| Arg | Val | Val | Thr | His | Ser | Asp | Arg | Val | Ile | Gly | Lys | Gly | His | Phe | Gly | |
| 945 | | | | | 950 | | | | | 955 | | | | | 960 | |

FIG. 4C-4          Coding Sequence (SEQ ID NO: 7 & 8) cont.

```
GTT GTC TAC CAC GGA GAA TAC ATA GAC CAG GCC CAG AAT CGA ATC CAA 2928
Val Val Tyr His Gly Glu Tyr Ile Asp Gln Ala Gln Asn Arg Ile Gln
                965             970             975
TGT GCC ATC AAG TCA CTA AGT CGC ATC ACA GAG ATG CAG CAG GTG GAG 2976
Cys Ala Ile Lys Ser Leu Ser Arg Ile Thr Glu Met Gln Gln Val Glu
            980             985             990
GCC TTC CTG CGA GAG GGG CTG CTC ATG CGT GGC CTG AAC CAC CCG AAT 3024
Ala Phe Leu Arg Glu Gly Leu Leu Met Arg Gly Leu Asn His Pro Asn
        995             1000            1005
GTG CTG GCT CTC ATT GGT ATC ATG TTG CCA CCT GAG GGC CTG CCC CAT 3072
Val Leu Ala Leu Ile Gly Ile Met Leu Pro Pro Glu Gly Leu Pro His
    1010            1015            1020
GTG CTG CTG CCC TAT ATG TGC CAC GGT GAC CTC CTC CAG TTC ATC CGC 3120
Val Leu Leu Pro Tyr Met Cys His Gly Asp Leu Leu Gln Phe Ile Arg
1025            1030            1035            1040
TCA CCT CAG CGG AAC CCC ACC GTG AAG GAC CTC ATC AGC TTT GGC CTG 3168
Ser Pro Gln Arg Asn Pro Thr Val Lys Asp Leu Ile Ser Phe Gly Leu
                1045            1050            1055
CAG GTA GCC CGC GGC ATG GAG TAC CTG GCA GAG CAG AAG TTT GTG CAC 3216
Gln Val Ala Arg Gly Met Glu Tyr Leu Ala Glu Gln Lys Phe Val His
            1060            1065            1070
AGG GAC CTG GCT GCG CGG AAC TGC ATG CTG GAC GAG TCA TTC ACA GTC 3264
Arg Asp Leu Ala Ala Arg Asn Cys Met Leu Asp Glu Ser Phe Thr Val
        1075            1080            1085
AAG GTG GCT GAC TTT GGT TTG GCC CGC GAC ATC CTG GAC AGG GAG TAC 3312
Lys Val Ala Asp Phe Gly Leu Ala Arg Asp Ile Leu Asp Arg Glu Tyr
    1090            1095            1100
TAT AGT GTT CAA CAG CAT CGC CAC GCT CGC CTA CCT GTG AAG TGG ATG 3360
Tyr Ser Val Gln Gln His Arg His Ala Arg Leu Pro Val Lys Trp Met
1105            1110            1115            1120
GCG CTG GAG AGC CTG CAG ACC TAT AGA TTT ACC ACC AAG TCT GAT GTG 3408
Ala Leu Glu Ser Leu Gln Thr Tyr Arg Phe Thr Thr Lys Ser Asp Val
                1125            1130            1135
GTA CCA AGT GAT GCA GCA ATG CTG GGA GGC AGA CCC AGC AGT GCG ACC 3456
Val Pro Ser Asp Ala Ala Met Leu Gly Gly Arg Pro Ser Ser Ala Thr
            1140            1145            1150
CAC CTT CAG AGT ACT AGT GGG GGA GGT GGA GCA GAT AGT GTC TGC ACT 3504
His Leu Gln Ser Thr Ser Gly Gly Gly Gly Ala Asp Ser Val Cys Thr
        1155            1160            1165
GCT TGG GGA CCA TTA TGT GCA GCT GCC AGC AAC CTA CAT GAA CTT GAG 3552
Ala Trp Gly Pro Leu Cys Ala Ala Ala Ser Asn Leu His Glu Leu Glu
    1170            1175            1180
CTA ACC CCA AGG CTG CCT CTG GGC CAT GCC AGG CCA GAG CAG TGG CCC 3600
Leu Thr Pro Arg Leu Pro Leu Gly His Ala Arg Pro Glu Gln Trp Pro
1185            1190            1195            1200
TCC ACC TTG TTC CTG CCC TTT AAC TTT CAG AGG CAA                  3636
Ser Thr Leu Phe Leu Pro Phe Asn Phe Gln Arg Gln
                1205            1210
```

FIG. 5-1  SEQ ID NOs: 2, 4, 6, 8

```
Ron-V3  GGATCCTCTAGGGTC  CCAGCTCGCCTCGAT  GGAGCTCCTCCCGCC  GCTGCCTCAGTCCTT  CCTGTTGCTGCTGCT  GTTGCCTGCCAAGCC  90
Ron-V2  GGATCCTCTAGGGTC  CCAGCTCGCCTCGAT  GGAGCTCCTCCCGCC  GCTGCCTCAGTCCTT  CCTGTTGCTGCTGCT  GTTGCCTGCCAAGCC  90
Ron-V1  GGATCCTCTAGGGTC  CCAGCTCGCCTCGAT  GGAGCTCCTCCCGCC  GCTGCCTCAGTCCTT  CCTGTTGCTGCTGCT  GTTGCCTGCCAAGCC  90
Ron     GGATCCTCTAGGGTC  CCAGCTCGCCTCGAT  GGAGCTCCTCCCGCC  GCTGCCTCAGTCCTT  CCTGTTGCTGCTGCT  GTTGCCTGCCAAGCC  90

Ron-V3  CGCGGCGGGCGAGGA  CTGGCAGTGCCCGCG  CACCCCCTACGCGGC  CTCTCGCGACTTTGA  CGTGAAGTACGTGGT  GCCCAGCTTCTCCGC  180
Ron-V2  CGCGGCGGGCGAGGA  CTGGCAGTGCCCGCG  CACCCCCTACGCGGC  CTCTCGCGACTTTGA  CGTGAAGTACGTGGT  GCCCAGCTTCTCCGC  180
Ron-V1  CGCGGCGGGCGAGGA  CTGGCAGTGCCCGCG  CACCCCCTACGCGGC  CTCTCGCGACTTTGA  CGTGAAGTACGTGGT  GCCCAGCTTCTCCGC  180
Ron     CGCGGCGGGCGAGGA  CTGGCAGTGCCCGCG  CACCCCCTACGCGGC  CTCTCGCGACTTTGA  CGTGAAGTACGTGGT  GCCCAGCTTCTCCGC  180

Ron-V3  CGGAGAGGCCTGGTACA  GGCCATGGTGACCTA  CGAGGGCGACAGAAA  TGAGAGTGCTGTGTT  TGTAGCCATACGCAA  TCGCCTGCATGTGCT  270
Ron-V2  CGGAGAGGCCTGGTACA  GGCCATGGTGACCTA  CGAGGGCGACAGAAA  TGAGAGTGCTGTGTT  TGTAGCCATACGCAA  TCGCCTGCATGTGCT  270
Ron-V1  CGGAGAGGCCTGGTACA  GGCCATGGTGACCTA  CGAGGGCGACAGAAA  TGAGAGTGCTGTGTT  TGTAGCCATACGCAA  TCGCCTGCATGTGCT  270
Ron     CGGAGAGGCCTGGTACA  GGCCATGGTGACCTA  CGAGGGCGACAGAAA  TGAGAGTGCTGTGTT  TGTAGCCATACGCAA  TCGCCTGCATGTGCT  270

Ron-V3  TGGGCCTGACCTGAA  GTCTGTCCAGAGCCT  GGCCACGGGCCCTGC  TGGAGACCCTGGCTG  CCAGACGTGTGCAGC  CTGTGGCCAGGACC   360
Ron-V2  TGGGCCTGACCTGAA  GTCTGTCCAGAGCCT  GGCCACGGGCCCTGC  TGGAGACCCTGGCTG  CCAGACGTGTGCAGC  CTGTGGCCAGGACC   360
Ron-V1  TGGGCCTGACCTGAA  GTCTGTCCAGAGCCT  GGCCACGGGCCCTGC  TGGAGACCCTGGCTG  CCAGACGTGTGCAGC  CTGTGGCCAGGACC   360
Ron     TGGGCCTGACCTGAA  GTCTGTCCAGAGCCT  GGCCACGGGCCCTGC  TGGAGACCCTGGCTG  CCAGACGTGTGCAGC  CTGTGGCCAGGACC   360

Ron-V3  CCACGGCCCTCCCGG  TGACACAGACACAAA  GGTGCTGGTGCTGGA  TCCCGCGCTGCCTGC  GCTGGTCAGTTGTGG  CTCCAGCCTGCAGGG  450
Ron-V2  CCACGGCCCTCCCGG  TGACACAGACACAAA  GGTGCTGGTGCTGGA  TCCCGCGCTGCCTGC  GCTGGTCAGTTGTGG  CTCCAGCCTGCAGGG  450
Ron-V1  CCACGGCCCTCCCGG  TGACACAGACACAAA  GGTGCTGGTGCTGGA  TCCCGCGCTGCCTGC  GCTGGTCAGTTGTGG  CTCCAGCCTGCAGGG  450
Ron     CCACGGCCCTCCCGG  TGACACAGACACAAA  GGTGCTGGTGCTGGA  TCCCGCGCTGCCTGC  GCTGGTCAGTTGTGG  CTCCAGCCTGCAGGG  450
```

FIG. 5-2   SEQ ID NOs: 2, 4, 6, 8 cont.

```
Ron-V3  CCGCTGCTTCCTGCA TGACCTAGAGAGCCCCA AGGGACAGAGCCGTGCA TCTGGCAGCGCCAGC CTGCCTCTTCTCAGC CCACCATAACCGGCC  540
Ron-V2  CCGCTGCTTCCTGCA TGACCTAGAGAGCCCCA AGGGACAGAGCCGTGCA TCTGGCAGCGCCAGC CTGCCTCTTCTCAGC CCACCATAACCGGCC  540
Ron-V1  CCGCTGCTTCCTGCA TGACCTAGAGAGCCCCA AGGGACAGAGCCGTGCA TCTGGCAGCGCCAGC CTGCCTCTTCTCAGC CCACCATAACCGGCC  540
Ron     CCGCTGCTTCCTGCA TGACCTAGAGAGCCCCA AGGGACAGAGCCGTGCA TCTGGCAGCGCCAGC CTGCCTCTTCTCAGC CCACCATAACCGGCC  540

Ron-V3  CGATGACTGCCCCGA CTGTGTGGCCAGCCC ATTGGGCACCCGTGT AACTGTGGTTGAGCA AGGCCAGGCCTCCTA TTTCTACGTGGCATC  630
Ron-V2  CGATGACTGCCCCGA CTGTGTGGCCAGCCC ATTGGGCACCCGTGT AACTGTGGTTGAGCA AGGCCAGGCCTCCTA TTTCTACGTGGCATC  630
Ron-V1  CGATGACTGCCCCGA CTGTGTGGCCAGCCC ATTGGGCACCCGTGT AACTGTGGTTGAGCA AGGCCAGGCCTCCTA TTTCTACGTGGCATC  630
Ron     CGATGACTGCCCCGA CTGTGTGGCCAGCCC ATTGGGCACCCGTGT AACTGTGGTTGAGCA AGGCCAGGCCTCCTA TTTCTACGTGGCATC  630

Ron-V3  CTCACTGGACGCAGC CGTGGCTGGCCAGCTT CAGCCCACGCTCAGT GTCTATCAGGCGTCT CAAGGCTGACGCCTC GGGATTCGCCACGGG  720
Ron-V2  CTCACTGGACGCAGC CGTGGCTGGCCAGCTT CAGCCCACGCTCAGT GTCTATCAGGCGTCT CAAGGCTGACGCCTC GGGATTCGCCACGGG  720
Ron-V1  CTCACTGGACGCAGC CGTGGCTGGCCAGCTT CAGCCCACGCTCAGT GTCTATCAGGCGTCT CAAGGCTGACGCCTC GGGATTCGCCACGGG  720
Ron     CTCACTGGACGCAGC CGTGGCTGGCCAGCTT CAGCCCACGCTCAGT GTCTATCAGGCGTCT CAAGGCTGACGCCTC GGGATTCGCCACGGG  720

Ron-V3  CTTTGTGGCGTTGTC AGTGCTGCCCAAGCA TCTTGTCTCTCCTACAG TATTGAATACGTGCA CAGCTTCCACACGGG AGCCTTCGTATACTT  810
Ron-V2  CTTTGTGGCGTTGTC AGTGCTGCCCAAGCA TCTTGTCTCTCCTACAG TATTGAATACGTGCA CAGCTTCCACACGGG AGCCTTCGTATACTT  810
Ron-V1  CTTTGTGGCGTTGTC AGTGCTGCCCAAGCA TCTTGTCTCTCCTACAG TATTGAATACGTGCA CAGCTTCCACACGGG AGCCTTCGTATACTT  810
Ron     CTTTGTGGCGTTGTC AGTGCTGCCCAAGCA TCTTGTCTCTCCTACAG TATTGAATACGTGCA CAGCTTCCACACGGG AGCCTTCGTATACTT  810

Ron-V3  CCTGACTGTACAGCC GGCCAGCGTGACAGA TGATCCTAGTGCCCT GCACACACGCCTGGC ACGGCTTAGCGCCAC TGAGCCAGAGTTGGG  900
Ron-V2  CCTGACTGTACAGCC GGCCAGCGTGACAGA TGATCCTAGTGCCCT GCACACACGCCTGGC ACGGCTTAGCGCCAC TGAGCCAGAGTTGGG  900
Ron-V1  CCTGACTGTACAGCC GGCCAGCGTGACAGA TGATCCTAGTGCCCT GCACACACGCCTGGC ACGGCTTAGCGCCAC TGAGCCAGAGTTGGG  900
Ron     CCTGACTGTACAGCC GGCCAGCGTGACAGA TGATCCTAGTGCCCT GCACACACGCCTGGC ACGGCTTAGCGCCAC TGAGCCAGAGTTGGG  900
```

FIG. 5-3    SEQ ID NOs: 2, 4, 6, 8 cont.

```
Ron-V3  TGACTATCGGGAGCT GGTCCTCGACTGCAG ATTTGCTCCAAAACG CAGGCGCCGGGGGC CCCAGAAGGCGGACA GCCCTACCCTGTGCT  990
Ron-V2  TGACTATCGGGAGCT GGTCCTCGACTGCAG ATTTGCTCCAAAACG CAGGCGCCGGGGGC CCCAGAAGGCGGACA GCCCTACCCTGTGCT  990
Ron-V1  TGACTATCGGGAGCT GGTCCTCGACTGCAG ATTTGCTCCAAAACG CAGGCGCCGGGGGC CCCAGAAGGCGGACA GCCCTACCCTGTGCT  990
Ron     TGACTATCGGGAGCT GGTCCTCGACTGCAG ATTTGCTCCAAAACG CAGGCGCCGGGGGC CCCAGAAGGCGGACA GCCCTACCCTGTGCT  990

Ron-V3  GCAGGTGGCCCACTC CGCTCCAGTGGGTGC CCAACTTGCCACTGA GCTGAGCATCGCCGA GGGCCAGGAAGTACT ATTTGGGTCTTTGT  1080
Ron-V2  GCAGGTGGCCCACTC CGCTCCAGTGGGTGC CCAACTTGCCACTGA GCTGAGCATCGCCGA GGGCCAGGAAGTACT ATTTGGGTCTTTGT  1080
Ron-V1  GCAGGTGGCCCACTC CGCTCCAGTGGGTGC CCAACTTGCCACTGA GCTGAGCATCGCCGA GGGCCAGGAAGTACT ATTTGGGTCTTTGT  1080
Ron     GCAGGTGGCCCACTC CGCTCCAGTGGGTGC CCAACTTGCCACTGA GCTGAGCATCGCCGA GGGCCAGGAAGTACT ATTTGGGTCTTTGT  1080

Ron-V3  GACTGGCAAGGATGG TGGTCCTGGCGTGGG CCCCAACTCTGTCGT CTGTGCCTTCCCCAT TGACCTGCTGGACAC ACTAATTGATGAGGG  1170
Ron-V2  GACTGGCAAGGATGG TGGTCCTGGCGTGGG CCCCAACTCTGTCGT CTGTGCCTTCCCCAT TGACCTGCTGGACAC ACTAATTGATGAGGG  1170
Ron-V1  GACTGGCAAGGATGG TGGTCCTGGCGTGGG CCCCAACTCTGTCGT CTGTGCCTTCCCCAT TGACCTGCTGGACAC ACTAATTGATGAGGG  1170
Ron     GACTGGCAAGGATGG TGGTCCTGGCGTGGG CCCCAACTCTGTCGT CTGTGCCTTCCCCAT TGACCTGCTGGACAC ACTAATTGATGAGGG  1170

Ron-V3  TGTGGAGCGCTGTTG TGAATCCCCAGTCCA TCCAGGCCTCCGGCG AGGCCTCGACTTCTT CCAGTCGCCCAGTTT TTGCCCCAACCCGCC  1260
Ron-V2  TGTGGAGCGCTGTTG TGAATCCCCAGTCCA TCCAGGCCTCCGGCG AGGCCTCGACTTCTT CCAGTCGCCCAGTTT TTGCCCCAACCCGCC  1260
Ron-V1  TGTGGAGCGCTGTTG TGAATCCCCAGTCCA TCCAGGCCTCCGGCG AGGCCTCGACTTCTT CCAGTCGCCCAGTTT TTGCCCCAACCCGCC  1260
Ron     TGTGGAGCGCTGTTG TGAATCCCCAGTCCA TCCAGGCCTCCGGCG AGGCCTCGACTTCTT CCAGTCGCCCAGTTT TTGCCCCAACCCGCC  1260

Ron-V3  TGGCCTGGAAGCCCT CAGCCCCAACACCAG CTGCCGCCACTTCCC TCTGCTGGTCAGTAG CAGCTTCTCACGTGT GGACCTATTCAATGG  1350
Ron-V2  TGGCCTGGAAGCCCT CAGCCCCAACACCAG CTGCCGCCACTTCCC TCTGCTGGTCAGTAG CAGCTTCTCACGTGT GGACCTATTCAATGG  1350
Ron-V1  TGGCCTGGAAGCCCT CAGCCCCAACACCAG CTGCCGCCACTTCCC TCTGCTGGTCAGTAG CAGCTTCTCACGTGT GGACCTATTCAATGG  1350
Ron     TGGCCTGGAAGCCCT CAGCCCCAACACCAG CTGCCGCCACTTCCC TCTGCTGGTCAGTAG CAGCTTCTCACGTGT GGACCTATTCAATGG  1350
```

FIG. 5-4    SEQ ID NOs: 2, 4, 6, 8 cont.

```
Ron-V3  GCTGTTGGGACCAGT ACAGGTCACTGCATT GTATGTGACACGCCT TGACAACGTCACAGT GGCACACATGGGCAC AATGGATGGGCGTAT  1440
Ron-V2  GCTGTTGGGACCAGT ACAGGTCACTGCATT GTATGTGACACGCCT TGACAACGTCACAGT GGCACACATGGGCAC AATGGATGGGCGTAT  1440
Ron-V1  GCTGTTGGGACCAGT ACAGGTCACTGCATT GTATGTGACACGCCT TGACAACGTCACAGT GGCACACATGGGCAC AATGGATGGGCGTAT  1440
Ron     GCTGTTGGGACCAGT ACAGGTCACTGCATT GTATGTGACACGCCT TGACAACGTCACAGT GGCACACATGGGCAC AATGGATGGGCGTAT  1440

Ron-V3  CCTGCAGGTGGAGCT GGTCAGGTCACTAAA CTACTTGCTGTATGT GTCCAACTTCTCACT GGGTGACAGTGGGCA GCCCGTGCAGCGGGA  1530
Ron-V2  CCTGCAGGTGGAGCT GGTCAGGTCACTAAA CTACTTGCTGTATGT GTCCAACTTCTCACT GGGTGACAGTGGGCA GCCCGTGCAGCGGGA  1530
Ron-V1  CCTGCAGGTGGAGCT GGTCAGGTCACTAAA CTACTTGCTGTATGT GTCCAACTTCTCACT GGGTGACAGTGGGCA GCCCGTGCAGCGGGA  1530
Ron     CCTGCAGGTGGAGCT GGTCAGGTCACTAAA CTACTTGCTGTATGT GTCCAACTTCTCACT GGGTGACAGTGGGCA GCCCGTGCAGCGGGA  1530

Ron-V3  TGTCAGTCGTCTTGG GGACCACTACTCTT TGCCCTCTGGGGACCA GGTTTTCCAGGTACC TATCCGAGGCCCTGG CTGCCGCCACTTCCT  1620
Ron-V2  TGTCAGTCGTCTTGG GGACCACTACTCTT TGCCCTCTGGGGACCA GGTTTTCCAGGTACC TATCCGAGGCCCTGG CTGCCGCCACTTCCT  1620
Ron-V1  TGTCAGTCGTCTTGG GGACCACTACTCTT TGCCCTCTGGGGACCA GGTTTTCCAGGTACC TATCCGAGGCCCTGG CTGCCGCCACTTCCT  1620
Ron     TGTCAGTCGTCTTGG GGACCACTACTCTT TGCCCTCTGGGGACCA GGTTTTCCAGGTACC TATCCGAGGCCCTGG CTGCCGCCACTTCCT  1620

Ron-V3  GACCTGTGGGCGTTG CCTAAGGGCATGGCA TTTCATGGGCTGTGG CTGGTGTGGGAACAT GTGCGGCCAGCAGAA GGAGTGTCCTGGCTC  1710
Ron-V2  GACCTGTGGGCGTTG CCTAAGGGCATGGCA TTTCATGGGCTGTGG CTGGTGTGGGAACAT GTGCGGCCAGCAGAA GGAGTGTCCTGGCTC  1710
Ron-V1  GACCTGTGGGCGTTG CCTAAGGGCATGGCA TTTCATGGGCTGTGG CTGGTGTGGGAACAT GTGCGGCCAGCAGAA GGAGTGTCCTGGCTC  1710
Ron     GACCTGTGGGCGTTG CCTAAGGGCATGGCA TTTCATGGGCTGTGG CTGGTGTGGGAACAT GTGCGGCCAGCAGAA GGAGTGTCCTGGCTC  1710

Ron-V3  CTGGCAACAGGACCA CTGCCCACCTAAGCT TACTGAGTTCCACCC CCACAGTGGACCCTCT AAGGGGCAGTACAAG GCTGACCCTGTGTGG  1800
Ron-V2  CTGGCAACAGGACCA CTGCCCACCTAAGCT TACTGAGTTCCACCC CCACAGTGGACCCTCT AAGGGGCAGTACAAG GCTGACCCTGTGTGG  1800
Ron-V1  CTGGCAACAGGACCA CTGCCCACCTAAGCT TACTGAGTTCCACCC CCACAGTGGACCCTCT AAGGGGCAGTACAAG GCTGACCCTGTGTGG  1800
Ron     CTGGCAACAGGACCA CTGCCCACCTAAGCT TACTGAGTTCCACCC CCACAGTGGACCCTCT AAGGGGCAGTACAAG GCTGACCCTGTGTGG  1800
```

FIG. 5-5  SEQ ID NOs: 2, 4, 6, 8 cont.

```
Ron-V3   CTCCAACTTCTACCT  TCACCCTTCTGGTCT  GGTGCCTGAGGGAAC  CCATCAGTCACTGT  GGGCCAAAGTCCCTG  CCGGCCACTGCCCAA  1890
Ron-V2   CTCCAACTTCTACCT  TCACCCTTCTGGTCT  GGTGCCTGAGGGAAC  CCATCAGTCACTGT  GGGCCAAAGTCCCTG  CCGGCCACTGCCCAA  1890
Ron-V1   CTCCAACTTCTACCT  TCACCCTTCTGGTCT  GGTGCCTGAGGGAAC  CCATCAGTCACTGT  GGGCCAAAGTCCCTG  CCGGCCACTGCCCAA  1890
Ron      CTCCAACTTCTACCT  TCACCCTTCTGGTCT  GGTGCCTGAGGGAAC  CCATCAGTCACTGT  GGGCCAAAGTCCCTG  CCGGCCACTGCCCAA  1890

Ron-V3   GGACAGCTCAAAACT  CAGACCAGTGCCCCG  GAAAGACTTTGTAGA  GGAGTTTGAGTGTGA  ACTGGAGCCCTTGGG  CACCCAGGCAGTGGG  1980
Ron-V2   GGACAGCTCAAAACT  CAGACCAGTGCCCCG  GAAAGACTTTGTAGA  GGAGTTTGAGTGTGA  ACTGGAGCCCTTGGG  CACCCAGGCAGTGGG  1980
Ron-V1   GGACAGCTCAAAACT  CAGACCAGTGCCCCG  GAAAGACTTTGTAGA  GGAGTTTGAGTGTGA  ACTGGAGCCCTTGGG  CACCCAGGCAGTGGG  1980
Ron      GGACAGCTCAAAACT  CAGACCAGTGCCCCG  GAAAGACTTTGTAGA  GGAGTTTGAGTGTGA  ACTGGAGCCCTTGGG  CACCCAGGCAGTGGG  1980

Ron-V3   GCCTACCAACGTCAG  CCTCACCGTGACTAA  CATGCCACCGGGCAA  GCACTTCCGGGTAGA  CGGCACCTCCGTGCT  GAGAGGCTTCTCTTT  2070
Ron-V2   GCCTACCAACGTCAG  CCTCACCGTGACTAA  CATGCCACCGGGCAA  GCACTTCCGGGTAGA  CGGCACCTCCGTGCT  GAGAGGCTTCTCTTT  2070
Ron-V1   GCCTACCAACGTCAG  CCTCACCGTGACTAA  CATGCCACCGGGCAA  GCACTTCCGGGTAGA  CGGCACCTCCGTGCT  GAGAGGCTTCTCTTT  2070
Ron      GCCTACCAACGTCAG  CCTCACCGTGACTAA  CATGCCACCGGGCAA  GCACTTCCGGGTAGA  CGGCACCTCCGTGCT  GAGAGGCTTCTCTTT  2070

Ron-V3   CATGGAGCCAGTGCT  GATAGCAGTGCAACC  CCTCTTTGGCCCACG  GGCAGGAGGCACCTG  TCTCACTCTTGAAGG  CCAGAGTCTGTCTGT  2160
Ron-V2   CATGGAGCCAGTGCT  GATAGCAGTGCAACC  CCTCTTTGGCCCACG  GGCAGGAGGCACCTG  TCTCACTCTTGAAGG  CCAGAGTCTGTCTGT  2160
Ron-V1   CATGGAGCCAGTGCT  GATAGCAGTGCAACC  CCTCTTTGGCCCACG  GGCAGGAGGCACCTG  TCTCACTCTTGAAGG  CCAGAGTCTGTCTGT  2160
Ron      CATGGAGCCAGTGCT  GATAGCAGTGCAACC  CCTCTTTGGCCCACG  GGCAGGAGGCACCTG  TCTCACTCTTGAAGG  CCAGAGTCTGTCTGT  2160

Ron-V3   AGGCACCAGCCGGGC  TGTGCTGGTCAATGG  GACTGAGTGTCTGCT  AGCACGGGTCAGTGA  GGGGCAGCTTTTATG  TGCCACACCCCCTGG  2250
Ron-V2   AGGCACCAGCCGGGC  TGTGCTGGTCAATGG  GACTGAGTGTCTGCT  AGCACGGGTCAGTGA  GGGGCAGCTTTTTATG TGCCACACCCCCTGG  2250
Ron-V1   AGGCACCAGCCGGGC  TGTGCTGGTCAATGG  GACTGAGTGTCTGCT  AGCACGGGTCAGTGA  GGGGCAGCTTTTATG  TGCCACACCCCCTGG  2250
Ron      AGGCACCAGCCGGGC  TGTGCTGGTCAATGG  GACTGAGTGTCTGCT  AGCACGGGTCAGTGA  GGGGCAGCTTTTATG  TGCCACACCCCCTGG  2250
```

FIG. 5-6    SEQ ID NOs: 2, 4, 6, 8 cont.

```
Ron-V3    GGCCACGGTGGCCAG TGTCCCCCTTAGCCT GCAGGTGGGGGGTGC CCAGGTACCTGGTTC CTGGACCTTCCAGTA CAGAGAAGACCCTGT    2340
Ron-V2    GGCCACGGTGGCCAG TGTCCCCCTTAGCCT GCAGGTGGGGGGTGC CCAGGTACCTGGTTC CTGGACCTTCCAGTA CAGAGAAGACCCTGT    2340
Ron-V1    GGCCACGGTGGCCAG TGTCCCCCTTAGCCT GCAGGTGGGGGGTGC CCAGGTACCTGGTTC CTGGACCTTCCAGTA CAGAGAAGACCCTGT    2340
Ron       GGCCACGGTGGCCAG TGTCCCCCTTAGCCT GCAGGTGGGGGGTGC CCAGGTACCTGGTTC CTGGACCTTCCAGTA CAGAGAAGACCCTGT    2340

Ron-V3    CGTGCTAAGCATCAG CCCCAACTGTGGCTA CATCAACTCCCACAT CACCATCTGTGGCCA GCATCTAACTTCAGC ATGGCACTTAGTGCT    2430
Ron-V2    CGTGCTAAGCATCAG CCCCAACTGTGGCTA CATCAACTCCCACAT CACCATCTGTGGCCA GCATCTAACTTCAGC ATGGCACTTAGTGCT    2430
Ron-V1    CGTGCTAAGCATCAG CCCCAACTGTGGCTA CATCAACTCCCACAT CACCATCTGTGGCCA GCATCTAACTTCAGC ATGGCACTTAGTGCT    2430
Ron       CGTGCTAAGCATCAG CCCCAACTGTGGCTA CATCAACTCCCACAT CACCATCTGTGGCCA GCATCTAACTTCAGC ATGGCACTTAGTGCT    2430

Ron-V3    GTCATTCCATGACGG GCTTAGGGCAGTGGA AAGCAGGTGTGAGAG GCAGCTTCCAGAGCA GCAGCTGTGCCGCCT TCCTGAATATGTGGT    2520
Ron-V2    GTCATTCCATGACGG GCTTAGGGCAGTGGA AAGCAGGTGTGAGAG GCAGCTTCCAGAGCA GCAGCTGTGCCGCCT TCCTGAATATGTGGT    2520
Ron-V1    GTCATTCCATGACGG GCTTAGGGCAGTGGA AAGCAGGTGTGAGAG GCAGCTTCCAGAGCA GCAGCTGTGCCGCCT TCCTGAATATGTGGT    2520
Ron       GTCATTCCATGACGG GCTTAGGGCAGTGGA AAGCAGGTGTGAGAG GCAGCTTCCAGAGCA GCAGCTGTGCCGCCT TCCTGAATATGTGGT    2520

Ron-V3    CCGAGACCCCCAGGG ATGGGTGGCAGGGAA TCTGAGTGCCCGAGG GGATGGAGCTGCTGG CTTTACACTGCCTGG CTTTCGCTTCCTACC    2610
Ron-V2    CCGAGACCCCCAGGG ATGGGTGGCAGGGAA TCTGAGTGCCCGAGG GGATGGAGCTGCTGG CTTTACACTGCCTGG CTTTCGCTTCCTACC    2610
Ron-V1    CCGAGACCCCCAGGG ATGGGTGGCAGGGAA TCTGAGTGCCCGAGG GGATGGAGCTGCTGG CTTTACACTGCCTGG CTTTCGCTTCCTACC    2610
Ron       CCGAGACCCCCAGGG ATGGGTGGCAGGGAA TCTGAGTGCCCGAGG GGATGGAGCTGCTGG CTTTACACTGCCTGG CTTTCGCTTCCTACC    2610

Ron-V3    CCCACCCCATCCACC CAGTGCCAACCTAGT TCCACTGAAGCCTGA GGAGCATGCCATTAA GTTTGAG-------- ---------------    2690
Ron-V2    CCCACCCCATCCACC CAGTGCCAACCTAGT TCCACTGAAGCCTGA GGAGCATGCCATTAA GTTTGAG-------- ---------------    2677
Ron-V1    CCCACCCCATCCACC CAGTGCCAACCTAGT TCCACTGAAGCCTGA GGAGCATGCCATTAA GTTTGAGTATATTGG GCTGGGCGCTGTGGC    2700
Ron       CCCACCCCATCCACC CAGTGCCAACCTAGT TCCACTGAAGCCTGA GGAGCATGCCATTAA GTTTGAGTAGTATATTGG GCTGGGCGCTGTGGC    2700
```

FIG. 5-7   SEQ ID NOs: 2, 4, 6, 8 cont.

```
Ron-V3   ------------  ------------  ------------  ------------  ------------  ------------  ------------  ------------   2690
Ron-V2   ------------  ------------  ------------  ------------  ------------  ------------  ------------  -----CCCCATC   2677
Ron-V1   TGACTGTGTGGGTAT CAACGTGACCGTGGG TGGTGAGAGCTGCCA GCACGAGTTCCGGGG GGACATGGTTGTCTG CCCCCTGCCCCATC   2790
Ron      TGACTGTGTGGGTAT CAACGTGACCGTGGG TGGTGAGAGCTGCCA GCACGAGTTCCGGGG GGACATGGTTGTCTG CCCCCTGCCCCATC   2790

Ron-V3   ------------  ----GTCTGCGTAGA TG----------  ------------  ------------  ------------   2690
Ron-V2   -----CTTGGCCA GGATGGTGCCCCATT GCAGGTCTGCGTAGA TG----------  ------------  ------------  ------------  ------------   2717
Ron-V1   CCTGCAGCTTGGCCA GGATGGTGCCCCATT GCAGGTCTGCGTAGA TG----------  ------------  ------------  ------------  ------------   2837
Ron      CCTGCAGCTTGGCCA GGATGGTGCCCCATT GCAGGTCTGCGTAGA TGGTGAATGTCATAT CCTGGGTAGAGTGGT GCGGCCAGGGCCAGA   2880

Ron-V3   ------------  ------------  ------------  ------------  ------------  ------------   2690
Ron-V2   ------------  ------------  ------------  ------------  ------------  ------------  ------------  ------------   2717
Ron-V1   ------------  ------------  ------------  ------------  ------------  ------------  ------------  ------------   2837
Ron      TGGGGTCCCACAGAG CACGCTCCTTGGTAT CCTGCTGCCTTTGCT GCTGCTTGTGGCTGC ACTGGCGACTGCACT GGTCTTCAGCTACTG   2970

Ron-V3   ------------  ------------  ------------  ------------  ------------  ------------  ------------  ------------   2690
Ron-V2   ------------  ------------  ------------  ------------  ------------  ------------  ------------  ------------   2717
Ron-V1   ------------  ------------  ------------  ------------  ------------  ------------  ------------  ------------   2837
Ron      GTGGCCGAGGAAGCA GCTAGTTCTTCCTCC CAACCTGAATGACCT GGCATCCCTGGACCA GACTGCTGGAGCCAC ACCCCTGCCTATTCT   3060

Ron-V3   ------------  ------------  --CACTCCCTGCCAT TGATGGTCTGGATTC CACCACTTGTGTCCA TGGAGCATCCTTCTC   2748
Ron-V2   ------------  ------------  --CACTCCCTGCCAT TGATGGTCTGGATTC CACCACTTGTGTCCA TGGAGCATCCTTCTC   2775
Ron-V1   ------------  ------------  --CACTCCCTGCCAT TGATGGTCTGGATTC CACCACTTGTGTCCA TGGAGCATCCTTCTC   2895
Ron      GTACTCGGGCTCTGA CTACAGAAGTGGCCT TGCACTCCCTGCCAT TGATGGTCTGGATTC CACCACTTGTGTCCA TGGAGCATCCTTCTC   3150
```

FIG. 5-8    SEQ ID NOs: 2, 4, 6, 8 cont.

```
Ron-V3  CGATAGTGAAGATGA ATCCTGTGTGCCACT GCTGCGGAAAGAGTC CATCCAGCTAAGGGA CCTGGACTCTGCGCT CTTGGCTGAGGTCAA  2838
Ron-V2  CGATAGTGAAGATGA ATCCTGTGTGCCACT GCTGCGGAAAGAGTC CATCCAGCTAAGGGA CCTGGACTCTGCGCT CTTGGCTGAGGTCAA  2865
Ron-V1  CGATAGTGAAGATGA ATCCTGTGTGCCACT GCTGCGGAAAGAGTC CATCCAGCTAAGGGA CCTGGACTCTGCGCT CTTGGCTGAGGTCAA  2985
Ron     CGATAGTGAAGATGA ATCCTGTGTGCCACT GCTGCGGAAAGAGTC CATCCAGCTAAGGGA CCTGGACTCTGCGCT CTTGGCTGAGGTCAA  3240

Ron-V3  GGATGTGCTGATTCC CACCCACAGTGACCG AGTCATTGGCAAAGG CCACTTTGGAGTTGT CTACCACGGAGAATA  2928
Ron-V2  GGATGTGCTGATTCC CACCCACAGTGACCG AGTCATTGGCAAAGG CCACTTTGGAGTTGT CTACCACGGAGAATA  2955
Ron-V1  GGATGTGCTGATTCC CACCCACAGTGACCG AGTCATTGGCAAAGG CCACTTTGGAGTTGT CTACCACGGAGAATA  3075
Ron     GGATGTGCTGATTCC CACCCACAGTGACCG AGTCATTGGCAAAGG CCACTTTGGAGTTGT CTACCACGGAGAATA  3330

Ron-V3  CATAGACCAGGCCCA GAATCGAATCCAATG TGCCATCAAGTCACT AAGTCGCATCACAGA GATGCAGCAGGTGCA GGCCTTCCTGCGAGA  3018
Ron-V2  CATAGACCAGGCCCA GAATCGAATCCAATG TGCCATCAAGTCACT AAGTCGCATCACAGA GATGCAGCAGGTGGA GGCCTTCCTGCGAGA  3045
Ron-V1  CATAGACCAGGCCCA GAATCGAATCCAATG TGCCATCAAGTCACT AAGTCGCATCACAGA GATGCAGCAGGTGGA GGCCTTCCTGCGAGA  3165
Ron     CATAGACCAGGCCCA GAATCGAATCCAATG TGCCATCAAGTCACT AAGTCGCATCACAGA GATGCAGCAGGTGGA GGCCTTCCTGCGAGA  3420

Ron-V3  GGGGCTGCTCATGCG TGGCCTGAACCACCC GAATGTGCTGGCTCT CATTGGTATCATGTT GCCACCTGAGGGCCT GCCCCATGTGCTGCT  3108
Ron-V2  GGGGCTGCTCATGCG TGGCCTGAACCACCC GAATGTGCTGGCTCT CATTGGTATCATGTT GCCACCTGAGGGCCT GCCCCATGTGCTGCT  3135
Ron-V1  GGGGCTGCTCATGCG TGGCCTGAACCACCC GAATGTGCTGGCTCT CATTGGTATCATGTT GCCACCTGAGGGCCT GCCCCATGTGCTGCT  3255
Ron     GGGGCTGCTCATGCG TGGCCTGAACCACCC GAATGTGCTGGCTCT CATTGGTATCATGTT GCCACCTGAGGGCCT GCCCCATGTGCTGCT  3510

Ron-V3  GCCCTATATGTGCCA CGGTGACCTGCTCCA GTTCATCCGCTCACC TCAGCGGAACCCCAC CGTGAAGGACCTCAT CAGCTTTGGCCTGCA  3198
Ron-V2  GCCCTATATGTGCCA CGGTGACCTGCTCCA GTTCATCCGCTCACC TCAGCGGAACCCCAC CGTGAAGGACCTCAT CAGCTTTGGCCTGCA  3225
Ron-V1  GCCCTATATGTGCCA CGGTGACCTGCTCCA GTTCATCCGCTCACC TCAGCGGAACCCCAC CGTGAAGGACCTCAT CAGCTTTGGCCTGCA  3345
Ron     GCCCTATATGTGCCA CGGTGACCTGCTCCA GTTCATCCGCTCACC TCAGCGGAACCCCAC CGTGAAGGACCTCAT CAGCTTTGGCCTGCA  3600
```

FIG. 5-9  SEQ ID NOs: 2, 4, 6, 8 cont.

```
Ron-V3  GGTAGCCCGCGGGCAT GGAGTACCTGGCAGA GCAGAAGTTTGTGCA CAGGGACCTGGCTGC GCGGAACTGCATGCT GGACGAGTCATTCAC  3288
Ron-V2  GGTAGCCCGCGGGCAT GGAGTACCTGGCAGA GCAGAAGTTTGTGCA CAGGGACCTGGCTGC GCGGAACTGCATGCT GGACGAGTCATTCAC  3315
Ron-V1  GGTAGCCCGCGGGCAT GGAGTACCTGGCAGA GCAGAAGTTTGTGCA CAGGGACCTGGCTGC GCGGAACTGCATGCT GGACGAGTCATTCAC  3435
Ron     GGTAGCCCGCGGGCAT GGAGTACCTGGCAGA GCAGAAGTTTGTGCA CAGGGACCTGGCTGC GCGGAACTGCATGCT GGACGAGTCATTCAC  3690

Ron-V3  AGTCAAGGTGGCTGA CTTTGGTTTGGCCCG CGACATCCTGGACAG GGAGTACTATAGTGT TCAACAGCATCGCCA CGCTCGCCTACCTGT  3378
Ron-V2  AGTCAAGGTGGCTGA CTTTGGTTTGGCCCG CGACATCCTGGACAG GGAGTACTATAGTGT TCAACAGCATCGCCA CGCTCGCCTACCTGT  3405
Ron-V1  AGTCAAGGTGGCTGA CTTTGGTTTGGCCCG CGACATCCTGGACAG GGAGTACTATAGTGT TCAACAGCATCGCCA CGCTCGCCTACCTGT  3525
Ron     AGTCAAGGTGGCTGA CTTTGGTTTGGCCCG CGACATCCTGGACAG GGAGTACTATAGTGT TCAACAGCATCGCCA CGCTCGCCTACCTGT  3780

Ron-V3  GAAGTGGATGGCGCT GGAGAGCCTGCAGAC CTATAGATTACCAC CAAGTCTGATGTG-- ---------------- ----------------  3436
Ron-V2  GAAGTGGATGGCGCT GGAGAGCCTGCAGAC CTATAGATTACCAC CAAGTCTGATGTG-- ---------------- ----------------  3463
Ron-V1  GAAGTGGATGGCGCT GGAGAGCCTGCAGAC CTATAGATTACCAC CAAGTCTGATGTG-- ---------------- ----------------  3583
Ron     GAAGTGGATGGCGCT GGAGAGCCTGCAGAC CTATAGATTACCAC CAAGTCTGATGTGTG GTCATTGGTGTGCT GCTGTGGGAACTGCT  3870

Ron-V3  ---------------- ---------------- ---------------- ---------------- ---------------- ----------------  3436
Ron-V2  ---------------- ---------------- ---------------- ---------------- ---------------- ----------------  3463
Ron-V1  ---------------- ---------------- ---------------- ---------------- ---------------- ----------------  3583
Ron     GACACGGGGTGCCCC ACCATACCGCCACAT TGACCCCTTTTGACCT TACCCACTTCCTGGC CCAGGGTCGGCGCCT GCCCCAGCCTGAGTA  3960

Ron-V3  ---------------- GTACCAAGTGATGCA GCAATGCTGGGAGGC AGACCCAGCAGTGCG ACCCACCTTCAGAGT ACTAGTGGGGAGGT  3511
Ron-V2  ---------------- GTACCAAGTGATGCA GCAATGCTGGGAGGC AGACCCAGCAGTGCG ACCCACCTTCAGAGT ACTAGTGGGGAGGT  3538
Ron-V1  ---------------- GTACCAAGTGATGCA GCAATGCTGGGAGGC AGACCCAGCAGTGCG ACCCACCTTCAGAGT ACTAGTGGGGAGGT  3658
Ron     TTGCCCTGATTCTCT GTACCAAGTGATGCA GCAATGCTGGGAGGC AGACCCAGCAGTGCG ACCCACCTTCAGAGT ACTAGTGGGGAGGT  4050
```

FIG. 5-10     SEQ ID NOs: 2, 4, 6, 8 cont.

```
Ron-V3  GGAGCAGATAGTGTC TGCACTGCTTGGGGA CCATTATGTGCAGCT GCCAGCAACCTACAT GAACTTG---------------                                 3578
Ron-V2  GGAGCAGATAGTGTC TGCACTGCTTGGGGA CCATTATGTGCAGCT GCCAGCAACCTACAT GAACTTG---------------                                 3605
Ron-V1  GGAGCAGATAGTGTC TGCACTGCTTGGGGA CCATTATGTGCAGCT GCCAGCAACCTACAT GAACTTG---------------                                 3725
Ron     GGAGCAGATAGTGTC TGCACTGCTTGGGGA CCATTATGTGCAGCT GCCAGCAACCTACAT GAACTTGGGCCCCAG CACCTCGCATGAGAT                       4140

Ron-V3  --------------- --------------- --------------- --------------- ---------------                                         3578
Ron-V2  --------------- --------------- --------------- --------------- ---------------                                         3605
Ron-V1  --------------- --------------- --------------- --------------- ---------------                                         3725
Ron     GAATGTGCGTCCAGA ACAGCCGCAGTTCTC ACCCATGCCAGGAA TGTACGCCGGCCCCG GCCACTCTCAGAGCC TCCTCGCCCACTTG                           4230

Ron-V3  --------------- --------------- -------AGCTAACCC CAAGGCTGCCTCTGG GCCATGCCAGGCCAG AGCAGTGGCCCTCCA                        3632
Ron-V2  --------------- --------------- -------AGCTAACCC CAAGGCTGCCTCTGG GCCATGCCAGGCCAG AGCAGTGGCCCTCCA                        3659
Ron-V1  --------------- --------------- -------AGCTAACCC CAAGGCTGCCTCTGG GCCATGCCAGGCCAG AGCAGTGGCCCTCCA                        3779
Ron     ACTTAGTTCTTGGGC TGGACCTGCTTAGCT GCCTTGAGCTAACCC CAAGGCTGCCTCTGG GCCATGCCAGGCCAG AGCAGTGGCCCTCCA                        4320

Ron-V3  CCTTGTTCCTGCCCT TTAACTTTCAGAGGC AATAGGTAAATGGGC CCATTAGTGTCCCTCA CTCCACAGAGTGAGC CAGTGAGGGCAGTCC                          3722
Ron-V2  CCTTGTTCCTGCCCT TTAACTTTCAGAGGC AATAGGTAAATGGGC CCATTAGTGTCCCTCA CTCCACAGAGTGAGC CAGTGAGGGCAGTCC                          3749
Ron-V1  CCTTGTTCCTGCCCT TTAACTTTCAGAGGC AATAGGTAAATGGGC CCATTAGTGTCCCTCA CTCCACAGAGTGAGC CAGTGAGGGCAGTCC                          3869
Ron     CCTTGTTCCTGCCCT TTAACTTTCAGAGGC AATAGGTAAATGGGC CCATTAGTGTCCCTCA CTCCACAGAGTGAGC CAGTGAGGGCAGTCC                          4410

Ron-V3  TGCAACATGTATTTA TGGAGTGCCTGCTGT GGACCCTGTCTTCTG GGCACAGTGGACTCA GCAGTGACCACACCA ACACTGACCCTTGAA                           3812
Ron-V2  TGCAACATGTATTTA TGGAGTGCCTGCTGT GGACCCTGTCTTCTG GGCACAGTGGACTCA GCAGTGACCACACCA ACACTGACCCTTGAA                           3839
Ron-V1  TGCAACATGTATTTA TGGAGTGCCTGCTGT GGACCCTGTCTTCTG GGCACAGTGGACTCA GCAGTGACCACACCA ACACTGACCCTTGAA                           3959
Ron     TGCAACATGTATTTA TGGAGTGCCTGCTGT GGACCCTGTCTTCTG GGCACAGTGGACTCA GCAGTGACCACACCA ACACTGACCCTTGAA                           4500
```

FIG 5-11    SEQ ID NOs: 2, 4, 6, 8 cont.

```
Ron-V3  CCAATAAAGGAACAA ATGACTATTAAAGCA CAAAAAAAAAA  3853
Ron-V2  CCAATAAAGGAACAA ATGACTATTAAAGCA CAAAAAAAAAA  3880
Ron-V1  CCAATAAAGGAACAA ATGACTATTAAAGCA CAAAAAAAAAA  4000
Ron     CCAATAAAGGAACAA ATGACTATTAAAGCA CAAAAAAAAAA  4541
```

FIG. 6-1

```
Ron-V3   MELLPPLPQSFLLLL LLPAKPAAGEDWQCP RTPYAASRDFDVKYV VPSFSAGGLVQAMVT YEGDRNESAVFVAIR NRLHVLGPDLKSVQS    90
Ron-V2   MELLPPLPQSFLLLL LLPAKPAAGEDWQCP RTPYAASRDFDVKYV VPSFSAGGLVQAMVT YEGDRNESAVFVAIR NRLHVLGPDLKSVQS    90
Ron-V1   MELLPPLPQSFLLLL LLPAKPAAGEDWQCP RTPYAASRDFDVKYV VPSFSAGGLVQAMVT YEGDRNESAVFVAIR NRLHVLGPDLKSVQS    90
Ron      MELLPPLPQSFLLLL LLPAKPAAGEDWQCP RTPYAASRDFDVKYV VPSFSAGGLVQAMVT YEGDRNESAVFVAIR NRLHVLGPDLKSVQS    90

Ron-V3   LATGPAGDPGCQTCA ACGPGPHGPPGDTDT KVLVLDPALPALVSC GSSLQGRCFLHDLEP QGTAVHLAAPACLFS AHHNRPDDCPDCVAS   180
Ron-V2   LATGPAGDPGCQTCA ACGPGPHGPPGDTDT KVLVLDPALPALVSC GSSLQGRCFLHDLEP QGTAVHLAAPACLFS AHHNRPDDCPDCVAS   180
Ron-V1   LATGPAGDPGCQTCA ACGPGPHGPPGDTDT KVLVLDPALPALVSC GSSLQGRCFLHDLEP QGTAVHLAAPACLFS AHHNRPDDCPDCVAS   180
Ron      LATGPAGDPGCQTCA ACGPGPHGPPGDTDT KVLVLDPALPALVSC GSSLQGRCFLHDLEP QGTAVHLAAPACLFS AHHNRPDDCPDCVAS   180

Ron-V3   PLGTRVTVVEQGQAS YFYVASSLDAAVAGS FSPRSVSIRRLKADA SGFAPGFVALSVLPK HLVSYSIEYVHSFHT GAFVYFLTVQPASVT   270
Ron-V2   PLGTRVTVVEQGQAS YFYVASSLDAAVAGS FSPRSVSIRRLKADA SGFAPGFVALSVLPK HLVSYSIEYVHSFHT GAFVYFLTVQPASVT   270
Ron-V1   PLGTRVTVVEQGQAS YFYVASSLDAAVAGS FSPRSVSIRRLKADA SGFAPGFVALSVLPK HLVSYSIEYVHSFHT GAFVYFLTVQPASVT   270
Ron      PLGTRVTVVEQGQAS YFYVASSLDAAVAGS FSPRSVSIRRLKADA SGFAPGFVALSVLPK HLVSYSIEYVHSFHT GAFVYFLTVQPASVT   270

Ron-V3   DDPSALHTRLARLSA TEPELGDYRELVLDC RFAPKRRRRGAPEGG QPYPVLQVAHSAPVG AQLATELSIAEGQEV LFGVFVTGKDGGPGV   360
Ron-V2   DDPSALHTRLARLSA TEPELGDYRELVLDC RFAPKRRRRGAPEGG QPYPVLQVAHSAPVG AQLATELSIAEGQEV LFGVFVTGKDGGPGV   360
Ron-V1   DDPSALHTRLARLSA TEPELGDYRELVLDC RFAPKRRRRGAPEGG QPYPVLQVAHSAPVG AQLATELSIAEGQEV LFGVFVTGKDGGPGV   360
Ron      DDPSALHTRLARLSA TEPELGDYRELVLDC RFAPKRRRRGAPEGG QPYPVLQVAHSAPVG AQLATELSIAEGQEV LFGVFVTGKDGGPGV   360

Ron-V3   GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
Ron-V2   GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
Ron-V1   GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
Ron      GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
```

FIG. 6-2

```
Ron-V3  LYVTRLDNVTVAHMG TMDGRILQVELVRSL NYLLYVSNFSLGDSG QPVQRDVSRLGDHLL FASGDQVFQVPIRGP GCRHFLTCGRCLRAW  540
Ron-V2  LYVTRLDNVTVAHMG TMDGRILQVELVRSL NYLLYVSNFSLGDSG QPVQRDVSRLGDHLL FASGDQVFQVPIRGP GCRHFLTCGRCLRAW  540
Ron-V1  LYVTRLDNVTVAHMG TMDGRILQVELVRSL NYLLYVSNFSLGDSG QPVQRDVSRLGDHLL FASGDQVFQVPIRGP GCRHFLTCGRCLRAW  540
Ron     LYVTRLDNVTVAHMG TMDGRILQVELVRSL NYLLYVSNFSLGDSG QPVQRDVSRLGDHLL FASGDQVFQVPIRGP GCRHFLTCGRCLRAW  540

Ron-V3  HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630
Ron-V2  HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630
Ron-V1  HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630
Ron     HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630

Ron-V3  RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720
Ron-V2  RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720
Ron-V1  RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720
Ron     RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720

Ron-V3  GTECLLARVSEGQLL CATPPGATVASVPLS LQVGGAQVPGSWTFQ YREDPVVLSISPNCG YINSHITICGQHLTS AWHLVLSFHDGLRAV  810
Ron-V2  GTECLLARVSEGQLL CATPPGATVASVPLS LQVGGAQVPGSWTFQ YREDPVVLSISPNCG YINSHITICGQHLTS AWHLVLSFHDGLRAV  810
Ron-V1  GTECLLARVSEGQLL CATPPGATVASVPLS LQVGGAQVPGSWTFQ YREDPVVLSISPNCG YINSHITICGQHLTS AWHLVLSFHDGLRAV  810
Ron     GTECLLARVSEGQLL CATPPGATVASVPLS LQVGGAQVPGSWTFQ YREDPVVLSISPNCG YINSHITICGQHLTS AWHLVLSFHDGLRAV  810

Ron-V3  ESRCERQLPEQQLCR LPEYVVRDPQGWVAG NLSARGDGAAGFTLP GFRFLPPHPPSANL  VPLKPEBHAIKFE--  ---------------  883
Ron-V2  ESRCERQLPEQQLCR LPEYVVRDPQGWVAG NLSARGDGAAGFTLP GFRFLPPHPPSANL  VPLKPEBHAIKFE--  ---------------  883
Ron-V1  ESRCERQLPEQQLCR LPEYVVRDPQGWVAG NLSARGDGAAGFTLP GFRFLPPHPPSANL  VPLKPEBHAIKFEYI GLGAVADCVGINVTV  900
Ron     ESRCERQLPEQQLCR LPEYVVRDPQGWVAG NLSARGDGAAGFTLP GFRFLPPHPPSANL  VPLKPEBHAIKFEYI GLGAVADCVGINVTV  900
```

FIG. 6-3

```
Ron-V3  ----------------  ----------------  --VCVD----------  ----------------  ----------------  ----------------   887
Ron-V2  ----------------  --------LGQDGAP   LQVCVD----------  ----------------  ----------------  ----------------   896
Ron-V1  GGESCQHEFRGDMVV   CPLPPSLQLGQDGAP   LQVCVD----------  ----------------  ----------------  ----------------   936
Ron     GGESCQHEFRGDMVV   CPLPPSLQLGQDGAP   LQVCVDGECHILGRV   VRPGPDGVPQSTLLG   ILLPLLLLVAALATA   LVFSYWWRKQLVLP    990

Ron-V3  ----------------  -ALPAIDGLDSTTCV   HGASFSDSEDESCVP   LLRKESIQLRDLDSA   LLAEVKDVLIPHERV                      946
Ron-V2  ----------------  -ALPAIDGLDSTTCV   HGASFSDSEDESCVP   LLRKESIQLRDLDSA   LLAEVKDVLIPHERV                      955
Ron-V1  ----------------  -ALPAIDGLDSTTCV   HGASFSDSEDESCVP   LLRKESIQLRDLDSA   LLAEVKDVLIPHERV                      995
Ron     PNLNDLASLDQTAGA   TPLPILYSGSDYRSG   LALPAIDGLDSTTCV   HGASFSDSEDESCVP   LLRKESIQLRDLDSA   LLAEVKDVLIPHERV   1080

Ron-V3  VTHSDRVIGKGHFGV   VYHGEYIDQAQNRIQ   CAIKSLSRITEMQQV   EAFLREGLLMRGLNH   PNVLALIGIMLPPEG   LPHVLLPYMCHGDLL   1036
Ron-V2  VTHSDRVIGKGHFGV   VYHGEYIDQAQNRIQ   CAIKSLSRITEMQQV   EAFLREGLLMRGLNH   PNVLALIGIMLPPEG   LPHVLLPYMCHGDLL   1045
Ron-V1  VTHSDRVIGKGHFGV   VYHGEYIDQAQNRIQ   CAIKSLSRITEMQQV   EAFLREGLLMRGLNH   PNVLALIGIMLPPEG   LPHVLLPYMCHGDLL   1085
Ron     VTHSDRVIGKGHFGV   VYHGEYIDQAQNRIQ   CAIKSLSRITEMQQV   EAFLREGLLMRGLNH   PNVLALIGIMLPPEG   LPHVLLPYMCHGDLL   1170

Ron-V3  QFIRSPQRNPTVKDL   ISFGLQVARGMEYLA   EQKFVHRDLAARNCM   LDESFTVKVADFGLA   RDILDREYYSVQQHR   HARLPVKWMALESLQ   1126
Ron-V2  QFIRSPQRNPTVKDL   ISFGLQVARGMEYLA   EQKFVHRDLAARNCM   LDESFTVKVADFGLA   RDILDREYYSVQQHR   HARLPVKWMALESLQ   1135
Ron-V1  QFIRSPQRNPTVKDL   ISFGLQVARGMEYLA   EQKFVHRDLAARNCM   LDESFTVKVADFGLA   RDILDREYYSVQQHR   HARLPVKWMALESLQ   1175
Ron     QFIRSPQRNPTVKDL   ISFGLQVARGMEYLA   EQKFVHRDLAARNCM   LDESFTVKVADFGLA   RDILDREYYSVQQHR   HARLPVKWMALESLQ   1260

Ron-V3  TYRFTTKSDVVPSD-   ----------------  ----------------  ----------------  ----------------  -----AAMLG         1145
Ron-V2  TYRFTTKSDVVPSD-   ----------------  ----------------  ----------------  ----------------  -----AAMLG         1154
Ron-V1  TYRFTTKSDVVPSD-   ----------------  ----------------  ----------------  ----------------  -----AAMLG         1194
Ron     TYRFTTKSDVWSFGV   LLWELLITRGAPPYRH  IDPFDLTHFLAQGRR   LPQPEYCPDSLYQVM   QQCWEADPAVRPTFR   VLVGEVEQIVSALLG   1350
```

FIG. 6-4

```
Ron-V3  GR----PSSATHLQS TSGGGGADSVCTAWG PLCAAASNLHELELT PRLPLGHARPEQWPS TLFLPFNFQRQ----- ----- 1212
Ron-V2  GR----PSSATHLQS TSGGGGADSVCTAWG PLCAAASNLHELELT PRLPLGHARPEQWPS TLFLPFNFQRQ----- ----- 1221
Ron-V1  GR----PSSATHLQS TSGGGGADSVCTAWG PLCAAASNLHELELT PRLPLGHARPEQWPS TLFLPFNFQRQ----- ----- 1261
Ron     DHYVQLPATYMNL-- -------------G P-----STSHEM--- ------NVRPEQ-PQ FSPMPGNVRRPRPLS EPPRPT 1400
```

HUMAN RON-RELATED GENE VARIANT ASSOCIATED WITH CANCERS

FIELD OF THE INVENTION

The invention relates to the nucleic acid and polypeptide sequences of a novel human Ron-related gene variant, preparation process thereof, and uses of the same in diagnosing cancers, in particular, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

BACKGROUND OF THE INVENTION

Cancer is one of the major causes of death in the world. According to the report from the WHO Fact Sheet-Cancer (2003), cancer accounts for 7.1 million (12.6% of the global total) deaths annually and new cancer cases are expected to be increased from 10 million people in 2000 to 15 million people by 2020. In recent years, much progress has been made toward understanding the molecular and cellular biology of cancers. Many important contributions have been made by the identification of several key genetic factors associated with cancers. However, the treatments of cancers still mainly depend on surgery, chemotherapy and radiotherapy because the molecular mechanisms underlying the pathogenesis of cancers remain largely unclear.

It is interesting to note that receptor tyrosine kinases are a family of proteins reported to be involved in many fundamental cellular processes such as cell cycle, signalling transduction, proliferation, differentiation, adhesion, migration, and apoptosis. An important role of the receptor tyrosine kinases in the development of cancers has been reported previously. Therefore, future strategies for the prevention and treatment of cancers may be focused on the elucidation of the receptor tyrosine kinases which are involved in the pathogenesis of cancers. Ron, a member of the receptor tyrosine kinase family located on human chromosome 3p21 (a region frequently deleted in small cell lung carcinoma), was isolated and identified through the screening of cDNA libraries. Previous studies have indicated that Ron is involved in many genetic mechanisms of the tumor cells (Wang et al., (2003) Carcinogenesis 24:1291-300; Angeloni et al., (2004) J Biol Chem. 279:3726-32; Peace et al., (2005) Cancer Res. 65:1285-93; Camp et al., (2005) Ann Surg Oncol. 12:273-81), and that Ron is a potential target for understanding the pathogenesis of cancers. In addition, the association between gene variants and diseases has been reported previously. Therefore, the discovery of gene variants of Ron may be important for the diagnostic markers of cancers.

SUMMARY OF THE INVENTION

The present invention provides one Ron-related gene variant present in human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. The nucleotide sequence of the gene variant and polypeptide sequence encoded thereby can be used for the diagnosis of any diseases associated with this gene variant or cancers, in particular, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

The invention further provides an expression vector and host cell for expressing the variant.

The invention further provides a method for producing the variant.

The invention further provides an antibody that specifically binds to the variant. For example, by selecting a sequence unique to one of the variants, e.g., a peptide fragment that spans one the deletion junctions, an antibody may be generated that binds to one of the variants and not to RON. Preferably, such peptide antigens are at least 17 amino acid long, but in some cases smaller peptides such as 10 mers, 12 mers, or 15 mers may suffice. Longer peptides, such as 20 mers, 50 mers, hundred-mers (and those therebetween) and even up to full length proteins may be used.

The invention also provides methods for detecting the presence of the variant in a mammal.

BRIEF DESCRIPTION OF THE DRAWINGS

FIG. 1 shows the nucleic acid sequence (SEQ ID NO:1), amino acid sequence (SEQ ID NO:2) and nucleic acid with corresponding amino acid sequence (SEQ ID NO: 1 & 2) of Ron.

FIG. 2 shows the nucleic acid sequence (SEQ ID NO:3), amino acid sequence (SEQ ID NO:4) and nucleic acid with corresponding amino acid sequence (SEQ ID NO: 3 & 4) of Ron-V1.

FIG. 3 shows the nucleic acid sequence (SEQ ID NO:5), amino acid sequence (SEQ ID NO:6) and nucleic acid with corresponding amino acid sequence (SEQ ID NO: 5 & 6) of Ron-V2.

FIG. 4 shows the nucleic acid sequence (SEQ ID NO:7), amino acid sequence (SEQ ID NO:8) and nucleic acid with corresponding amino acid sequence (SEQ ID NO: 7 & 8) of Ron-V3.

FIG. 5 shows the nucleotide sequence alignment between the human Ron gene (SEQ ID NO: 1) and its related gene variants (Ron-V1, Ron-V2, and Ron-V3, SEQ ID NO: ID 3, 5, 7).

FIG. 6 shows the amino acid sequence alignment between the human Ron protein (SEQ ID NO: 2) and its related gene variants (Ron-V1, Ron-V2, and Ron-V3) (SEQ ID NO: 4, 6, 8).

DETAILED DESCRIPTION OF THE INVENTION

Figure 7:
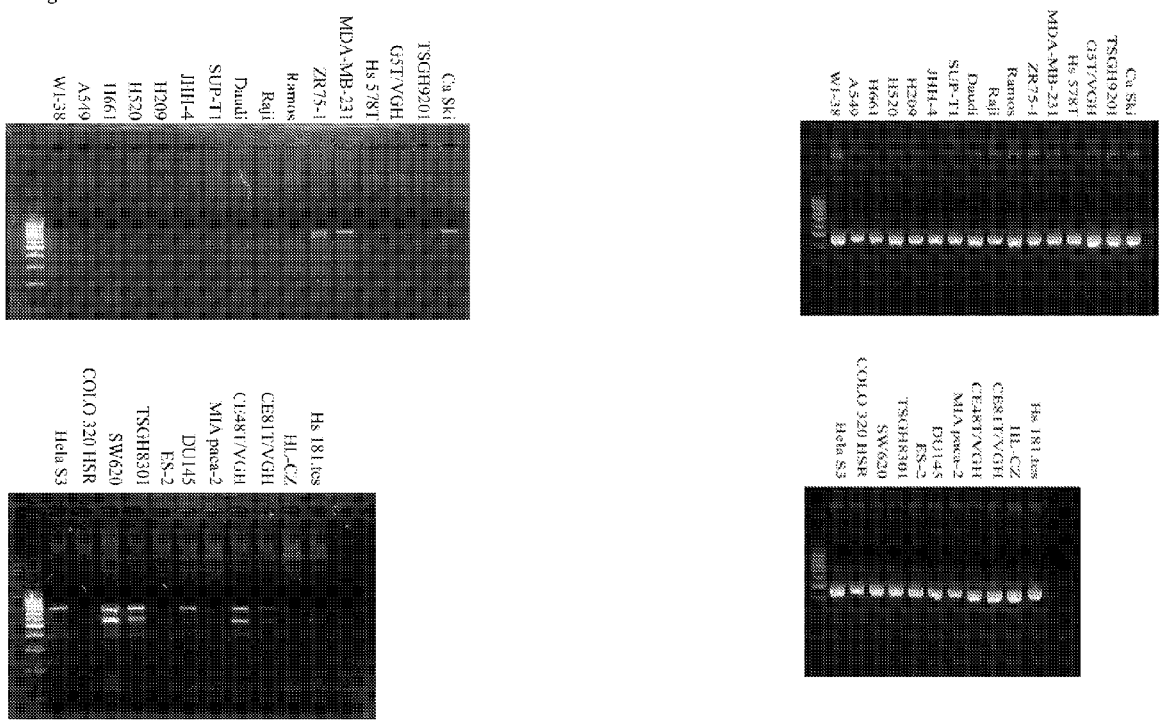
FIG. 7 shows the expression pattern of Ron gene variants in human cell lines.

All technical and scientific terms used herein, unless otherwise defined, have the same meanings as commonly understood by persons skilled in the art.

The term "antibody" used herein denotes intact molecules (a polypeptide or group of polypeptides) as well as fragments thereof, such as Fab, R(ab')2, and Fv fragments, which are capable of binding epitopes. Antibodies are produced by specialized B cells after stimulation by an antigen. Structurally, antibody consists of four subunits including two heavy chains and two light chains. The internal surface shape and charge distribution of the antibody binding domain is complementary to the features of an antigen. Thus, antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool ("BLAST")" (BLAST; Altschul et al., (1997) Nucleic Acids Res. 25: 3389-3402) used herein denotes programs for evaluation of homologies between a query sequence (amino or nucleic acid) and a test sequence. Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA" used herein denotes nucleic acids synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATG-GACTTACT-3' binds to the complementary sequence 5'-AG-TAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequence that derives from either 5' or 3' end of a cDNA.

The term "expression vector" used herein denotes nucleic acid constructs which contain a cloning site for introducing the DNA into vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR)" used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "polynucleotide" or "nucleic acid sequence" used herein denotes a sequence of nucleotide (guanine, cytosine, thymine or adenine) in a specific order that can be a natural or synthesized fragment of DNA or RNA. It may be single-stranded or double-stranded.

The term "protein" or "polypeptide" used herein denotes a sequence of amino acids in a specific order that can be encoded by a gene or by a recombinant DNA. It can also be chemically synthesized.

The term "RNA interference (RNAi)" used herein denotes an introduction of homologous double stranded RNA (dsRNA) into a cell to specifically inhibit the expression of a gene.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein denotes a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

According to the present invention, the polypeptides of one novel human Ron-related gene variant and the nucleic acid sequences encoding the same are provided.

According to the present invention, human Ron cDNA sequence was used to query the human EST databases using BLAST program to search for Ron-related gene variants. Three human cDNA partial sequences (i.e., EST) showing similar to Ron was identified from ESTs deposited in a cDNA database constructed using a SW620 (colon adenocarcinoma) cell line. The cDNA clones, named Ron-V1 (Ron variant 1), Ron-V2 (Ron variant 2), and Ron-V3 (Ron variant 3), were then isolated from the SW620 cDNA library and sequenced. FIGS. 2-4 show the nucleic acid sequences (SEQ ID NOs: 3, 5, & 7) of Ron-V1, Ron-V2, and Ron-V3 and its corresponding amino acid sequences (SEQ ID NOs: 4, 6, & 8) encoded thereby.

The full-length of the Ron-V1 cDNA is a 4000 bp clone containing a 3783 bp open reading frame (ORF) extending from 29 bp to 3811 bp, which corresponds to an encoded protein of 1261 amino acid residues with a predicted molecular mass of 136.1 kDa. The initiation ATG sequence of Ron-V1 is located at nucleotide 29-31 bp. The full-length of the Ron-V2 cDNA is a 3880 bp clone containing a 3663 bp open reading frame (ORF) extending from 29 bp to 3691 bp, which corresponds to an encoded protein of 1221 amino acid residues with a predicted molecular mass of 132 kDa. The initiation ATG sequence of Ron-V2 is located at nucleotide 29-31 bp. The full-length of the Ron-V3 cDNA is a 3853 bp clone containing a 3636 bp open reading frame (ORF) extending from 29 bp to 3664 bp, which corresponds to an encoded protein of 1212 amino acid residues with a predicted molecular mass of 131.1 kDa. The initiation ATG sequence of Ron-V3 is located at nucleotide 29-31 bp. To determine the variations in sequence of Ron-V1, Ron-V2 and Ron-V3 cDNA clones, an alignment of Ron nucleotide/amino acid sequence with Ron-V1, Ron-V2 and Ron-V3 was performed (FIGS. 5 and 6). The results indicate that (1) Ron-V1: three major genetic deletions were found in the aligned nucleotide sequences showing that Ron-V1 has a 255 bp, a 137 bp and a 149 bp deletions in the sequence of Ron from nucleotides 2838-3092, nucleotides 3839-3975 and nucleotides 4118-4266, respectively; (2) Ron-V2: four major genetic deletions were found in the aligned nucleotide sequences showing that Ron-V2 has a 120 bp, a 255 bp, a 137 bp and a 149 bp deletions in the sequence of Ron from nucleotides 2678-2797, nucleotides 2838-3092, nucleotides 3839-3975 and nucleotides 4118-4266, respectively; (3) Ron-V3: four major genetic deletions were found in the aligned nucleotide sequences showing that Ron-V3 has a 147 bp, a 255 bp, a 137 bp and a 149 bp deletions in the sequence of Ron from nucleotides 2678-2824, nucleotides 2838-3092, nucleotides 3839-3975 and nucleotides 4118-4266, respectively. Scanning Ron, Ron-V1, Ron-V2 and Ron-V3 amino acid sequences against protein profile databases including PROSITE (Motif Scan) indicated that Ron protein contains one Sema domain (31-522aa), one Protein_Kinase_ATP (1088-1114aa), one Protein_Kinase_TYR (1204-1216aa), and one Protein_Kinase_DOM (1082-1345aa). Ron-V1 protein contains one Sema domain (31-522aa), one Protein_Kinase_ATP (1003-1029aa), one Protein_Kinase_TYR (1119-1131aa), and one Protein_Kinase_DOM (997-1261aa). Ron-V2 protein contains one Sema domain (31-522aa), one Protein_Kinase_ATP (963-989aa), one Protein_Kinase_TYR (1079-1091aa), and one Protein_Kinase_DOM (957-1221aa). Ron-V3 protein contains one Sema domain (31-522aa), one Protein_Kinase ATP (954-980aa), one Protein_Kinase TYR (1070-1082aa), and one Protein_Kinase_DOM (948-1212aa).

In the present invention, a search of ESTs deposited in dbEST at NCBI was performed to determine the presence of Ron gene variants in silico. The result of in silico analysis showed that one EST (GenBank accession number BG823879) was found to confirm the absence of 255 bp region on Ron-V1, Ron-V2, and Ron-V3 nucleotide sequences; one EST (GenBank accession number AW009348) was found to confirm the absence of 137 bp region on Ron-V1, Ron-V2, and Ron-V3 nucleotide sequences. Therefore, any Ron nucleotide fragments containing the immediately upstream and downstream sequences of the deleted 255 bp region (2837-2838 bp of Ron-V1; 2717-2718 bp of Ron-V2; 2691-2692 bp of Ron-V3) and/or 137 bp region (3583-3584 bp of Ron-V1; 3463-3464 bp of Ron-V2; 3436-3437 bp of Ron-V3) and/or 149 bp region (3725-3726 bp of Ron-V1; 3605-3606 bp of Ron-V2; 3578-3579 bp of Ron-V3) are the "gene targets" which may be used as probes to determine the presence of Ron-V1, Ron-V2, and Ron-V3 under high stringency conditions. An alternative approach is that any set of primers for amplifying the fragment containing the immediately upstream and downstream sequences of the deleted 255 bp region (2837-2838 bp of Ron-V1; 2717-2718 bp of Ron-V2; 2691-2692 bp of Ron-V3) and/or 137 bp region (3583-3584 bp of Ron-V1; 3463-3464 bp of Ron-V2; 3436-3437 bp of Ron-V3) and/or 149 bp region (3725-3726 bp of Ron-V1; 3605-3606 bp of Ron-V2; 3578-3579 bp of Ron-V3) may be used for determining the presence of the variants (Ron-V1, Ron-V2, and Ron-V3). On the other hand, any Ron nucleotide fragments containing the immediately upstream and downstream sequences of the deleted 120 bp region (2678-2679 bp of Ron-V2) and 147 bp region (2678-2679 bp of Ron-V3) are the "gene targets" which may be used as probes for determining the presence of Ron-V2 and Ron-V3, respectively, under high stringency conditions. An alternative approach is that any set of primers for amplifying the fragment containing the immediately upstream and downstream sequences of the deleted 120 bp region (2678-2679 bp of Ron-V2) and 147 bp region (2678-2679 bp of Ron-V3) may be used for determining the presence of Ron-V2 and Ron-V3, respectively.

According to the present invention, the polypeptides of the human Ron-V1, Ron-V2, and Ron-V3 and its fragments thereof may be produced through genetic engineering techniques. In this case, they are produced by appropriate host cells which have been transformed by DNAs that encode for the polypeptides or fragments thereof. The nucleotide sequence encoding the polypeptide of the human Ron-V1, Ron-V2, and Ron-V3 or their fragments thereof are inserted into an appropriate expression vector, i.e., a vector which contains the necessary elements for the transcription and translation of the inserted coding sequence in a suitable host. The nucleic acid sequence is inserted into the vector in a manner that will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing sequences encoding the polypeptides of the human Ron-V1, Ron-V2, and Ron-V3 and appropriate transcriptional/translational control elements. These methods may include in vitro recombinant DNA and synthetic techniques, and in vivo genetic recombinants.

A variety of expression vector/host systems may be utilized to express the polypeptide-coding sequence. These include, but are not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is *E. coli*.

Alternatively, the Polypeptides of the human Ron-V1, Ron-V2, and Ron-V3 or fragments thereof may be synthesized using chemical methods. For example, peptide synthesis can be performed using various solid-phase techniques. Automated synthesis may be achieved using the ABI 431A peptide synthesizer (Perkin-Elmer).

According to the present invention, the fragments of the polypeptides and nucleic acid sequences of the human Ron-V1, Ron-V2, and Ron-V3 are used as immunogens, primers or probes. Preferable, the purified fragments of the human Ron-V1, Ron-V2, and Ron-V3 are used. The fragments may be produced by enzyme digestion, chemical cleavage of isolated or purified polypeptide or nucleic acid sequences, or chemical synthesis. Thereafter, the fragments may be isolated or purified. Such isolated or purified fragments of the polypeptides and nucleic acid sequences can be used as immunogens, primers or probes.

The present invention further provides the antibodies which specifically bind one or more out-surface epitopes of the polypeptides of the human Ron-V1, Ron-V2, and Ron-V3.

According to the present invention, immunization of mammals with immunogens described herein, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques. Such techniques are disclosed, for example, in U.S. Pat. Nos. 4,271,145 and 4,196,265. An animal is immunized with the immunogen. Hybridomas are prepared by fusing spleen cells from the immunized animal with myeloma cells. The fusion products are screened for those producing antibodies that specifically bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using well-known column chromatography methods.

According to the present invention, antibody fragments which contain specific binding sites for the polypeptides or fragments thereof may also be generated. For example, such fragments include, but are not limited to, F(ab')2 fragments produced by pepsin digestion of the antibody molecule and Fab fragments generated by reducing the disulfide bridges of the F(ab')2 fragments.

The subject invention also provides methods for diagnosing the diseases associated with Ron-V1, Ron-V2, or Ron-V3, particularly breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma, by utilizing the nucleic acid sequences, the polypeptide of the human Ron-V1, Ron-V2, or Ron-V3, or fragments thereof, and the antibodies against the polypeptides.

Since Ron-V1, Ron-V2, or Ron-V3 clones were isolated from a SW620 cDNA library, it is advisable that Ron-V1, Ron-V2, or Ron-V3 serve as a marker for the diagnosis of human colon adenocarcinoma. Thus, the expression levels/patterns of Ron-V1, Ron-V2, or Ron-V3 may be a useful indicator for screening patients suspected of having cancers or more specifically, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. This suggests that relative expression levels/patterns (mRNA or protein) may confer an increased susceptibility to cancers, and more preferably, to breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. Fragments of Ron-V1, Ron-V2, or Ron-V3 transcripts (mRNAs) may be detected by RT-PCR approach. Polypeptides of Ron-V1, Ron-V2, or Ron-V3 may be determined by the binding of antibodies to these polypeptides. These approaches may be performed in accordance with conventional methods well known to persons skilled in the art. On the other hand, a method (RNAi; RNA interference) that is known to those skilled in the art may be used to interfere and degrade the targeted RNA using chemically synthesized double stranded short nucleic acid (about 23 nucleotides dsRNA) molecules (Montgomery et al. (1998) Proc Natl Acad Sci USA. 95:15502-7). According to the present invention, the double stranded short nucleic acid molecules containing the sequences of the "gene targets": nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, which may be used to specifically interfere and degrade Ron-V1, Ron-V2, and Ron-V3 mRNAs. On the other hand, the double stranded short nucleic acid molecules containing the sequence of the "gene targets": nucleotides 2678-2679 of Ron-V2 or Ron-V3, may be used to specifically interfere and degrade Ron-V2 and Ron-V3 mRNA, respectively. After RNAi approach was conducted, the decreased transcripts or polypeptides may be used to interpret the presence of Ron-V1, Ron-V2, and Ron-V3 mRNAs.

According to the present invention, the expression of these gene variant mRNAs in sample may be determined by, but not limited to, RT-PCR. Using TRIZOL™ reagents (LIFE TECHNOLOGY®), total RNA may be isolated from patient samples. Tissue samples (e.g., biopsy samples) are powdered under liquid nitrogen before samples (e.g., biopsy samples) are powdered under liquid nitrogen before homogenization. RNA purity and integrity are assessed by absorbance at 260/280 nm and by agarose gel electrophoresis. A set of primers can be designed to amplify the expected size of specific PCR fragments (gene targets) of Ron-V1, Ron-V2, and Ron-V3. For example, one of the primers is a fragment of the sequence (A fragment; forward primer) containing the gene targets: nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, and the other is a fragment (B fragment; reverse primer) designed from a reverse complementary strand of Ron-V1, Ron-V2, and Ron-V3 sequences at any location downstream of "A fragment". If "B fragment" is designed from a reverse complementary strand of the sequence containing the gene targets: nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, the "A fragment" is a fragment of the sequence at any location upstream of "B fragment". Alternatively, one primer (A fragment; forward primer) is at any location upstream of the sequence containing "gene targets" and the other is designed from a reverse complementary strand at any location downstream of the sequence containing "gene targets". PCR fragments are analyzed on a 1% agarose gel using five microliters (10%) of the amplified products. The intensity of the signals may be determined by using the Molecular Analyst program (version 1.4.1; Bio-Rad). Thus, the relative expression level for each amplified PCR product may be calculated based on the intensity of signals.

The RT-PCR experiment may be performed according to the manufacturer instructions (BOEHRINGER MANNHEIM®). A 50 µl reaction mixture containing 2 µl total RNA (0.1 µg/µl), 1 µl each primer (20 pM), 1 µl each dNTP (10 mM), 2.5 µl DTT solution (100 mM), 10 µl 5×RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

The expression of gene variants can also be analyzed using Northern Blot hybridization approach. Specific fragments containing the sequences of the "gene targets" of the Ron-V1, Ron-V2, and Ron-V3 may be amplified by polymerase chain reaction (PCR) using primer set designed for RT-PCR. The amplified PCR fragment may be labeled and served as a probe to hybridize the membranes containing total RNAs extracted from the samples under the conditions of 55° C. in a suitable hybridization solution for 3 hours. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of the "gene targets" of the gene variants (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the presence of the polypeptide of Ron-V1, Ron-V2, and Ron-V3 in samples may be determined by, but not limited to, the immunoassay which uses the antibody that specifically binds to the polypeptide. The polypeptides of the gene variants may be expressed in prokaryotic cells by using suitable prokaryotic expression vectors. The cDNA fragments of Ron-V1, Ron-V2, and Ron-V3 genes encoding the amino acid sequences may be PCR amplified using primer set designed with restriction enzyme digestion sites incorporated in the 5' and 3' ends. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., E. coli BL21 (DE3)). Recombinant protein synthesis may be stimulated by the addition of 0.4 mM isopropylthiogalactoside (IPTG) for 3 h. The bacterially-expressed proteins may be purified.

The polypeptide of the gene variant may be expressed in animal cells by using eukaryotic expression vectors. Cells may be maintained in Dulbecco's modified Eagle's medium (DMEM) supplemented with 10% fetal bovine serum (FBS; GIBCO® BRL) at 37° C. in a humidified 5% CO2 atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of 5×104 cells per well. Transfections may be carried out using Lipofectaminutese Plus transfection reagent according to the manufacturer's instructions (GIBCO® BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (Ron-V1, Ron-V2, and Ron-V3) may be generated using hybridoma technique according to the conventional methods (de StGroth and Scheidegger, (1980) J Immunol Methods 35:1-21; Cote et al. (1983) Proc Natl Acad Sci USA 80: 2026-30; and Kozbor et al. (1985) J Immunol Methods 81:31-42).

According to the present invention, the presence of the polypeptides of Ron-V1, Ron-V2, and Ron-V3 in samples of the breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma may be determined by a Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 h at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Colon Adenocarcinoma EST Database

Expressed sequence tags (ESTs) generated from the large-scale PCR-based sequencing of the 5'-end of human colon adenocarcinoma cDNA clones were compiled and served as EST databases. Sequence comparisons against the nonredundant nucleotide and protein databases were performed using BLASTN and BLASTX programs, at the National Center for Biotechnology Information (NCBI™) with a significance cutoff of p<10-10. ESTs representing putative Ron-V1, Ron-V2, and Ron-V3 genes were identified during the course of EST generation.

Isolation of cDNA Clones

Three cDNA clones exhibiting EST sequences similar to the Ron gene were isolated from the human colon adenocarcinoma cDNA library and named Ron-V1, Ron-V2, and Ron-V3. The inserts of these clones were subsequently excised in vivo from the λZAP Express vector using the EXASSIST™/ XLOLR helper phage system (STRATAGENE®). Phagemid particles were excised by coinfecting XL1-BLUE MRF' cells with EXASSIST™ helper phage. The excised pBluescript phagemids were used to infect E. coli XLOLR cells, which lack the amber suppressor necessary for EXASSIST™ phage replication. Infected XLOLR cells were selected using kanamycin resistance. Resultant colonies contained the double stranded phagemid vector with the cloned cDNA insert. A single colony was grown overnight in LB-kanamycin, and DNA was purified using a QIAGEN® plasmid purification kit.

Full Length Nucleotide Sequencing and Database Comparisons

Phagemid DNA was sequenced using the Taq dye-deoxy terminator cycle sequencing kit for the APPLIED BIOSYSTEMS 377™ sequencing system (PERKINELMER® Life Sciences).

Using the primer-walking approach, full-length sequence was determined. Nucleotide and protein searches were performed using BLAST against the non-redundant database of NCBI™.

In Silico Sequence Similarity Analysis

The coding sequence for each cDNA clones was searched against the dbEST sequence database using the BLAST algorithm at the NCBI™ website. ESTs derived from dbEST sequence database were used as a source of information for transcript sequence similarity analysis. The accession numbers of the ESTs matching to the deleted sequence of Ron-V1, Ron-V2, and Ron-V3 were identified.

RT-PCR Expression Pattern Analysis

The expression patterns of Ron-V1, Ron-V2, and Ron-V3 were conducted in human cell lines using RT-PCR. The human cell lines were WI38 (Lung, fetus); A549 (Lung adenocarcinoma); H661 (Large cell carcinoma, lung); H520 (Squamous cell carcinoma, lung); H209 (Small cell carcinoma, lung); JHH-4 (Hepatoma); SUP-T1 (T-cell lymophoblastic lymphoma); Daudi (Burkitt's lymophoma); Ramos (Burkitt's lymophoma); RAJI (Burkitt's lymophoma); ZR75-1 (Breast carcinoma); MDA-MB-231 (Breast adenocarcinoma); Hs 578T (Breast carcinoma); G5T/VGH (Glioblastoma multiforme); TSGH9201 (Gastric carcinoma); Ca Ski (Cervix epidermoid carcinoma); Hela S3 (Cervical epitheloid carcinoma); COLO 320 HSR (Colon adenocarcinoma); SW620 (Colon adenocarcinoma); TSGH8301 (Urinary bladder carcinoma); ES-2 (Ovarian carcinoma); DU145 (Brain prostate carcinoma); MIA paca-2 (Pancreatic carcinoma); CE48T/VGH (Esophagus epidermoid carcinoma); CE81T/VGH (Esophagus carcinoma well differentiated aquamous); HL-CZ (Promonocytic leukemia); Hs 181.tes (Normal testis). The purity and integrity of total RNA extracted from each of the cell lines were assessed by absorbance at 260/280 nm and by agarose gel electrophoresis. The forward and reverse primers for Ron gene variants were: 5'-GACTGAGTGTCTGCTAGCACGG-3' and 5'-ATG-GCAGGGAGTGCATCTACGC-3'. The expected size of Ron-V1, Ron-V2, and Ron-V3 PCR fragments were 660 bp, 540 bp and 513 bp.

Glyceraldehyde-3-phosphate dehydrogenase (GAPDH; accession No. M33197) was used for internal control. The forward and reverse primers for GAPDH were: 5'-TGGGT-GTGAACCATGAGAAG-3' and 5'-GTGTCGCTGT-TGAAGTCAGA-3'. The expected size of GAPDH PCR fragment was 472 bp. Briefly, a 50 µl reaction mixture containing 2 µl total RNA (01 µg/µl), 1 µl each primer (20 pM), 1 µl each dNTP (10 mM), 2.5 µl DTT solution (100 mM), 10 µl 5×RT-PCR buffer, 1 µl enzyme mixture and 28.5 µl sterile redistilled water were subjected to reverse transcription at 60° C. for 30 min followed by 35 cycles of denaturation at 94° C. for 2 min, annealing at 60° C. for 2 min, and extension at 68° C. for 2 min. Five microliters (10%) of the amplified products mixed with 1 µl of loading buffer were separated on a 1% horizontal agarose gel stained with ethidium bromide in 0.5×TAE buffer. The gel was electrophoresed at 100 V for 45 min.

FIG. 7 showed that Ron-V1 (660 bp), Ron-V2 (540 bp), and Ron-V3 (513 bp) mRNAs were RT-PCR amplified using the primers described above. Shown on the left are 100 bp DNA ladder markers. The PCR fragments of Ron-V1 (660 bp), Ron-V2 (540 bp), and Ron-V3 (513 bp) were confirmed by sequencing. Ron-V1 mRNA was expressed in the cell lines of cervix epitheloid carcinoma, colon adenocarcinoma, urinary bladder carcinoma, prostate carcinoma, esophagus carcinoma, and esophagus epidermoid carcinoma; Ron-V2 mRNA was expressed in the cell lines of breast carcinoma, breast adenocarcinoma, cervix epidermoid carcinoma, colon adenocarcinoma, and urinary bladder carcinoma; Ron-V3 mRNA was expressed in the cell lines of breast carcinoma, colon adenocarcinoma, urinary bladder carcinoma, esophagus carcinoma, and esophagus epidermoid carcinoma. The differential expression pattern among Ron-V1, Ron-V2, and Ron-V3 implied that they may be functionally different and may be a suitable marker for diagnosing human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

REFERENCES

All references are listed herein for the convenience of the reader. Each is incorporated by reference in its entirety.

1. Angeloni et al., The soluble sema domain of the RON receptor inhibits macrophage-stimulating protein-induced receptor activation. J. Biol. Chem. 279:3726-32, (2004).
2. Camp et al., RON, a tyrosine kinase receptor involved in tumor progression and metastasis. Ann Surg Oncol. 12:273-81, (2005).
3. Peace et al., Ron receptor signaling augments mammary tumor formation and metastasis in a murine model of breast cancer. Cancer Res. 65:1285-93, (2005).
4. Wang et al., Oncogenic and invasive potentials of human macrophage-stimulating protein receptor, the RON receptor tyrosine kinase. Carcinogenesis 24:1291-300, (2003).
5. Willett et al., Differential screening of a human chromosome 3 library identifies hepatocyte growth factor-like/macrophage-stimulating protein and its receptor in injured lung. Possible implications for neuroendocrine cell survival. J Clin Invest. 99:2979-91, (1997).

The invention claimed is:

1. An isolated nucleic acid encoding the amino acid sequence of SEQ ID NO: 4.

2. The isolated nucleic acid of claim 1, comprising the nucleotide sequence of SEQ ID NO: 3.

3. An isolated nucleic acid consisting of 30 consecutive nucleotides of SEQ ID NO: 3 and that overlaps a dinucleotide selected from the group consisting of nucleotides 2837-2838 of SEQ ID NO: 3, nucleotides 3583-3584 of SEQ ID NO: 3, and nucleotides 3725-3726 of SEQ ID NO: 3.

4. An expression vector comprising the nucleic acid of claims 1 or 2.

5. An isolated host cell comprising said expression vector of claim 4.

6. A method for producing a RON variant polypeptide, comprising the steps of a) culturing said host cell of claim 5 under a condition suitable for the expression of a RON variant polypeptide; and b) recovering said RON variant polypeptide from the host cell culture.

* * * * *

SEQUENCE LISTING

<160> NUMBER OF SEQ ID NOS: 8

<210> SEQ ID NO 1
<211> LENGTH: 4541
<212> TYPE: DNA
<213> ORGANISM: Homo sapiens

<400> SEQUENCE: 1
ggatcctcta gggtcccagc tcgcctcgat ggagctcctc ccgccgctgc ctcagtcctt    60

-continued

```
cctgttgctg ctgctgttgc ctgccaagcc cgcggcgggc gaggactggc agtgcccgcg      120
caccccctac gcggcctctc gcgactttga cgtgaagtac gtggtgccca gcttctccgc      180
cggaggcctg gtacaggcca tggtgaccta cgagggcgca agaaatgaga gtgctgtgtt      240
tgtagccata cgcaatcgcc tgcatgtgct tgggcctgac ctgaagtctg tccagagcct      300
ggccacgggc cctgctggag accctggctg ccagacgtgt gcagcctgtg cccaggacc      360 ccacggccct cccggtgaca cagacacaaa ggtgctggtg ctggatcccg cgctgcctgc      420
gctggtcagt tgtggctcca gcctgcaggg ccgctgcttc ctgcatgacc tagagcccca      480
agggacagcc gtgcatctgg cagcgccagc ctgcctcttc tcagcccacc ataaccggcc      540
cgatgactgc cccgactgtg tggccagccc attgggcacc cgtgtaactg tggttgagca      600
aggccaggcc tcctatttct acgtggcatc ctcactggac gcagccgtgg ctggcagctt      660
cagcccacgc tcagtgtcta tcaggcgtct caaggctgac gcctcgggat tcgcaccggg      720
ctttgtggcg ttgtcagtgc tgcccaagca tcttgtctcc tacagtattg aatacgtgca      780
cagcttccac acgggagcct tcgtatactt cctgactgta cagccggcca gcgtgacaga      840
tgatcctagt gccctgcaca cacgcctggc acggcttagc gccactgagc cagagttggg      900
tgactatcgg gagctggtcc tcgactgcag atttgctcca aaacgcaggc gccgggggc      960 cccagaaggc ggacagccct accctgtgct gcaggtggcc cactccgctc cagtgggtgc     1020
ccaacttgcc actgagctga gcatcgccga gggccaggaa gtactatttg gggtcttttgt     1080 gactggcaag gatggtggtc ctggcgtggg ccccaactct gtcgtctgtg ccttcccat      1140 tgacctgctg gacacactaa ttgatgaggg tgtggagcgc tgttgtgaat ccccagtcca     1200
tccaggcctc cggcgaggcc tcgacttctt ccagtcgccc agttttttgcc caacccgcc     1260 tggcctggaa gccctcagcc ccaacaccag ctgccgccac ttccctctgc tggtcagtag     1320
cagcttctca cgtgtggacc tattcaatgg gctgttggga ccagtacagg tcactgcatt     1380
gtatgtgaca cgccttgaca acgtcacagt ggcacacatg ggcacaatgg atgggcgtat     1440
cctgcaggtg gagctggtca ggtcactaaa ctacttgctg tatgtgtcca acttctcact     1500
gggtgacagt gggcagcccg tgcagcggga tgtcagtcgt cttggggacc acctactctt     1560
tgcctctggg gaccaggttt tccaggtacc tatccgaggc cctggctgcc gccacttcct     1620
gacctgtggg cgttgcctaa gggcatggca tttcatgggc tgtggctggt gtgggaacat     1680
gtgcggccag cagaaggagt gtcctggctc ctggcaacag gaccactgcc cacctaagct     1740
tactgagttc cacccccaca gtggacctct aaggggcagt acaaggctga ccctgtgtgg     1800
ctccaacttc taccttcacc cttctggtct ggtgcctgag ggaacccatc aggtcactgt     1860
gggccaaagt ccctgccggc cactgcccaa ggacagctca aaactcagac cagtgccccg     1920
gaaagacttt gtagaggagt ttgagtgtga actggagccc ttgggcaccc aggcagtggg     1980
gcctaccaac gtcagcctca ccgtgactaa catgccaccg ggcaagcact tccgggtaga     2040
cggcacctcc gtgctgagag gcttctcttt catggagcca gtgctgatag cagtgcaacc     2100
cctctttggc ccacgggcag gaggcacctg tctcactctt gaaggccaga gtctgtctgt     2160
aggcaccagc cgggctgtgc tggtcaatgg gactgagtgt ctgctagcac gggtcagtga     2220
ggggcagctt ttatgtgcca cacccctgg ggccacggtg gccagtgtcc cccttagcct     2280
gcaggtgggg ggtgcccagg tacctggttc ctgaccttc cagtacagag aagaccctgt      2340
cgtgctaagc atcagcccca actgtggcta catcaactcc cacatcacca tctgtggcca     2400
```

-continued

```
gcatctaact tcagcatggc acttagtgct gtcattccat gacgggctta gggcagtgga      2460
aagcaggtgt gagaggcagc ttccagagca gcagctgtgc cgccttcctg aatatgtggt      2520
ccgagacccc cagggatggg tggcagggaa tctgagtgcc cgaggggatg gagctgctgg      2580
ctttacactg cctggctttc gcttcctacc cccaccccat ccacccagtg ccaacctagt      2640
tccactgaag cctgaggagc atgccattaa gtttgagtat attgggctgg gcgctgtggc      2700
tgactgtgtg ggtatcaacg tgaccgtggg tggtgagagc tgccagcacg agttccgggg      2760
ggacatggtt gtctgccccc tgcccccatc cctgcagctt ggccaggatg gtgcccatt       2820 gcaggtctgc gtagatggtg aatgtcatat cctgggtaga gtggtgcggc cagggccaga      2880
tggggtccca cagagcacgc tccttggtat cctgctgcct ttgctgctgc ttgtggctgc      2940
actggcgact gcactggtct tcagctactg gtggcggagg aagcagctag ttcttcctcc      3000
caacctgaat gacctggcat ccctggacca gactgctgga ccacacccc tgcctattct       3060 gtactcgggc tctgactaca gaagtggcct tgcactccct gccattgatg gtctggattc      3120
caccacttgt gtccatggag catccttctc cgatagtgaa gatgaatcct gtgtgccact      3180
gctgcggaaa gagtccatcc agctaaggga cctggactct cgctcttgg ctgaggtcaa       3240 ggatgtgctg attccccatg agcgggtggt cacccacagt gaccgagtca ttggcaaagg      3300
ccactttgga gttgtctacc acggagaata catagaccag gcccagaatc gaatccaatg      3360
tgccatcaag tcactaagtc gcatcacaga gatgcagcag gtggaggcct tcctgcgaga      3420
ggggctgctc atgcgtggcc tgaaccaccc gaatgtgctg gctctcattg gtatcatgtt      3480
gccacctgag ggcctgcccc atgtgctgct gccctatatg tgccacggtg acctgctcca      3540
gttcatccgc tcacctcagc ggaaccccac cgtgaaggac ctcatcagct ttggcctgca      3600
ggtagcccgc ggcatggagt acctggcaga gcagaagttt gtgcacaggg acctggctgc      3660
gcggaactgc atgctggacg agtcattcac agtcaaggtg gctgactttg gtttggcccg      3720
cgacatcctg gacagggagt actatagtgt tcaacagcat cgccacgctc gcctacctgt      3780
gaagtggatg gcgctggaga gcctgcagac ctatagattt accaccaagt ctgatgtgtg      3840
gtcatttggt gtgctgctgt gggaactgct gacacggggt gccccaccat accgccacat      3900 tgacccttt gaccttaccc acttcctggc ccagggtcgg cgcctgcccc agcctgagta       3960
ttgccctgat tctctgtacc aagtgatgca gcaatgctgg gaggcagacc cagcagtgcg      4020
acccaccttc agagtactag tgggggaggt ggagcagata gtgtctgcac tgcttgggga      4080
ccattatgtg cagctgccag caacctacat gaacttgggc cccagcacct cgcatgagat      4140
gaatgtgcgt ccagaacagc cgcagttctc acccatgcca gggaatgtac gccggccccg      4200
gccactctca gagcctcctc ggcccacttg acttagttct tgggctggac ctgcttagct      4260
gccttgagct aaccccaagg ctgcctctgg gccatgccag gcagagcag tggccctcca       4320 ccttgttcct gcccttaac tttcagaggc aataggtaaa tgggcccatt aggtccctca       4380
ctccacagag tgagccagtg agggcagtcc tgcaacatgt atttatggag tgcctgctgt      4440
ggaccctgtc ttctgggcac agtggactca gcagtgacca caccaacact gacccttgaa      4500
ccaataaagg aacaaatgac tattaaagca caaaaaaaa a                           4541
```

<210> SEQ ID NO 2
<211> LENGTH: 1400
<212> TYPE: PRT
<213> ORGANISM: Homo sapiens

<400> SEQUENCE: 2

-continued

```
Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
            115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415
```

-continued

```
Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
```

-continued

```
                835                 840                 845
Ala Ala Gly Phe Thr Leu Pro Gly Phe Arg Phe Leu Pro Pro His
    850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
        900                 905                 910

Met Val Val Cys Pro Leu Pro Ser Leu Gln Leu Gly Gln Asp Gly
            915                 920                 925

Ala Pro Leu Gln Val Cys Val Asp Gly Glu Cys His Ile Leu Gly Arg
    930                 935                 940

Val Val Arg Pro Gly Pro Asp Gly Val Pro Gln Ser Thr Leu Leu Gly
945                 950                 955                 960

Ile Leu Leu Pro Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
        980                 985                 990

Leu Asn Asp Leu Ala Ser Leu Asp  Gln Thr Ala Gly Ala  Thr Pro Leu
            995                 1000                1005

Pro Ile  Leu Tyr Ser Gly Ser  Asp Tyr Arg Ser Gly  Leu Ala Leu
    1010                1015                1020

Pro Ala  Ile Asp Gly Leu Asp  Ser Thr Thr Cys Val  His Gly Ala
    1025                1030                1035

Ser Phe  Ser Asp Ser Glu Asp  Glu Ser Cys Val Pro  Leu Leu Arg
    1040                1045                1050

Lys Glu  Ser Ile Gln Leu Arg  Asp Leu Asp Ser Ala  Leu Leu Ala
    1055                1060                1065

Glu Val  Lys Asp Val Leu Ile  Pro His Glu Arg Val  Val Thr His
    1070                1075                1080

Ser Asp  Arg Val Ile Gly Lys  Gly His Phe Gly Val  Val Tyr His
    1085                1090                1095

Gly Glu  Tyr Ile Asp Gln Ala  Gln Asn Arg Ile Gln  Cys Ala Ile
    1100                1105                1110

Lys Ser  Leu Ser Arg Ile Thr  Glu Met Gln Gln Val  Glu Ala Phe
    1115                1120                1125

Leu Arg  Glu Gly Leu Leu Met  Arg Gly Leu Asn His  Pro Asn Val
    1130                1135                1140

Leu Ala  Leu Ile Gly Ile Met  Leu Pro Pro Glu Gly  Leu Pro His
    1145                1150                1155

Val Leu  Leu Pro Tyr Met Cys  His Gly Asp Leu Leu  Gln Phe Ile
    1160                1165                1170

Arg Ser  Pro Gln Arg Asn Pro  Thr Val Lys Asp Leu  Ile Ser Phe
    1175                1180                1185

Gly Leu  Gln Val Ala Arg Gly  Met Glu Tyr Leu Ala  Glu Gln Lys
    1190                1195                1200

Phe Val  His Arg Asp Leu Ala  Ala Arg Asn Cys Met  Leu Asp Glu
    1205                1210                1215

Ser Phe  Thr Val Lys Val Ala  Asp Phe Gly Leu Ala  Arg Asp Ile
    1220                1225                1230

Leu Asp  Arg Glu Tyr Tyr Ser  Val Gln Gln His Arg  His Ala Arg
    1235                1240                1245
```

| Leu | Pro | Val | Lys | Trp | Met | Ala | Leu | Glu | Ser | Leu | Gln | Thr | Tyr | Arg |
|-----|-----|-----|-----|-----|-----|-----|-----|-----|-----|-----|-----|-----|-----|-----|
| | 1250 | | | | 1255 | | | | 1260 | | | | | |

Phe Thr Thr Lys Ser Asp Val Trp Ser Phe Gly Val Leu Leu Trp
   1265                       1270                        1275

Glu Leu Leu Thr Arg Gly Ala Pro Pro Tyr Arg His Ile Asp Pro
   1280                       1285                        1290

Phe Asp Leu Thr His Phe Leu Ala Gln Gly Arg Arg Leu Pro Gln
   1295                       1300                        1305

Pro Glu Tyr Cys Pro Asp Ser Leu Tyr Gln Val Met Gln Gln Cys
   1310                       1315                        1320

Trp Glu Ala Asp Pro Ala Val Arg Pro Thr Phe Arg Val Leu Val
   1325                       1330                        1335

Gly Glu Val Glu Gln Ile Val Ser Ala Leu Leu Gly Asp His Tyr
   1340                       1345                        1350

Val Gln Leu Pro Ala Thr Tyr Met Asn Leu Gly Pro Ser Thr Ser
   1355                       1360                        1365

His Glu Met Asn Val Arg Pro Glu Gln Pro Gln Phe Ser Pro Met
   1370                       1375                        1380

Pro Gly Asn Val Arg Arg Pro Arg Pro Leu Ser Glu Pro Pro Arg
   1385                       1390                        1395

Pro Thr
   1400

<210> SEQ ID NO 3
<211> LENGTH: 4000
<212> TYPE: DNA
<213> ORGANISM: Homo sapiens

<400> SEQUENCE: 3

```
ggatcctcta gggtcccagc tcgcctcgat ggagctcctc ccgccgctgc ctcagtcctt     60
cctgttgctg ctgctgttgc ctgccaagcc cgcggcgggc gaggactggc agtgcccgcg    120
caccccctac gcggcctctc gcgactttga cgtgaagtac gtggtgccca gcttctccgc    180
cggaggcctg gtacaggcca tggtgaccta cgagggcgac agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg cccaggacc    360 ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat cgcaccggg    720 ctttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc agagttggg    900 tgactatcgg gagctggtcc tcgactgcag atttgctcca aaacgcaggc gccggggggc    960
cccagaaggc ggacagcccc acctgtgct gcaggtggcc cactccgctc cagtgggtgc   1020
ccaacttgcc actgagctga gcatcgccga gggccaggaa gtactatttg gggtcttgt   1080 gactggcaag gatggtggtc ctggcgtggg ccccaactct gtcgtctgtg ccttccccat   1140
```

```
tgacctgctg gacacactaa ttgatgaggg tgtggagcgc tgttgtgaat ccccagtcca   1200
tccaggcctc cggcgaggcc tcgacttctt ccagtcgccc agttttttgcc ccaacccgcc   1260
tggcctggaa gccctcagcc ccaacaccag ctgccgccac ttccctctgc tggtcagtag   1320
cagcttctca cgtgtggacc tattcaatgg gctgttggga ccagtacagg tcactgcatt   1380
gtatgtgaca cgccttgaca acgtcacagt ggcacacatg ggcacaatgg atgggcgtat   1440
cctgcaggtg gagctggtca ggtcactaaa ctacttgctg tatgtgtcca acttctcact   1500
gggtgacagt gggcagcccg tgcagcggga tgtcagtcgt cttggggacc acctactctt   1560
tgcctctggg gaccaggttt tccaggtacc tatccgaggc cctggctgcc gccacttcct   1620
gacctgtggg cgttgcctaa gggcatggca tttcatgggc tgtggctggt gtgggaacat   1680
gtgcggccag cagaaggagt gtcctggctc ctggcaacag gaccactgcc cacctaagct   1740
tactgagttc cacccccaca gtggacctct aagggcagt acaaggctga ccctgtgtgg   1800
ctccaacttc taccttcacc cttctggtct ggtgcctgag ggaacccatc aggtcactgt   1860
gggcaaagt ccctgccggc cactgccaa ggacagctca aaactcagac cagtgccccg   1920
gaaagacttt gtagaggagt ttgagtgtga actggagccc ttgggcaccc aggcagtggg   1980
gcctaccaac gtcagcctca ccgtgactaa catgccaccg ggcaagcact tccgggtaga   2040
cggcacctcc gtgctgagag gcttctcttt catggagcca gtgctgatag cagtgcaacc   2100
cctctttggc ccacgggcag gaggcacctg tctcactctt gaaggccaga gtctgtctgt   2160
aggcaccagc cgggctgtgc tggtcaatgg gactgagtgt ctgctagcac gggtcagtga   2220
ggggcagctt ttatgtgcca caccccctgg ggccacggtg ccagtgtcc cccttagcct   2280
gcaggtgggg ggtgcccagg tacctggttc ctggaccttc cagtacagag aagaccctgt   2340
cgtgctaagc atcagcccca actgtggcta catcaactcc cacatcacca tctgtggcca   2400
gcatctaact tcagcatggc acttagtgct gtcattccat gacgggctta gggcagtgga   2460
aagcaggtgt gagaggcagc ttccagagca gcagctgtgc cgccttcctg aatatgtggt   2520
ccgagacccc cagggatggg tggcaggaa tctgagtgcc cgaggggatg gagctgctgg   2580
ctttacactg cctggctttc gcttcctacc cccacccat ccacccagtg ccaacctagt   2640
tccactgaag cctgaggagc atgccattaa gtttgagtat attgggctgg gcgctgtggc   2700
tgactgtgtg ggtatcaacg tgaccgtggg tggtgagagc tgccagcacg agttccgggg   2760
ggacatggtt gtctgccccc tgcccccatc cctgcagctt ggccaggatg gtgccccatt   2820
gcaggtctgc gtagatgcac tccctgccat tgatggtctg gattccacca cttgtgtcca   2880
tggagcatcc ttctccgata gtgaagatga atcctgtgtg ccactgctgc ggaaagagtc   2940
catccagcta agggacctgg actctgcgct cttggctgag gtcaaggatg tgctgattcc   3000
ccatgagcgg gtggtcaccc acagtgaccg agtcattggc aaaggccact ttggagttgt   3060
ctaccacgga gaatacatag accaggccca gaatcgaatc caatgtgcca tcaagtcact   3120
aagtcgcatc acagagatgc agcaggtgga ggccttcctg cgagaggggc tgctcatgcg   3180
tggcctgaac cacccgaatg tgctggctct cattggtatc atgttgccac ctgagggcct   3240
gccccatgtg ctgctgccct atatgtgcca cggtgacctg ctccagttca tccgctcacc   3300
tcagcggaac cccaccgtga aggacctcat cagctttggc ctgcaggtag cccgcggcat   3360
ggagtacctg gcagagcaga gtttgtgcaa cagggacctg gctgcgcgga actgcatgct   3420
ggacgagtca ttcacagtca aggtggctga ctttggtttg gcccgcgaca tcctggacag   3480
```

-continued

```
ggagtactat agtgttcaac agcatcgcca cgctcgccta cctgtgaagt ggatggcgct    3540
ggagagcctg cagacctata gatttaccac caagtctgat gtggtaccaa gtgatgcagc    3600
aatgctggga ggcagaccca gcagtgcgac ccaccttcag agtactagtg ggggaggtgg    3660
agcagatagt gtctgcactg cttggggacc attatgtgca gctgccagca acctacatga    3720
acttgagcta accccaaggc tgcctctggg ccatgccagg ccagagcagt ggccctccac    3780
cttgttcctg cccttttaact ttcagaggca ataggtaaat gggcccatta ggtccctcac    3840
tccacagagt gagccagtga gggcagtcct gcaacatgta tttatggagt gcctgctgtg    3900
gaccctgtct tctgggcaca gtggactcag cagtgaccac accaacactg acccttgaac    3960
caataaagga acaaatgact attaaagcac aaaaaaaaa                          4000
```

<210> SEQ ID NO 4
<211> LENGTH: 1261
<212> TYPE: PRT
<213> ORGANISM: Homo sapiens

<400> SEQUENCE: 4

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285
```

-continued

Glu Leu Gly Asp Tyr Arg Glu Leu Val Leu Asp Cys Arg Phe Ala Pro
290             295                 300

Lys Arg Arg Arg Gly Ala Pro Glu Gly Gln Pro Tyr Pro Val
305             310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
            355                 360                 365

Phe Pro Ile Asp Leu Leu Asp Thr Leu Ile Asp Glu Gly Val Glu Arg
370                 375                 380

Cys Cys Glu Ser Pro Val His Pro Gly Leu Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
                420                 425                 430

Phe Ser Arg Val Asp Leu Phe Asn Gly Leu Leu Gly Pro Val Gln Val
            435                 440                 445

Thr Ala Leu Tyr Val Thr Arg Leu Asp Asn Val Thr Val Ala His Met
450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
                500                 505                 510

Ser Gly Asp Gln Val Phe Gln Val Pro Ile Arg Gly Pro Gly Cys Arg
            515                 520                 525

His Phe Leu Thr Cys Gly Arg Cys Leu Arg Ala Trp His Phe Met Gly
530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
                580                 585                 590

Asn Phe Tyr Leu His Pro Ser Gly Leu Val Pro Glu Gly Thr His Gln
                595                 600                 605

Val Thr Val Gly Gln Ser Pro Cys Arg Pro Leu Pro Lys Asp Ser Ser
            610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
                660                 665                 670

Thr Ser Val Leu Arg Gly Phe Ser Phe Met Glu Pro Val Leu Ile Ala
            675                 680                 685

Val Gln Pro Leu Phe Gly Pro Arg Ala Gly Gly Thr Cys Leu Thr Leu
690                 695                 700

-continued

```
Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro His
    850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
        915                 920                 925

Ala Pro Leu Gln Val Cys Val Asp Ala Leu Pro Ala Ile Asp Gly Leu
    930                 935                 940

Asp Ser Thr Thr Cys Val His Gly Ala Ser Phe Ser Asp Ser Glu Asp
945                 950                 955                 960

Glu Ser Cys Val Pro Leu Leu Arg Lys Glu Ser Ile Gln Leu Arg Asp
                965                 970                 975

Leu Asp Ser Ala Leu Leu Ala Glu Val Lys Asp Val Leu Ile Pro His
            980                 985                 990

Glu Arg Val Val Thr His Ser Asp Arg Val Ile Gly Lys Gly His Phe
        995                 1000                1005

Gly Val Val Tyr His Gly Glu Tyr Ile Asp Gln Ala Gln Asn Arg
        1010                1015                1020

Ile Gln Cys Ala Ile Lys Ser Leu Ser Arg Ile Thr Glu Met Gln
        1025                1030                1035

Gln Val Glu Ala Phe Leu Arg Glu Gly Leu Leu Met Arg Gly Leu
        1040                1045                1050

Asn His Pro Asn Val Leu Ala Leu Ile Gly Ile Met Leu Pro Pro
        1055                1060                1065

Glu Gly Leu Pro His Val Leu Pro Tyr Met Cys His Gly Asp
        1070                1075                1080

Leu Leu Gln Phe Ile Arg Ser Pro Gln Arg Asn Pro Thr Val Lys
        1085                1090                1095

Asp Leu Ile Ser Phe Gly Leu Gln Val Ala Arg Gly Met Glu Tyr
        1100                1105                1110

Leu Ala Glu Gln Lys Phe Val His Arg Asp Leu Ala Ala Arg Asn
```

-continued

```
                  1115                1120                1125

Cys Met Leu Asp Glu Ser Phe Thr Val Lys Val Ala Asp Phe Gly
        1130                1135                1140

Leu Ala Arg Asp Ile Leu Asp Arg Glu Tyr Tyr Ser Val Gln Gln
        1145                1150                1155

His Arg His Ala Arg Leu Pro Val Lys Trp Met Ala Leu Glu Ser
        1160                1165                1170

Leu Gln Thr Tyr Arg Phe Thr Thr Lys Ser Asp Val Val Pro Ser
        1175                1180                1185

Asp Ala Ala Met Leu Gly Gly Arg Pro Ser Ser Ala Thr His Leu
        1190                1195                1200

Gln Ser Thr Ser Gly Gly Gly Gly Ala Asp Ser Val Cys Thr Ala
        1205                1210                1215

Trp Gly Pro Leu Cys Ala Ala Ala Ser Asn Leu His Glu Leu Glu
        1220                1225                1230

Leu Thr Pro Arg Leu Pro Leu Gly His Ala Arg Pro Glu Gln Trp
        1235                1240                1245

Pro Ser Thr Leu Phe Leu Pro Phe Asn Phe Gln Arg Gln
        1250                1255                1260
```

<210> SEQ ID NO 5
<211> LENGTH: 3880
<212> TYPE: DNA
<213> ORGANISM: Homo sapiens

<400> SEQUENCE: 5

```
ggatcctcta gggtcccagc tcgcctcgat ggagctcctc ccgccgctgc ctcagtcctt     60
cctgttgctg ctgctgttgc ctgccaagcc gcggcgggc gaggactggc agtgcccgcg    120
caccccctac gcggcctctc gcgactttga cgtgaagtac gtggtgccca gcttctccgc    180
cggaggcctg gtacaggcca tggtgaccta cgagggcgca gaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg cccaggacc    360
ccacggccct cccggtgaca cagacacaaa ggtgctggtg ctggatcccg cgctgcctgc    420
gctggtcagt gtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat cgcaccggg    720
cttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc agagttggg    900
tgactatcgg gagctggtcc tcgactgcag atttgctcca aaacgcaggc gccggggggc    960
cccagaaggc ggacagccct accctgtgct gcaggtggcc cactccgctc cagtgggtgc   1020
ccaacttgcc actgagctga gcatcgccga gggccaggaa gtactatttg ggtctttgt   1080
gactggcaag gatggtggtc ctggcgtggg ccccaactct gtcgtctgtg ccttccccat   1140
tgacctgctg gacacactaa ttgatgaggg tgtggagcgc tgttgtgaat ccccagtcca   1200
tccaggcctc cggcgaggcc tcgacttctt ccagtcgccc agttttttgcc ccaacccgcc   1260
```

-continued

```
tggcctggaa gccctcagcc ccaacaccag ctgccgccac ttccctctgc tggtcagtag    1320
cagcttctca cgtgtggacc tattcaatgg gctgttggga ccagtacagg tcactgcatt    1380
gtatgtgaca cgccttgaca acgtcacagt ggcacacatg ggcacaatgg atgggcgtat    1440
cctgcaggtg gagctggtca ggtcactaaa ctacttgctg tatgtgtcca acttctcact    1500
gggtgacagt gggcagcccg tgcagcggga tgtcagtcgt cttggggacc acctactctt    1560
tgcctctggg gaccaggttt tccaggtacc tatccgaggc cctggctgcc gccacttcct    1620
gacctgtggg cgttgcctaa ggcatggca tttcatgggc tgtggctggt gtgggaacat    1680
gtgcggccag cagaaggagt gtcctggctc ctggcaacag gaccactgcc cacctaagct    1740
tactgagttc caccccaca gtggacctct aaggggcagt acaaggctga ccctgtgtgg    1800
ctccaacttc taccttcacc cttctggtct ggtgcctgag ggaacccatc aggtcactgt    1860
gggccaaagt ccctgccggc cactgcccaa ggacagctca aaactcagac cagtgccccg    1920
gaaagacttt gtagaggagt ttgagtgtga actggagccc ttgggcaccc aggcagtggg    1980
gcctaccaac gtcagcctca ccgtgactaa catgccaccg ggcaagcact tccgggtaga    2040 cggcaccctcc gtgctgagag gcttctcttt catggagcca gtgctgatag cagtgcaacc    2100
cctctttggc ccacgggcag gaggcacctg tctcactctt gaaggccaga gtctgtctgt    2160
aggcaccagc cgggctgtgc tggtcaatgg gactgagtgt ctgctagcac gggtcagtga    2220
ggggcagctt ttatgtgcca cacccccgg ggccacggtg gccagtgtcc ccttagcct    2280 gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
aagcaggtgt gagaggcagc ttccagagca gcagctgtgc cgccttcctg aatatgtggt    2520
ccgagacccc cagggatggg tggcaggaa tctgagtgcc cgaggggatg gagctgctgg    2580
ctttacactg cctggctttc gcttcctacc cccacccat ccacccagtg ccaacctagt    2640
tccactgaag cctgaggagc atgccattaa gtttgagctt ggccaggatg gtgccccatt    2700
gcaggtctgc gtagatgcac tccctgccat tgatggtctg gattccacca cttgtgtcca    2760
tggagcatcc ttctccgata gtgaagatga atcctgtgtg ccactgctgc ggaaagagtc    2820
catccagcta agggacctgg actctgcgct cttggctgag gtcaaggatg tgctgattcc    2880
ccatgagcgg gtggtcaccc acagtgaccg agtcattggc aaaggccact ttggagttgt    2940
ctaccacgga gaatacatag accaggccca gaatcgaatc caatgtgcca tcaagtcact    3000
aagtcgcatc acagagatgc agcaggtgga ggccttcctg cgagaggggc tgctcatgcg    3060
tggcctgaac caccccgaatg tgctggctct cattggtatc atgttgccac ctgagggcct    3120
gccccatgtg ctgctgccct atatgtgcca cggtgacctg ctccagttca tccgctcacc    3180
tcagcggaac cccaccgtga aggacctcat cagctttggc ctgcaggtag cccgcggcat    3240
ggagtacctg gcagagcaga agtttgtgca cagggacctg gctgcgcgga actgcatgct    3300
ggacgagtca ttcacagtca aggtggctga ctttggtttg gcccgcgaca tcctggacag    3360
ggagtactat agtgttcaac agcatcgcca cgctcgccta cctgtgaagt ggatggcgct    3420
ggagagcctg cagacctata gatttaccac caagtctgat gtggtaccaa gtgatgcagc    3480
aatgctggga ggcagaccca gcagtgcgac ccaccttcag agtactagtg ggggaggtgg    3540
agcagatagt gtctgcactg cttggggacc attatgtgca gctgccagca acctacatga    3600
acttgagcta accccaaggc tgcctctggg ccatgccagg ccagagcagt ggccctccac    3660
```

-continued

```
cttgttcctg ccctttaact ttcagaggca ataggtaaat gggcccatta ggtccctcac    3720
tccacagagt gagccagtga gggcagtcct gcaacatgta tttatggagt gcctgctgtg    3780
gaccctgtct tctgggcaca gtggactcag cagtgaccac accaacactg acccttgaac    3840
caataaagga acaaatgact attaaagcac aaaaaaaaaa                          3880
```

<210> SEQ ID NO 6
<211> LENGTH: 1221
<212> TYPE: PRT
<213> ORGANISM: Homo sapiens

<400> SEQUENCE: 6

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335
```

```
Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
            355                 360                 365

Phe Pro Ile Asp Leu Leu Asp Thr Leu Ile Asp Glu Gly Val Glu Arg
            370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
            435                 440                 445

Thr Ala Leu Tyr Val Thr Arg Leu Asp Asn Val Thr Val Ala His Met
            450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
            515                 520                 525

His Phe Leu Thr Cys Gly Arg Cys Leu Arg Ala Trp His Phe Met Gly
            530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
            595                 600                 605

Val Thr Val Gly Gln Ser Pro Cys Arg Pro Leu Pro Lys Asp Ser Ser
            610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
            675                 680                 685

Val Gln Pro Leu Phe Gly Pro Arg Ala Gly Gly Thr Cys Leu Thr Leu
            690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750
```

-continued

```
Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
        770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
            805                 810                 815

Gln Leu Pro Glu Gln Gln Leu Cys Arg Leu Pro Glu Tyr Val Val Arg
        820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro His
850                 855                 860

Pro Pro Ser Ala Asn Leu Val Pro Leu Lys Pro Glu Glu His Ala Ile
865                 870                 875                 880

Lys Phe Glu Leu Gly Gln Asp Gly Ala Pro Leu Gln Val Cys Val Asp
            885                 890                 895

Ala Leu Pro Ala Ile Asp Gly Leu Asp Ser Thr Thr Cys Val His Gly
        900                 905                 910

Ala Ser Phe Ser Asp Ser Glu Asp Glu Ser Cys Val Pro Leu Leu Arg
        915                 920                 925

Lys Glu Ser Ile Gln Leu Arg Asp Leu Asp Ser Ala Leu Leu Ala Glu
930                 935                 940

Val Lys Asp Val Leu Ile Pro His Glu Arg Val Val Thr His Ser Asp
945                 950                 955                 960

Arg Val Ile Gly Lys Gly His Phe Gly Val Val Tyr His Gly Glu Tyr
            965                 970                 975

Ile Asp Gln Ala Gln Asn Arg Ile Gln Cys Ala Ile Lys Ser Leu Ser
        980                 985                 990

Arg Ile Thr Glu Met Gln Gln Val  Glu Ala Phe Leu Arg  Glu Gly Leu
        995                 1000                 1005

Leu Met  Arg Gly Leu Asn His  Pro Asn Val Leu Ala  Leu Ile Gly
     1010                 1015                 1020

Ile Met  Leu Pro Pro Glu Gly  Leu Pro His Val Leu  Leu Pro Tyr
     1025                 1030                 1035

Met Cys  His Gly Asp Leu Leu  Gln Phe Ile Arg Ser  Pro Gln Arg
     1040                 1045                 1050

Asn Pro  Thr Val Lys Asp Leu  Ile Ser Phe Gly Leu  Gln Val Ala
     1055                 1060                 1065

Arg Gly  Met Glu Tyr Leu Ala  Glu Gln Lys Phe Val  His Arg Asp
     1070                 1075                 1080

Leu Ala  Ala Arg Asn Cys Met  Leu Asp Glu Ser Phe  Thr Val Lys
     1085                 1090                 1095

Val Ala  Asp Phe Gly Leu Ala  Arg Asp Ile Leu Asp  Arg Glu Tyr
     1100                 1105                 1110

Tyr Ser  Val Gln Gln His Arg  His Ala Arg Leu Pro  Val Lys Trp
     1115                 1120                 1125

Met Ala  Leu Glu Ser Leu Gln  Thr Tyr Arg Phe Thr  Thr Lys Ser
     1130                 1135                 1140

Asp Val  Val Pro Ser Asp Ala  Ala Met Leu Gly Gly  Arg Pro Ser
     1145                 1150                 1155

Ser Ala  Thr His Leu Gln Ser  Thr Ser Gly Gly Gly  Gly Ala Asp
```

```
          1160                1165                1170
Ser Val Cys Thr Ala Trp Gly Pro Leu Cys Ala Ala Ala Ser Asn
    1175                1180                1185

Leu His Glu Leu Glu Leu Thr Pro Arg Leu Pro Leu Gly His Ala
    1190                1195                1200

Arg Pro Glu Gln Trp Pro Ser Thr Leu Phe Leu Pro Phe Asn Phe
    1205                1210                1215

Gln Arg Gln
    1220

<210> SEQ ID NO 7
<211> LENGTH: 3853
<212> TYPE: DNA
<213> ORGANISM: Homo sapiens

<400> SEQUENCE: 7
ggatcctcta gggtcccagc tcgcctcgat ggagctcctc ccgccgctgc ctcagtcctt      60
cctgttgctg ctgctgttgc ctgccaagcc cgcggcgggc gaggactggc agtgcccgcg     120
caccccctac gcggcctctc gcgactttga cgtgaagtac gtggtgccca gcttctccgc     180
cggaggcctg gtacaggcca tggtgaccta cgagggcgac agaaatgaga gtgctgtgtt     240
tgtagccata cgcaatcgcc tgcatgtgct tgggcctgac ctgaagtctg tccagagcct     300
ggccacgggc cctgctggag accctggctg ccagacgtgt gcagcctgtg cccaggacc      360 ccacggccct cccggtgaca cagacacaaa ggtgctggtg ctggatcccg cgctgcctgc     420
gctggtcagt tgtggctcca gcctgcaggg ccgctgcttc ctgcatgacc tagagcccca     480
agggacagcc gtgcatctgg cagcgccagc ctgcctcttc tcagcccacc ataaccggcc     540
cgatgactgc cccgactgtg tggccagccc attgggcacc cgtgtaactg tggttgagca     600
aggccaggcc tcctatttct acgtggcatc ctcactggac gcagccgtgg ctggcagctt     660
cagcccacgc tcagtgtcta tcaggcgtct caaggctgac gcctcgggat tcgcaccggg     720
ctttgtggcg ttgtcagtgc tgcccaagca tcttgtctcc tacagtattg aatacgtgca     780
cagcttccac acgggagcct tcgtatactt cctgactgta cagccggcca gcgtgacaga     840
tgatcctagt gccctgcaca cacgcctggc acggcttagc gccactgagc agagttggg      900 tgactatcgg gagctggtcc tcgactgcag atttgctcca aaacgcaggc gccggggggc     960
cccagaaggc ggacagccct accctgtgct gcaggtggcc cactccgctc cagtgggtgc    1020
ccaacttgcc actgagctga gcatcgccga gggccaggaa gtactatttg gggtctttgt    1080
gactggcaag gatggtggtc ctggcgtggg ccccaactct gtcgtctgtg ccttccccat    1140
tgacctgctg gacacactaa ttgatgaggg tgtggagcgc tgttgtgaat ccccagtcca    1200
tccaggcctc cggcgaggcc tcgacttctt ccagtcgccc agtttttgcc ccaacccgcc    1260
tggcctggaa gccctcagcc ccaacaccag ctgccgccac ttccctctgc tggtcagtag    1320
cagcttctca cgtgtggacc tattcaatgg gctgttggga ccagtacagg tcactgcatt    1380
gtatgtgaca cgccttgaca acgtcacagt ggcacacatg ggcacaatgg atgggcgtat    1440
cctgcaggtg gagctggtca ggtcactaaa ctacttgctg tatgtgtcca acttctcact    1500
gggtgacagt gggcagcccg tgcagcggga tgtcagtcgt cttggggacc acctactctt    1560
tgcctctggg gaccaggttt tccaggtacc tatccgaggc cctggctgcc gccacttcct    1620
gacctgtggg cgttgcctaa gggcatggca tttcatgggc tgtggctggt gtgggaacat    1680
gtgcggccag cagaaggagt gtcctggctc ctggcaacag gaccactgcc cacctaagct    1740
```

```
tactgagttc caccccaca gtggacctct aaggggcagt acaaggctga ccctgtgtgg    1800
ctccaacttc taccttcacc cttctggtct ggtgcctgag ggaacccatc aggtcactgt    1860
gggccaaagt ccctgccggc cactgcccaa ggacagctca aaactcagac cagtgccccg    1920
gaaagacttt gtagaggagt ttgagtgtga actggagccc ttgggcaccc aggcagtggg    1980
gcctaccaac gtcagcctca ccgtgactaa catgccaccg ggcaagcact tccgggtaga    2040
cggcacctcc gtgctgagag gcttctcttt catggagcca gtgctgatag cagtgcaacc    2100
cctctttggc ccacgggcag gaggcacctg tctcactctt gaaggccaga gtctgtctgt    2160
aggcaccagc cgggctgtgc tggtcaatgg gactgagtgt ctgctagcac gggtcagtga    2220
ggggcagctt ttatgtgcca caccccctgg ggccacggtg gccagtgtcc cccttagcct    2280
gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
aagcaggtgt gagaggcagc ttccagagca gcagctgtgc cgccttcctg aatatgtggt    2520
ccgagacccc cagggatggg tggcagggaa tctgagtgcc cgaggggatg gagctgctgg    2580
ctttacactg cctggctttc gcttcctacc cccaccccat ccaccagtg ccaacctagt    2640
tccactgaag cctgaggagc atgccattaa gtttgaggtc tgcgtagatg cactccctgc    2700
cattgatggt ctggattcca ccacttgtgt ccatggagca tccttctccg atagtgaaga    2760
tgaatcctgt gtgccactgc tgcggaaaga gtccatccag ctaagggacc tggactctgc    2820
gctcttggct gaggtcaagg atgtgctgat tccccatgag cgggtggtca cccacagtga    2880
ccgagtcatt ggcaaaggcc actttggagt tgtctaccac ggagaataca tagaccaggc    2940
ccagaatcga atccaatgtg ccatcaagtc actaagtcgc atcacagaga tgcagcaggt    3000
ggaggccttc ctgcgagagg ggctgctcat gcgtggcctg aaccacccga atgtgctggc    3060
tctcattggt atcatgttgc cacctgaggg cctgccccat gtgctgctgc cctatatgtg    3120
ccacggtgac ctgctccagt tcatccgctc acctcagcgg aacccaccg tgaaggacct    3180
catcagcttt ggcctgcagg tagcccgcgg catggagtac ctggcagagc agaagtttgt    3240
gcacagggac ctggctgcgc ggaactgcat gctggacgag tcattcacag tcaaggtggc    3300
tgactttggt ttggcccgcg acatcctgga cagggagtac tatagtgttc aacagcatcg    3360
ccacgctcgc ctacctgtga agtggatggc gctggagagc ctgcagacct atagatttac    3420
caccaagtct gatgtggtac caagtgatgc agcaatgctg ggaggcagac ccagcagtgc    3480
gacccacctt cagagtacta gtgggggagg tggagcagat agtgtctgca ctgcttgggg    3540
accattatgt gcagctgcca gcaacctaca tgaacttgag ctaaccccaa ggctgcctct    3600
gggccatgcc aggccagagc agtggccctc caccttgttc ctgcccttta actttcagag    3660
gcaataggta aatgggccca ttaggtccct cactccacag agtgagccag tgagggcagt    3720
cctgcaacat gtatttatgg agtgcctgct gtggaccctg tcttctgggc acagtggact    3780
cagcagtgac cacaccaaca ctgacccttg aaccaataaa ggaacaaatg actattaaag    3840
cacaaaaaaa aaa                                                      3853
```

<210> SEQ ID NO 8
<211> LENGTH: 1212
<212> TYPE: PRT
<213> ORGANISM: Homo sapiens

<400> SEQUENCE: 8

```
Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
            35                  40                  45

Phe Ser Ala Gly Gly Leu Val Gln Ala Met Val Thr Tyr Glu Gly Asp
50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
            115                 120                 125

Leu Pro Ala Leu Val Ser Cys Gly Ser Ser Leu Gln Gly Arg Cys Phe
130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
            195                 200                 205

Gly Ser Phe Ser Pro Arg Ser Val Ser Ile Arg Arg Leu Lys Ala Asp
210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
            275                 280                 285

Glu Leu Gly Asp Tyr Arg Glu Leu Val Leu Asp Cys Arg Phe Ala Pro
290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
            355                 360                 365

Phe Pro Ile Asp Leu Leu Asp Thr Leu Ile Asp Glu Gly Val Glu Arg
370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415
```

```
Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
        450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
            515                 520                 525

His Phe Leu Thr Cys Gly Arg Cys Leu Arg Ala Trp His Phe Met Gly
            530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
                595                 600                 605

Val Thr Val Gly Gln Ser Pro Cys Arg Pro Leu Pro Lys Asp Ser Ser
            610                 615                 620

Lys Leu Arg Pro Val Pro Arg Lys Asp Phe Val Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
                660                 665                 670

Thr Ser Val Leu Arg Gly Phe Ser Phe Met Glu Pro Val Leu Ile Ala
            675                 680                 685

Val Gln Pro Leu Phe Gly Pro Arg Ala Gly Gly Thr Cys Leu Thr Leu
            690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
            755                 760                 765

Asp Pro Val Val Leu Ser Ile Ser Pro Asn Cys Gly Tyr Ile Asn Ser
            770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830
```

```
Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860

Pro Pro Ser Ala Asn Leu Val Pro Leu Lys Pro Glu Glu His Ala Ile
865                 870                 875                 880

Lys Phe Glu Val Cys Val Asp Ala Leu Pro Ala Ile Asp Gly Leu Asp
                885                 890                 895

Ser Thr Thr Cys Val His Gly Ala Ser Phe Ser Asp Ser Glu Asp Glu
            900                 905                 910

Ser Cys Val Pro Leu Leu Arg Lys Glu Ser Ile Gln Leu Arg Asp Leu
        915                 920                 925

Asp Ser Ala Leu Leu Ala Glu Val Lys Asp Val Leu Ile Pro His Glu
    930                 935                 940

Arg Val Val Thr His Ser Asp Arg Val Ile Gly Lys Gly His Phe Gly
945                 950                 955                 960

Val Val Tyr His Gly Glu Tyr Ile Asp Gln Ala Gln Asn Arg Ile Gln
                965                 970                 975

Cys Ala Ile Lys Ser Leu Ser Arg Ile Thr Glu Met Gln Gln Val Glu
            980                 985                 990

Ala Phe Leu Arg Glu Gly Leu Leu Met Arg Gly Leu Asn His Pro Asn
        995                 1000                1005

Val Leu Ala Leu Ile Gly Ile Met Leu Pro Pro Glu Gly Leu Pro
        1010                1015                1020

His Val Leu Leu Pro Tyr Met Cys His Gly Asp Leu Leu Gln Phe
        1025                1030                1035

Ile Arg Ser Pro Gln Arg Asn Pro Thr Val Lys Asp Leu Ile Ser
        1040                1045                1050

Phe Gly Leu Gln Val Ala Arg Gly Met Glu Tyr Leu Ala Glu Gln
        1055                1060                1065

Lys Phe Val His Arg Asp Leu Ala Ala Arg Asn Cys Met Leu Asp
        1070                1075                1080

Glu Ser Phe Thr Val Lys Val Ala Asp Phe Gly Leu Ala Arg Asp
        1085                1090                1095

Ile Leu Asp Arg Glu Tyr Tyr Ser Val Gln Gln His Arg His Ala
        1100                1105                1110

Arg Leu Pro Val Lys Trp Met Ala Leu Glu Ser Leu Gln Thr Tyr
        1115                1120                1125

Arg Phe Thr Thr Lys Ser Asp Val Val Pro Ser Asp Ala Ala Met
        1130                1135                1140

Leu Gly Gly Arg Pro Ser Ser Ala Thr His Leu Gln Ser Thr Ser
        1145                1150                1155

Gly Gly Gly Gly Ala Asp Ser Val Cys Thr Ala Trp Gly Pro Leu
        1160                1165                1170

Cys Ala Ala Ala Ser Asn Leu His Glu Leu Glu Leu Thr Pro Arg
        1175                1180                1185

Leu Pro Leu Gly His Ala Arg Pro Glu Gln Trp Pro Ser Thr Leu
        1190                1195                1200

Phe Leu Pro Phe Asn Phe Gln Arg Gln
        1205                1210
```